United States Patent
Glennie et al.

(10) Patent No.: US 11,059,898 B2
(45) Date of Patent: Jul. 13, 2021

(54) MODIFIED ANTIBODIES CONTAINING MODIFIED IGG2 DOMAINS WHICH ELICIT AGONIST OR ANTAGONISTIC PROPERTIES AND USE THEREOF

(71) Applicant: UNIVERSITY OF SOUTHAMPTON, Southampton (GB)

(72) Inventors: Martin J. Glennie, Southampton (GB); Ann White, Southampton (GB)

(73) Assignee: CANCER RESEARCH TECHNOLOGY LIMITED, London (GB)

( * ) Notice: Subject to any disclaimer, the term of this patent is extended or adjusted under 35 U.S.C. 154(b) by 0 days.

(21) Appl. No.: 15/128,781

(22) PCT Filed: Mar. 24, 2015

(86) PCT No.: PCT/IB2015/052166
§ 371 (c)(1),
(2) Date: Sep. 23, 2016

(87) PCT Pub. No.: WO2015/145360
PCT Pub. Date: Oct. 1, 2015

(65) Prior Publication Data
US 2017/0158771 A1 Jun. 8, 2017

(30) Foreign Application Priority Data

Mar. 24, 2014 (GB) ..................................... 1405264
Mar. 25, 2014 (GB) ..................................... 1405275

(51) Int. Cl.
*C07K 16/28* (2006.01)
*C07K 16/24* (2006.01)
*C07K 16/30* (2006.01)
*A61K 39/00* (2006.01)

(52) U.S. Cl.
CPC ...... *C07K 16/2878* (2013.01); *C07K 16/2818* (2013.01); *C07K 16/30* (2013.01); *A61K 2039/505* (2013.01); *C07K 16/242* (2013.01); *C07K 16/2896* (2013.01); *C07K 2317/24* (2013.01); *C07K 2317/522* (2013.01); *C07K 2317/53* (2013.01); *C07K 2317/70* (2013.01); *C07K 2317/75* (2013.01); *C07K 2317/76* (2013.01)

(58) Field of Classification Search
CPC .............. C07K 16/2878; C07K 16/30; C07K 16/2818; C07K 2317/70; C07K 2317/24; C07K 2317/75; C07K 2317/76; C07K 2317/522; C07K 2317/53; C07K 2317/52; C07K 2317/66; A61K 2039/505; A61P 37/08; A61P 37/06; A61P 37/00; A61P 35/00; A61P 31/00; A61P 29/00
See application file for complete search history.

(56) References Cited

U.S. PATENT DOCUMENTS

| 2008/0138335 A1* | 6/2008 | Takahashi | C07K 16/00 424/133.1 |
| 2011/0263830 A1* | 10/2011 | Goetsch | C07K 16/00 530/387.3 |
| 2012/0087927 A1* | 4/2012 | Matsushima | C07K 16/2878 424/153.1 |

FOREIGN PATENT DOCUMENTS

| EP | 1707627 | 10/2006 |
| EP | 2784091 | 10/2014 |
| WO | 2005007809 | 1/2005 |

OTHER PUBLICATIONS

Rudikoff et al., Proc Natl Acad Sci USA 79: 1979-1983 (Year: 1982).*
Richman et al., Cancer Immunol Res 2(1): 19-26 (Year: 2013).*
Vonderheide et al., Clin Cancer Res 19(5): 1035-1043 (Year: 2013).*
Allen et al., Biochemistry 48: 3755-3766 (Year: 2009).*
Dillon et al., J. Biol. Chem. 283, 16194-16205 (Year: 2008).*
Murray et al., Harper's Biochemistry. 23rd Edition, Chapter 4:24-28 (Year: 1993).*
Lux A, et al. "No need for constant help: human IgG2 antibodies have an autonomous agonistic activity for immunotherapy of cancer," Cancer Cell. Jan. 12, 2015;27(1):10-1.
Vonderheide RH, et al. "Agonistic CD40 antibodies and cancer therapy," Clin Cancer Res. Mar. 1, 2013;19(5):1035-43.
White AL, et al. "Conformation of the human immunoglobulin G2 hinge imparts superagonistic properties to immunostimulatory anti-cancer antibodies," Cancer Cell. Jan. 12, 2015;27(1):138-48.

* cited by examiner

*Primary Examiner* — Phuong Huynh
(74) *Attorney, Agent, or Firm* — Robin L. Teskin; Baker, Donelson, Bearman, Caldwell & Berkowitz PC

(57) ABSTRACT

Through a combination of in vitro and in vivo approaches, the inventors show that human IgG2 (h2) delivers unique FcγR-independent agonistic activity to anti-CD40 antibodies and to antibodies specific to other immunostimulatory receptors, including 4-1BB and CD28. Investigation of an anti-human CD40 mAb, LOB7.4, revealed that the unique activity of h2 was dependent upon the precise arrangement of hinge and CH1 disulfide bonds. Chemical 'shuffling' or mutagenesis to 'lock' LOB7.4 into either a more flexible 'h2A' or more compact 'h2B' conformation endowed antagonistic and agonistic properties, respectively. Engineering of h2 in this way allows development of reagents with either immunostimulatory or immunosuppressive characteristics, with direct implication for the design of therapeutic mAb agents and fusion proteins.

8 Claims, 28 Drawing Sheets

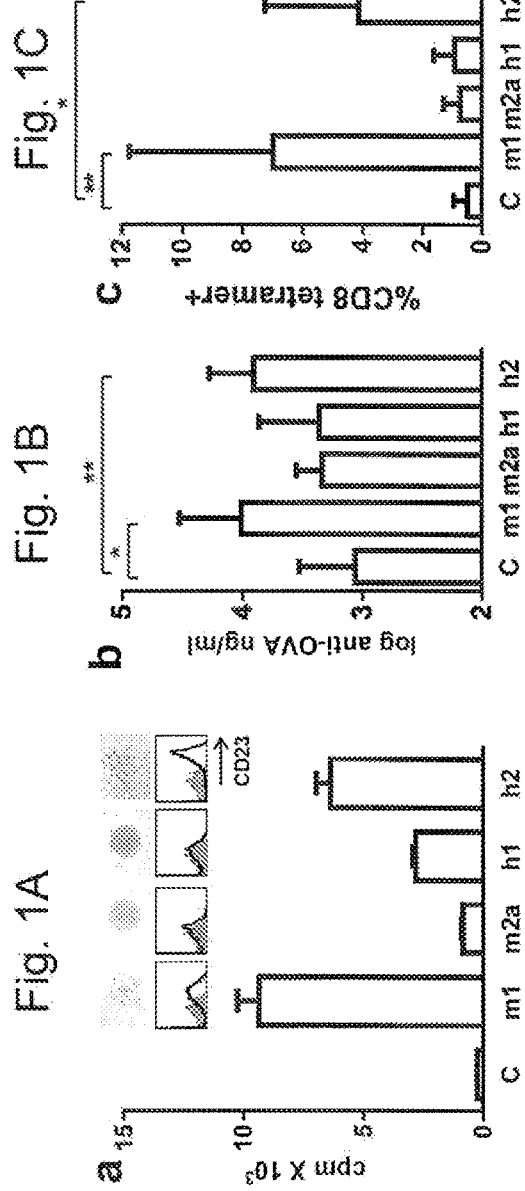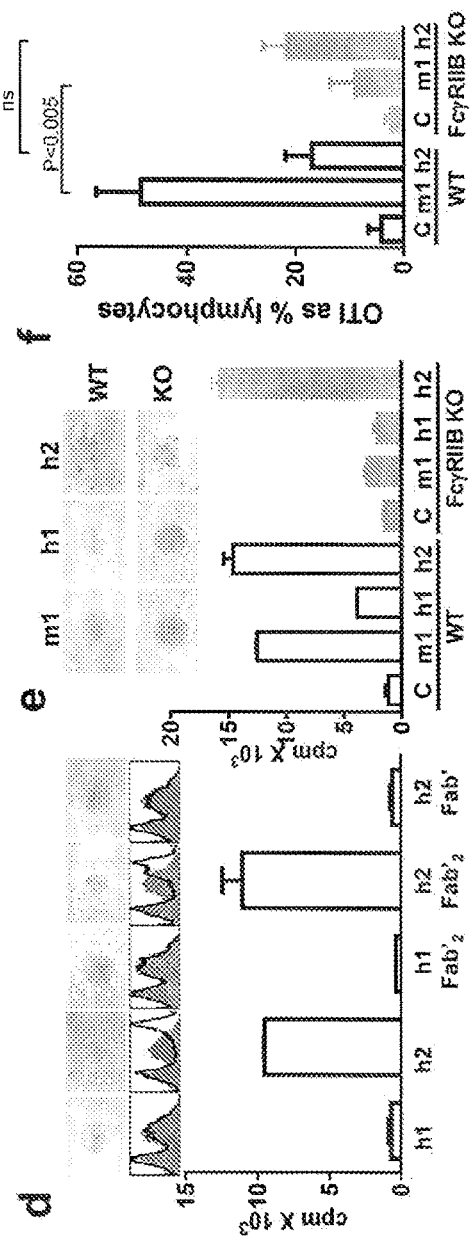

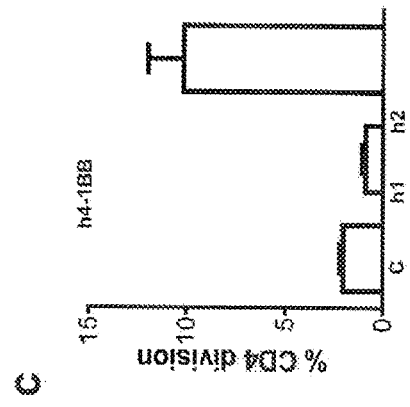
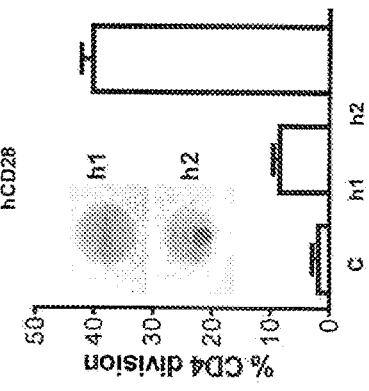
Fig. 2A
Fig. 2B
Fig. 2C

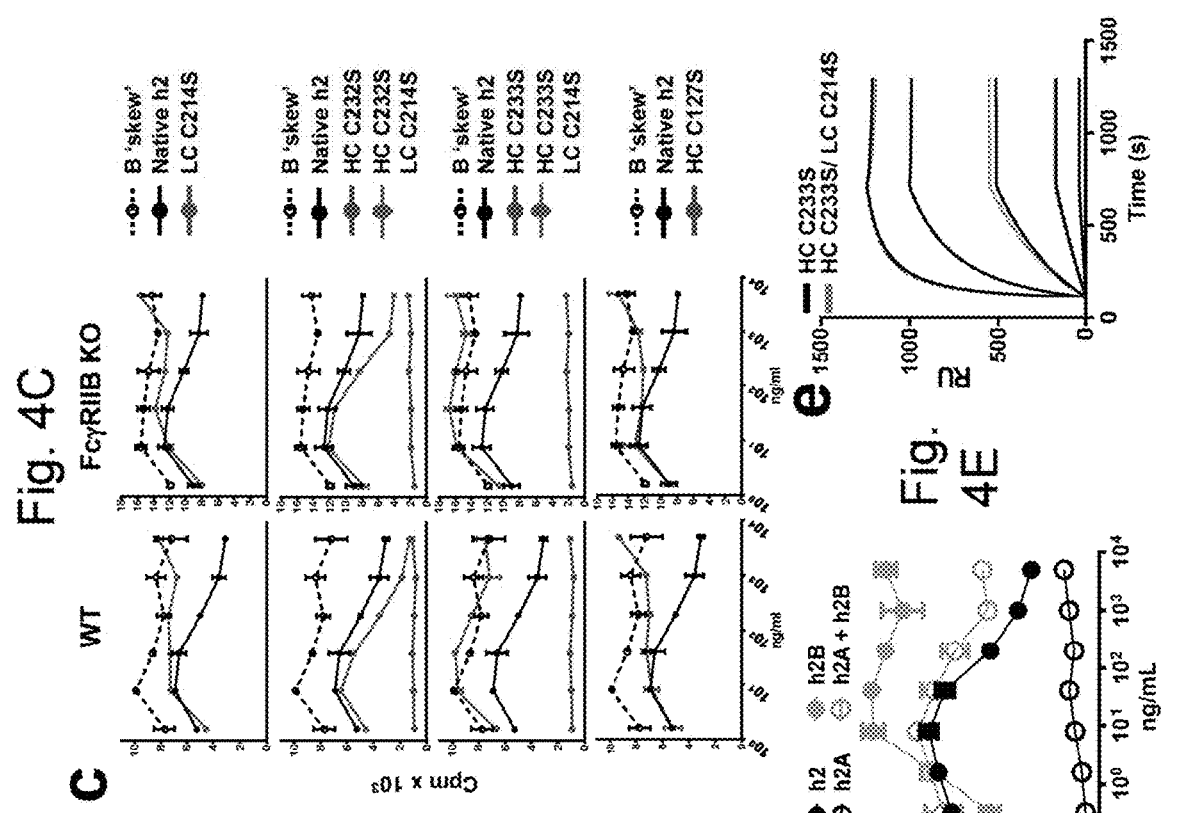
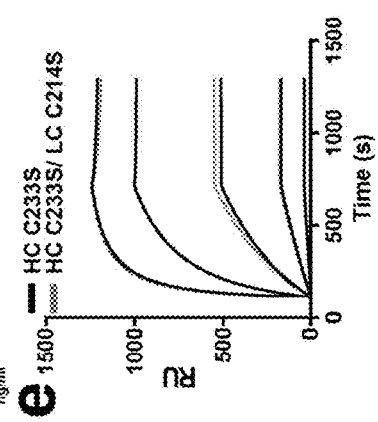
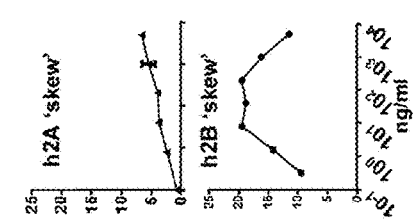
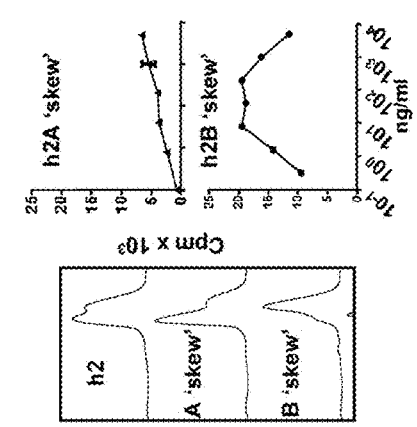
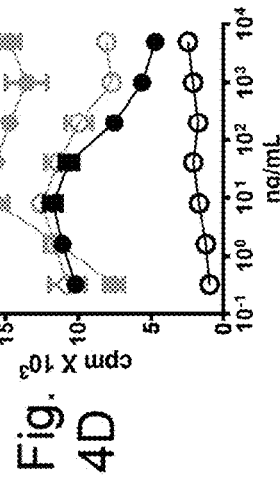
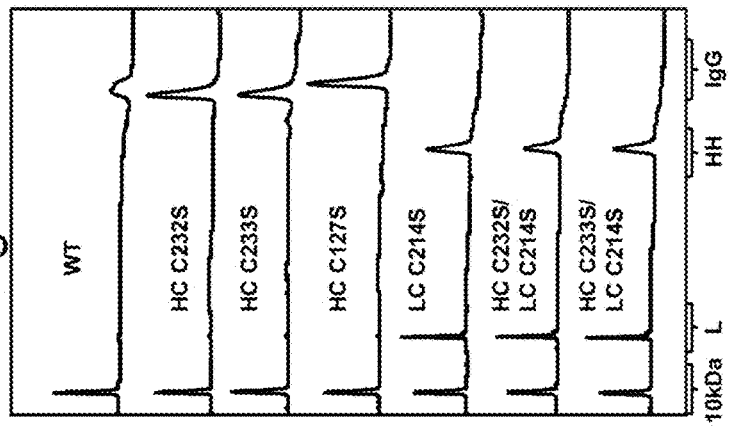

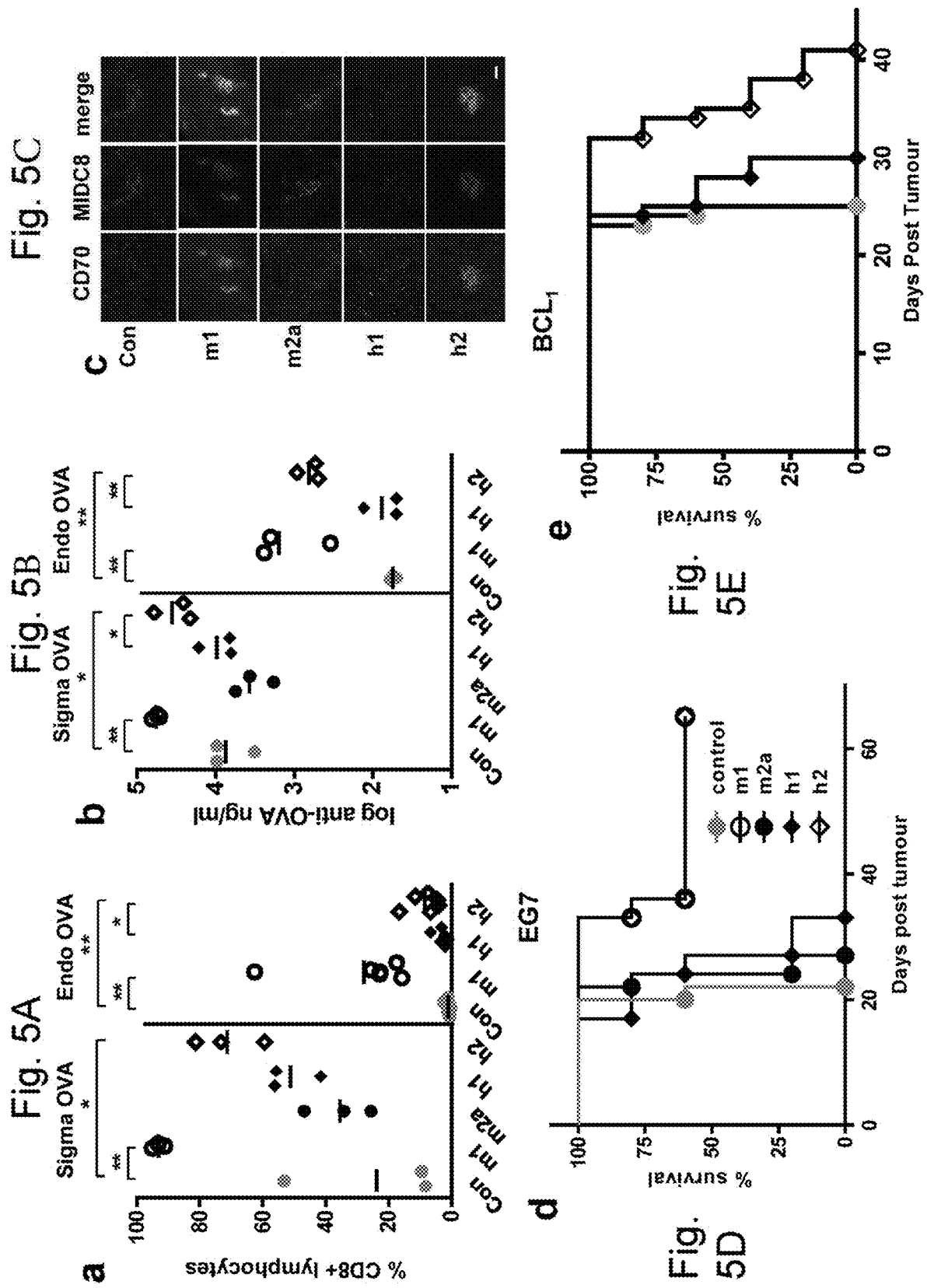

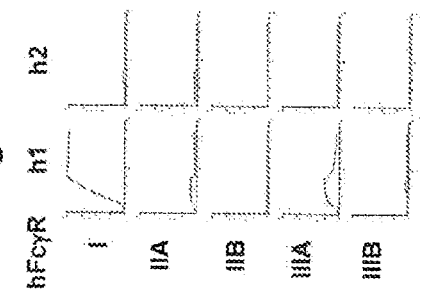
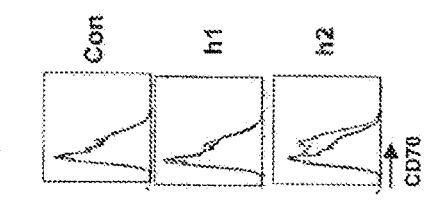
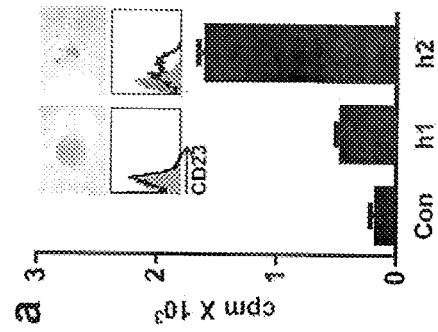
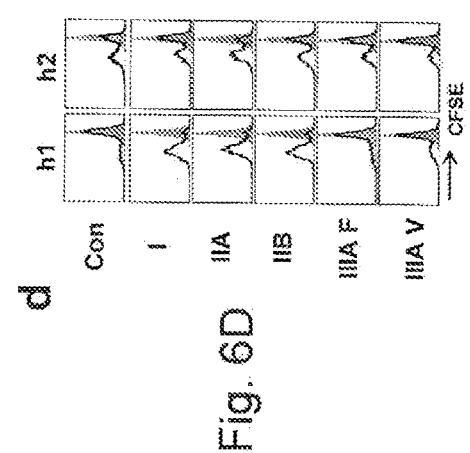
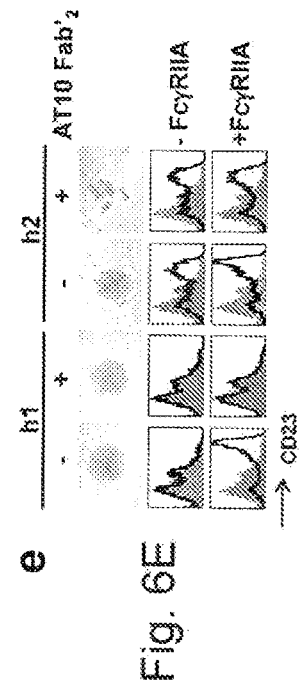

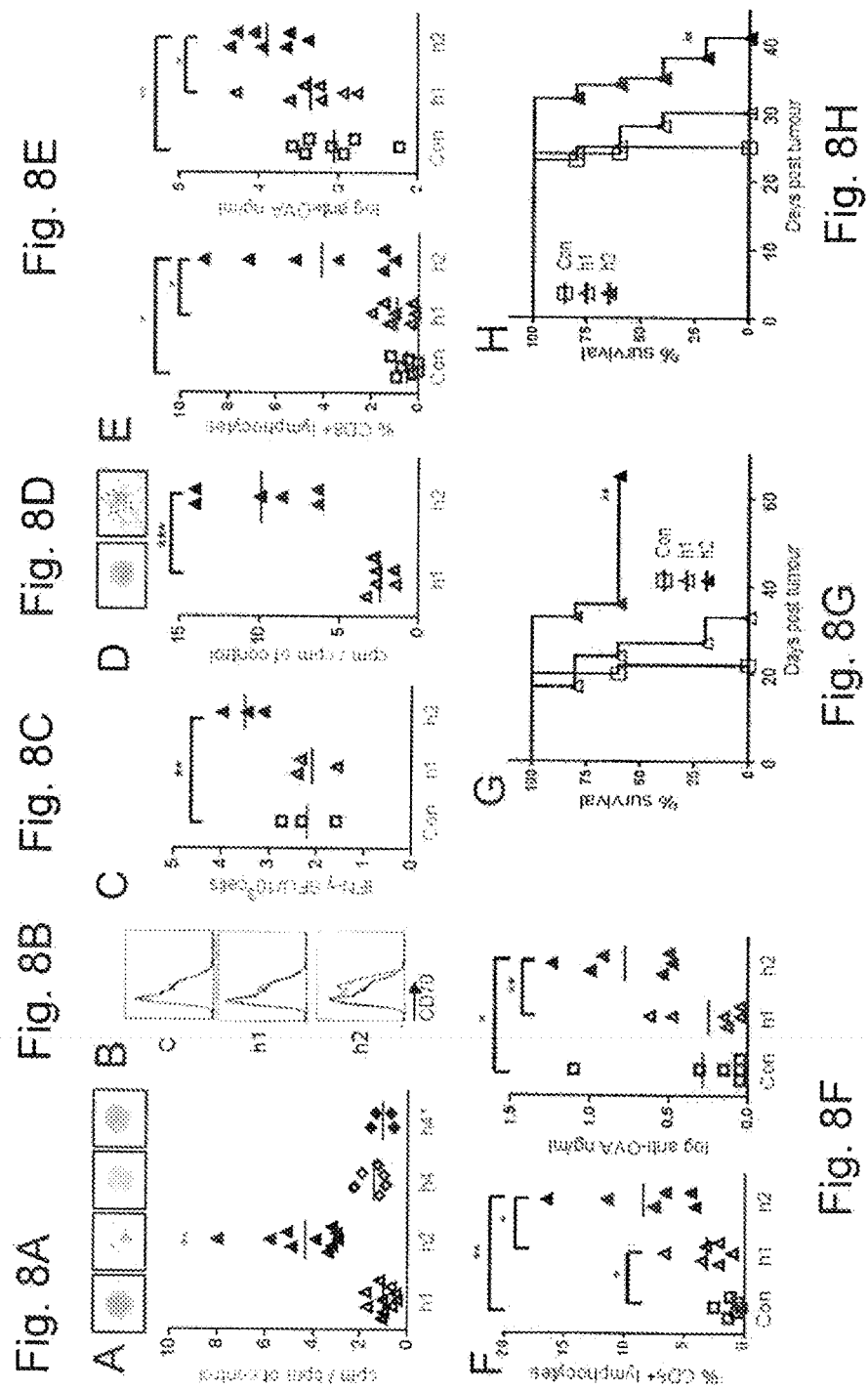
Figure 8A-H: Human isotypes and anti-CD40 activity.

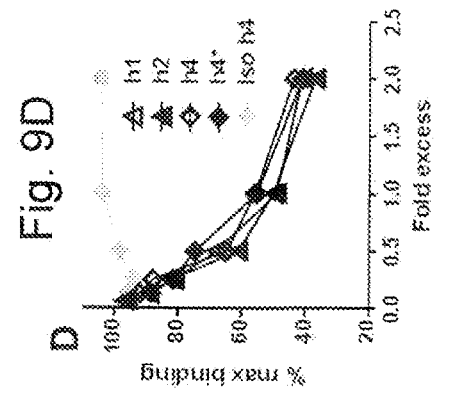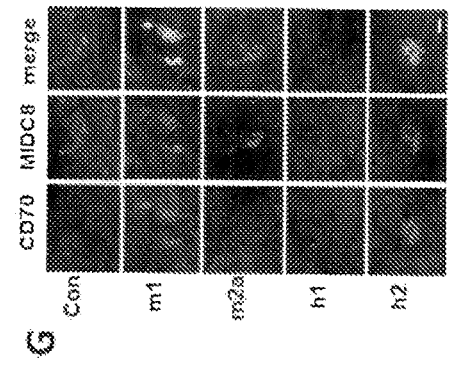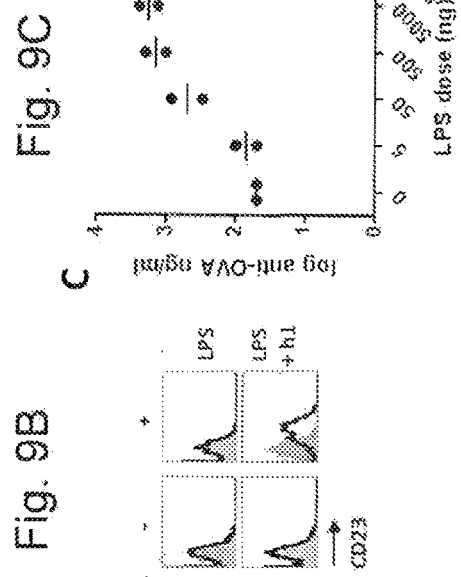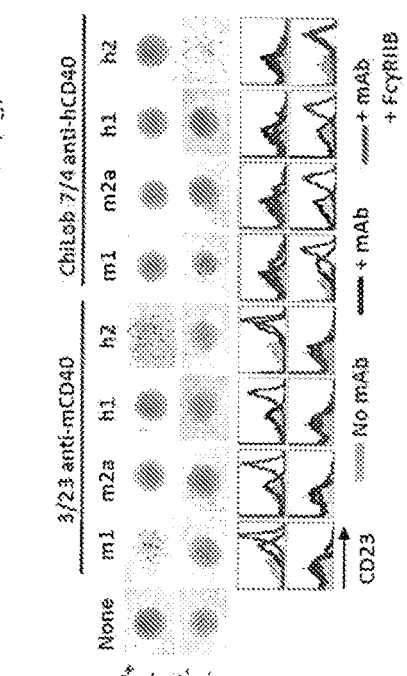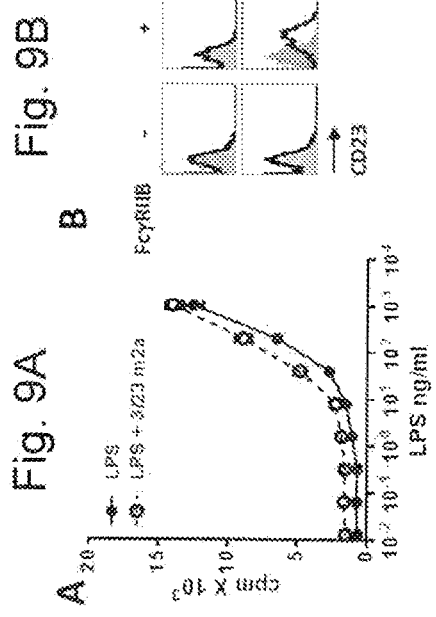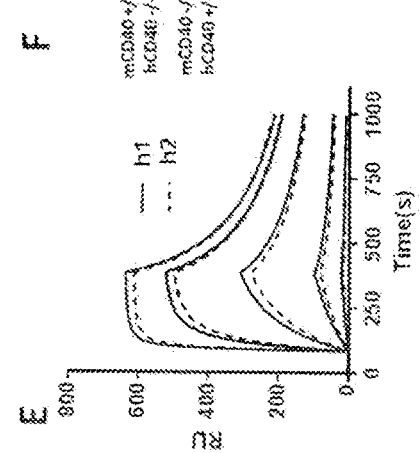
Figure 9A-G. Control experiments for isotype effects on anti-CD40 activity.

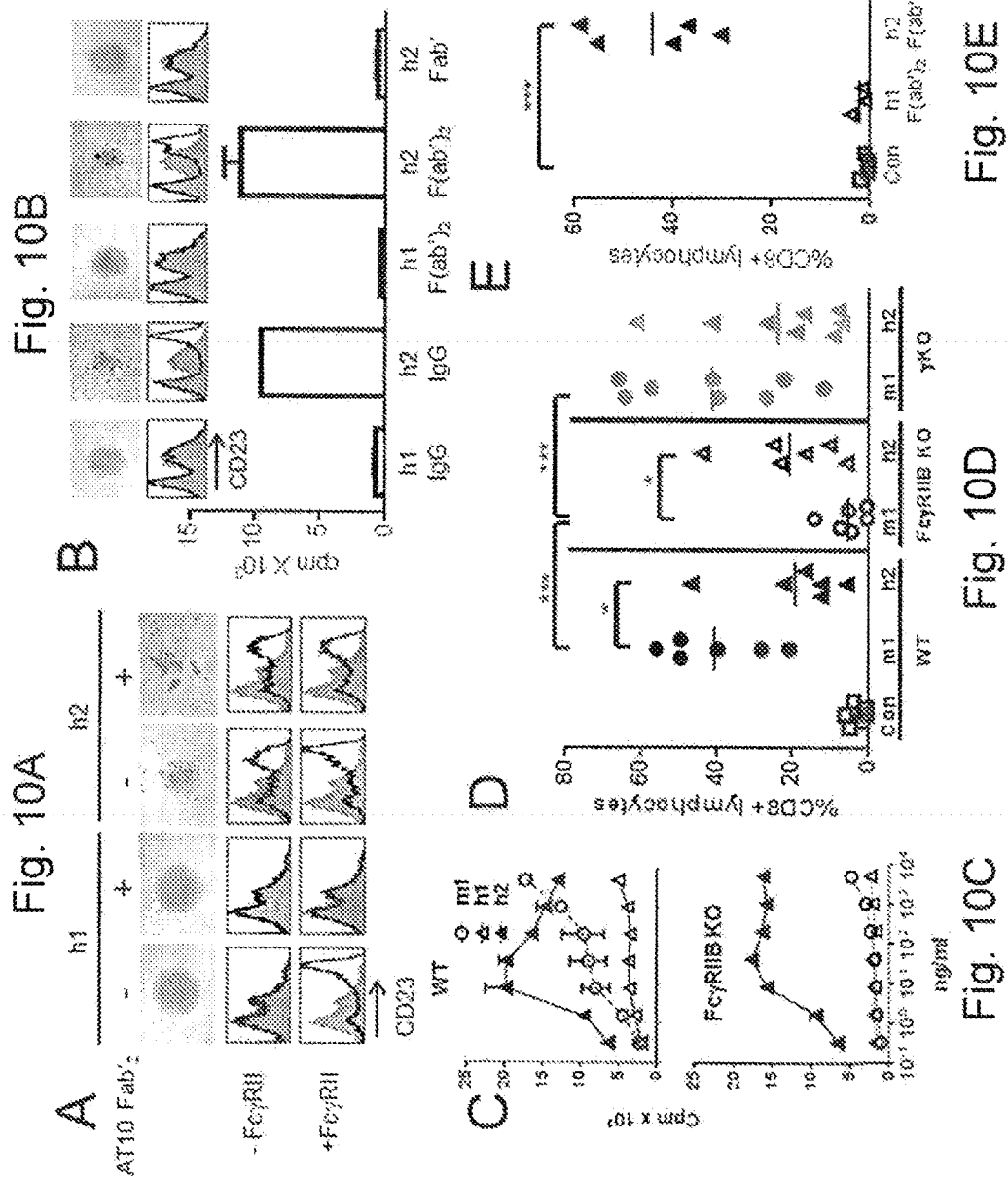
Figure 10A-E. FcgR-independent activity of human IgG2.

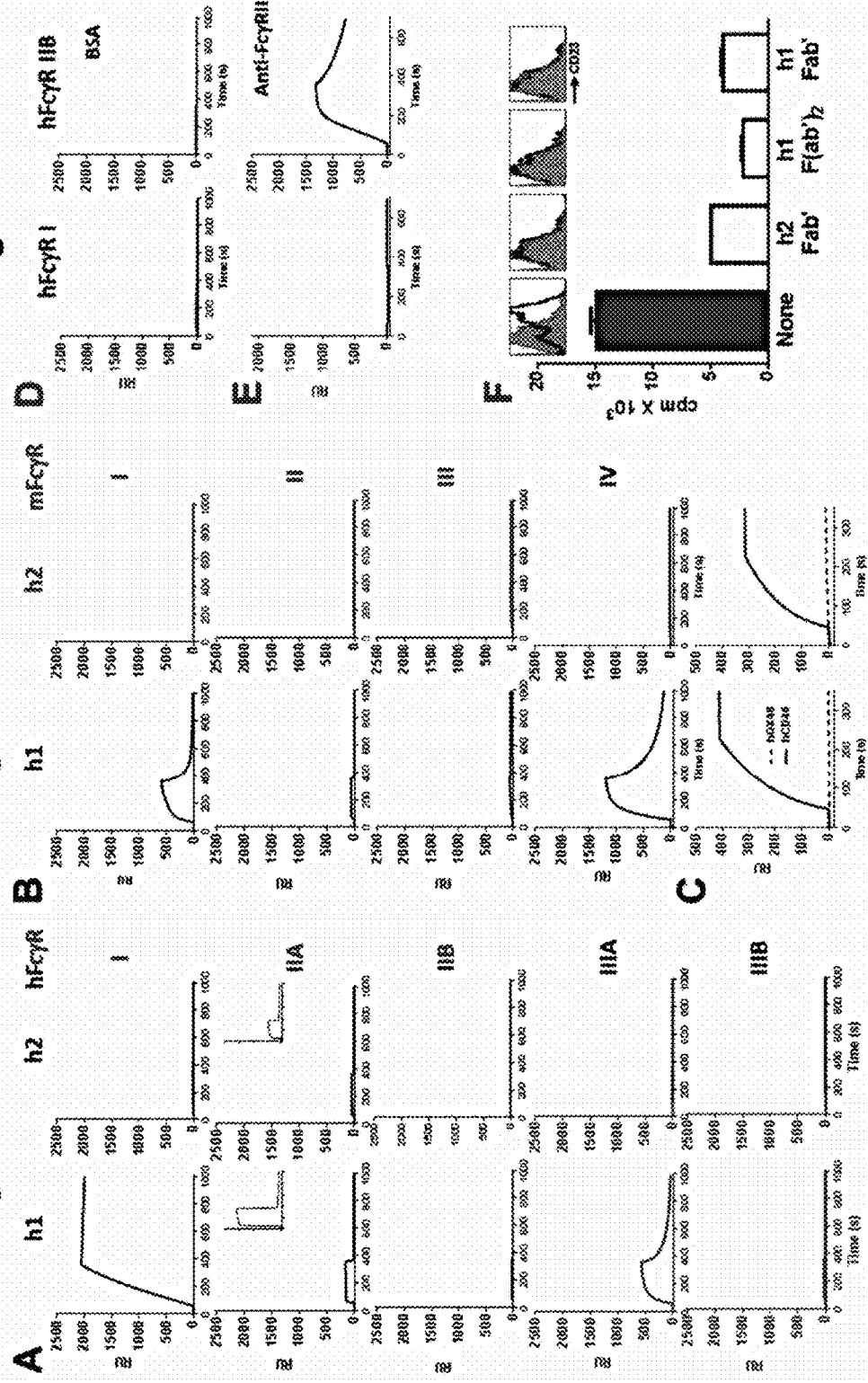
Figure 11A-F: ChiLob 7/4 h2 agonistic activity is FcgR independent.

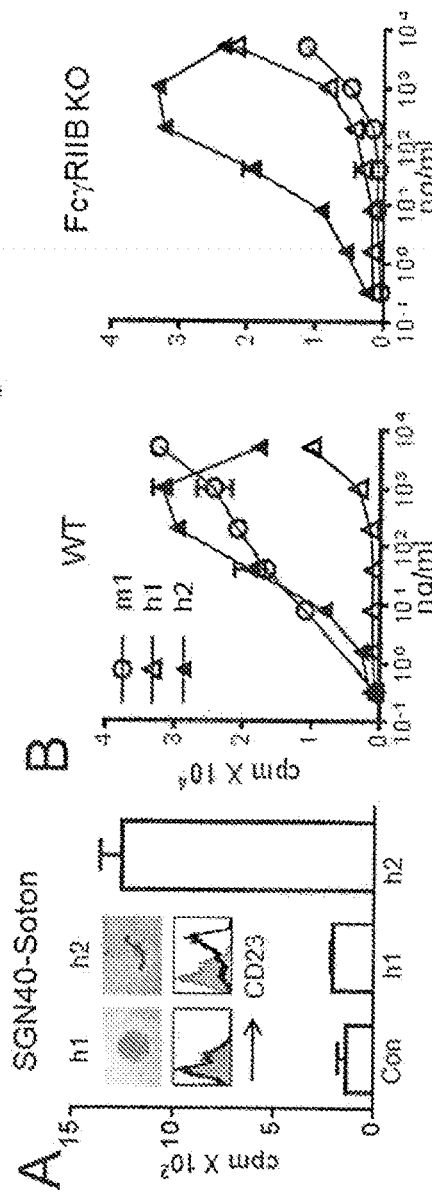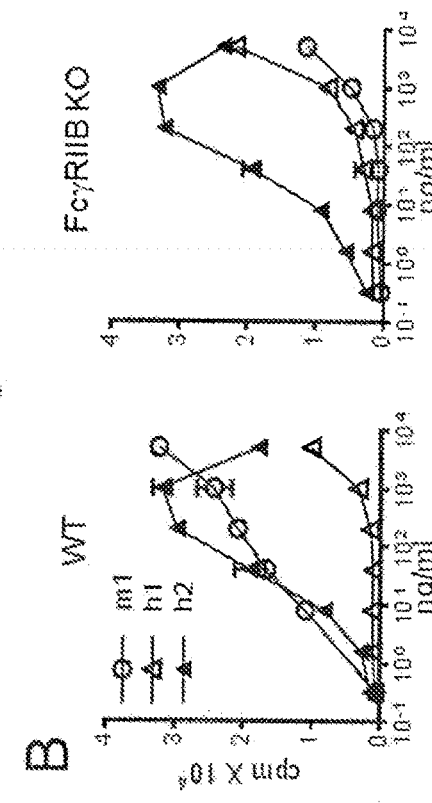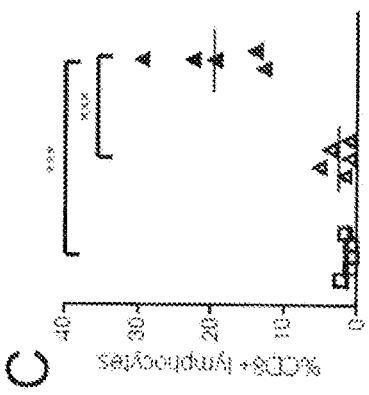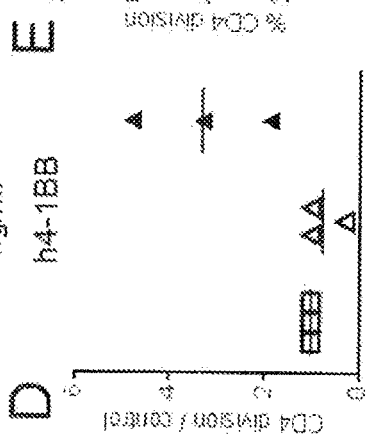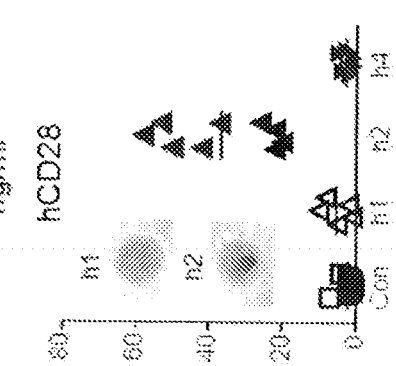
Figure 12A-E: Human IgG2 is agonistic for multiple receptor targets.

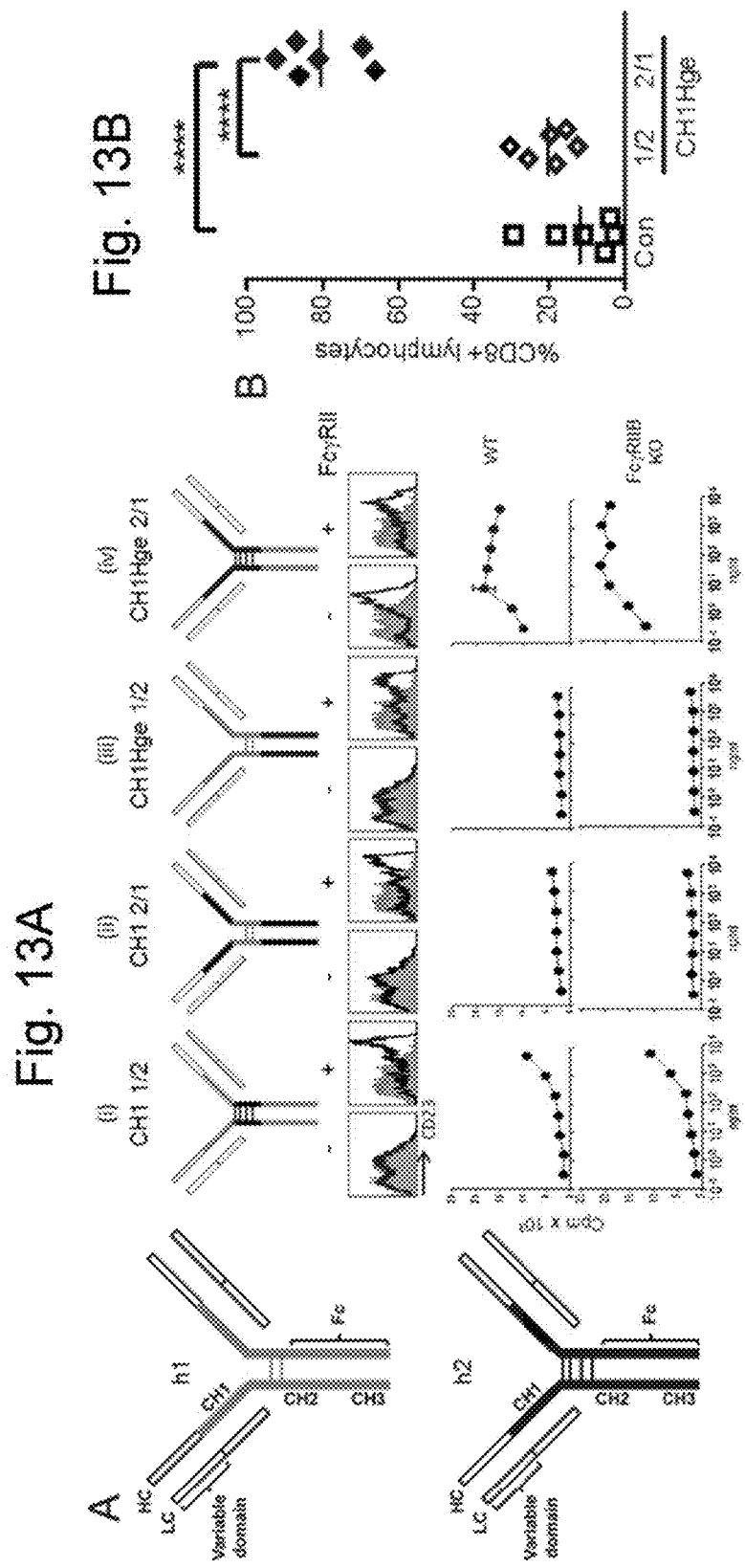
Figure 13A-B: The CH1 and hinge regions confer activity to ChiLob7/4 h2.

Figure 14: ChiLob 7/4 switch mutants bind similarly to CD40.

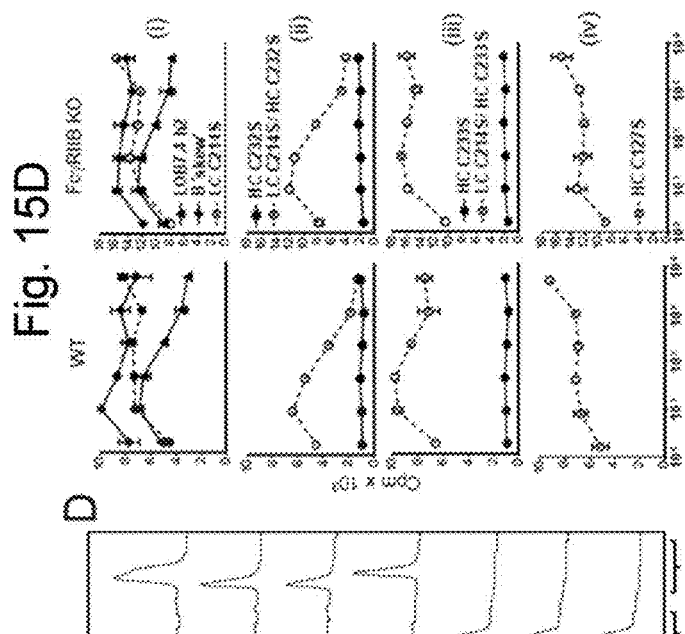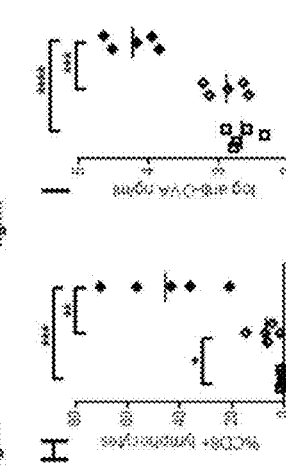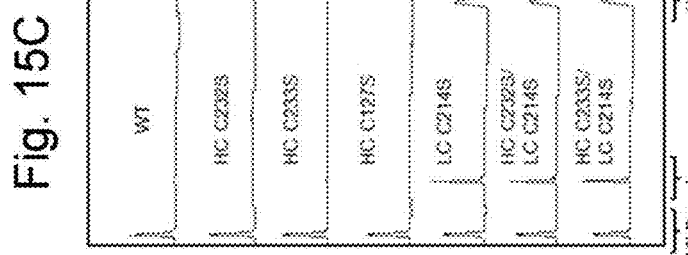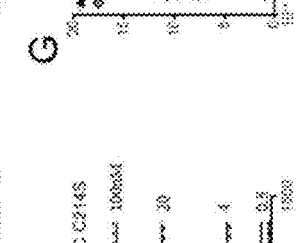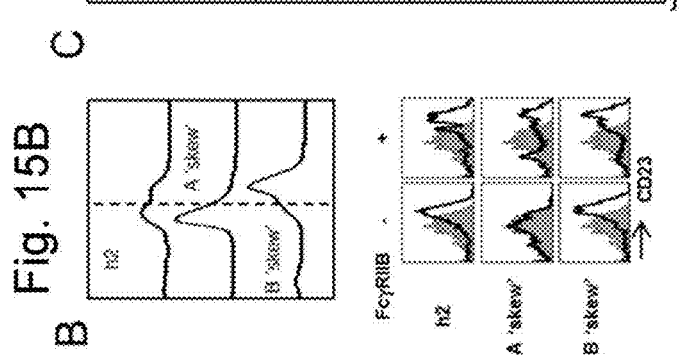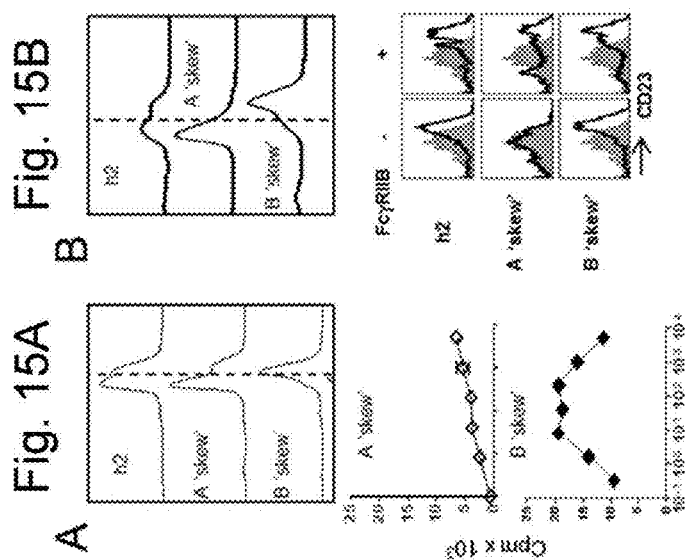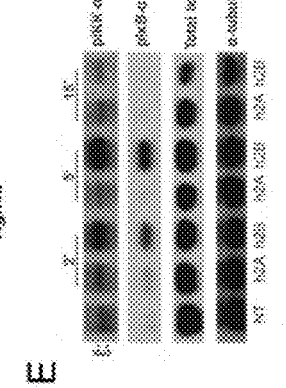
Figure 15: Mutagenesis generates a range of

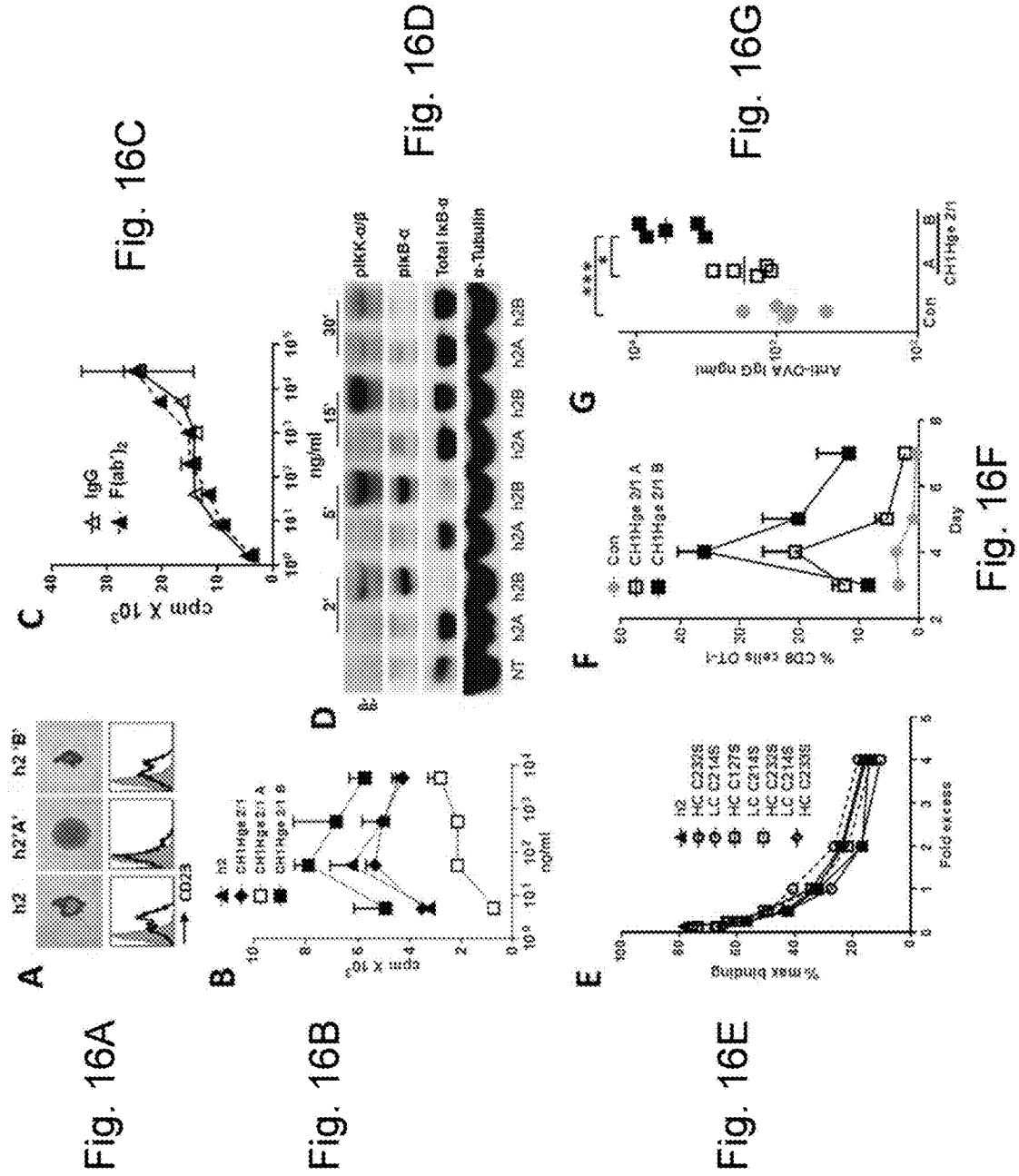
Figure 16A-G: Differential activity of ChiLob 7/4 h2A and h2B forms.

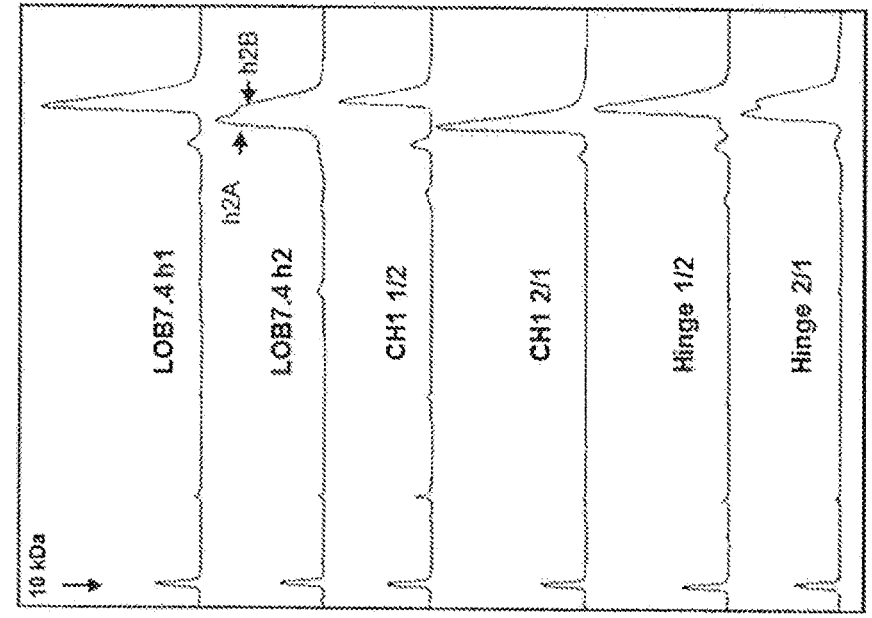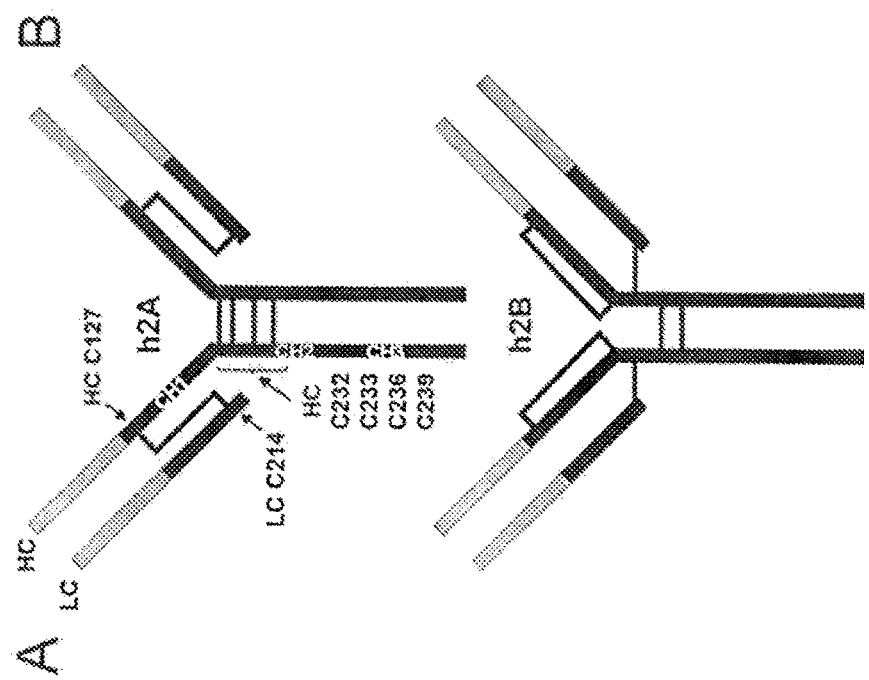
Figure 18: Disulfide shuffling in the human IgG2 hinge.

Mutagenesis can 'lock' h2 into h2A and h2B forms

Mutagenesis of h2 can produce agonists and antagonists

Mutagenesis of h2 can produce agonists and antagonists

Mutagenesis of h2 can produce agonists and antagonists

Mutagenesis of h2 can produce agonists and antagonists

Why is h2B agonistic and h2A antagonistic?

Immunostimulatory properties of anti-CD40 mAb

B cell assays of anti-CD40 activity

MODIFIED ANTIBODIES CONTAINING MODIFIED IGG2 DOMAINS WHICH ELICIT AGONIST OR ANTAGONISTIC PROPERTIES AND USE THEREOF

PRIORITY

This application is a U.S. National Phase application of International Application No. PCT/IB2015/052166, filed Mar. 24, 2015, which claims priority to GB Application No. 1405264.1, filed Mar. 24, 2014, and GB Application No. 1405275.7, filed on Mar. 25, 2014, each of which is incorporated herein by reference.

FIELD

The present application generally relates to the discovery that human IgG2 (h2) delivers unique FcγR-independent agonistic activity to anti-CD40 antibodies and antibodies to other immunostimulatory receptors, including 4-1BB and CD28; and potentially other B7/CD28 and TNF/TNFR family members, and further that the unique agonistic or conversely antagonistic activity of h2 is dependent upon the precise arrangement of hinge and $C_H 1$ disulfide bonds. Based thereon, the invention provides novel agonistic and antagonistic antibodies, and the use thereof in therapy, wherein the hinge region of IgG2 is mutagenized to 'lock' the antibody in either a more flexible 'h2A' or more compact 'h2B' conformation in order to respectively endow antagonistic and agonistic properties to the antibody.

BACKGROUND

Monoclonal antibodies (mAbs) are revolutionizing cancer treatment, reigniting the belief that the immune system can be harnessed to eradicate tumors (Sliwkowski et al., (2013); Hodi F S, et al. (2010); Wolchok J D, et al. (2013). Results with anti-CTLA-4 and anti-PD-1 mAbs have galvanized the view that T-cell immunity can provide long-lasting protection against aggressive and difficult to treat cancers, such as metastatic melanoma and non-small cell lung cancer. (Hodi F S, et al. (2010); Wolchok J D, et al. (2013); Topalian S L, et al. (2012). Different mAb agents mediate their effects in diverse ways and a precise understanding of their mechanisms of action is required to improve therapeutic efficacy. Moreover, the choice of mAb isotype is crucial due largely to differences in Fcγ receptor (FcγR) interactions that direct events downstream of antigen engagement (Nimmerjahn F & Ravetch J V (2012); White A L, et al. (2013).

Agents that work through deletion of their cellular targets, such as malignant B cells with anti-CD20 (Uchida J, et al. (2004)), or murine T regulatory cells with anti-CTLA4 and anti-GITR (Simpson T R, et al. (2013) Bulliard Y, et al. (2013). Mouse IgG2a (m2a) and human IgG1 (h1) are effective for this type of agent as they have a high activatory/inhibitory (A/I) FcγR binding ratio (Hamaguchi Y et al, The Journal of experimental medicine 203(3):743-753; Nimmerjahn F & Ravetch J V (2005)). In contrast, mAbs whose effects rely on agonistic receptor engagement, such as immunostimulatory anti-CD40 (Brahmer et al, (2012); Bruhns, et al., Blood 113, 3716-3725 or apoptosis promoting anti-death receptor (DR) 4, DR5 and Fas (Li F & Ravetch J V (2012); Wilson N S, et al. (2011). Xu Y, et al. (2003) appear to rely predominantly on crosslinking by the inhibitory FcγRIIB to deliver their activity (White A L, et al. (2011); Li F & Ravetch J V (2013), White et al. (2013)). For this type of agent mouse IgG1 (m1) is optimal in preclinical models as it has a low A/I ratio and engages FcγRIIB with sufficient affinity to mediate cross-linking (White et al., (2011); Li F & Ravetch J V (2011)) An agonistic anti-CD40 mAb in clinical trials, CP870, 893 (Vonderheide R H, et al. (2007)), is a human IgG2 (h2), which based on its isotype is not predicted to engage Fcγ R) (Bruhns P, et al. (2009) Two other less agonistic CD40 antibodies, ChiLOB7.4 and SGN40 are both h1 (Advani R, et al. (2009); Johnson et al., (2010)). In addition, a recent study demonstrated that h2 constant regions conferred increased stimulatory activity to a specific anti-human CD28 mAb, TGN1412 (Ball C, et al. (2012)).

Notwithstanding the foregoing, it was unclear prior to the present invention as to the optimal isotype which should be used in agonistic mAbs or fusion proteins which are to be used for human therapy. Particularly, there is little understanding as to how antibody isotype may affect the therapeutic properties of therapeutic antibodies, i.e., the agonistic or antagonistic properties thereof. The present invention addresses this need and provides improved agonistic (as well as antagonistic) antibodies and further provides means for the synthesis thereof. In an exemplary embodiment these antibodies and fusion proteins, e.g., those that target TNFR superfamily members are useful in therapeutic indications wherein either agonistic or antagonistic antibodies or fusion proteins are therapeutically desirable.

SUMMARY

The present invention provides an understanding concerning optimal antibody isotypes for producing antibodies possessing agonistic or antagonistic properties. More specifically the present invention provides antibodies comprising human IgG2 constant regions possessing specific mutations wherein, dependent on the specific mutations, these antibodies possess either agonistic or antagonistic properties.

The present invention in particular determines the immunomodulatory activity of human IgG isotypes using mAbs against a number of human co-stimulatory receptors (CD40, 4-1BB and CD28) and thereby show that human IgG2 (h2) imparts greater immunostimulatory activity to these agents than either h1 or human h4 and show that this activity does not depend upon differences in FcgR interaction but rather on the unique configuration of disulfide bonds in the h2 hinge and CH1 domains, which using mutagenesis may be manipulated in order to 'lock' the mAb into different configurations with contrasting levels of agonistic activity thereby providing for the development of homogeneous superagonistic therapeutic antibodies with defined levels of activity that are independent of FcgR expression levels in the local microenvironment.

The present invention further relates to the use of such antibodies and fusion proteins comprising human IgG2 constant regions possessing specific mutations as receptor agonists or receptor antagonists in the treatment or prophylaxis of diseases wherein such receptor agonists or receptor antagonists have therapeutic application. In exemplary embodiments the antibodies will specifically bind to TNF superfamily members such as CD40, LTα, LTβ, FASL CD30, CD27, OX40, TRAIL/APO-2L, 4-1BB, 4-1BBL, TNF, TNF-R, TRANCE, TRANCE-R, GITR or "glucocorticoid-induced TNF receptor", TWEAK, FN14, and the like; or to B7/CD28 family members such as B7.1 (CD80) (CD86), 87-DC (PD-L2 or CD273), B7-H1, B7-H2, B7-H3 (CD276), B7-H4 (VTCN1), B7-H5 (VISTA), B7-H6

(NCR3LG1), B7-H7 (HHLA2), PD-1 (CD279), PD-L3, CD28, CTLA-4 (CD152), ICOS(CD278), BTLA, NCR3, CD28H, and NKp30.

OBJECTS OF THE INVENTION

It is an object of the invention to provide novel immune agonists or antagonists, and more particularly superagonists.

It is a more specific object of the invention to provide novel immune agonists or antagonists comprising mutated IgG2 constant regions, wherein such mutations enhance the agonistic or antagonistic properties of such agonist or antagonist polypeptides, e.g., agonistic or antagonistic IgG2 antibodies or IgG2/IgG2 chimeric fusion proteins.

It is another specific object of the invention to provide modified agonistic or antagonistic antibodies which are not of the human IgG2 isotype, e.g., human IgG1, IgG3, IgG4, IgA, IgD, IgE or IgM antibodies, wherein the entire or substantially the entire hinge and $C_H1$ regions of hIgG2 and optionally the light chain constant region of hIgG2 are used to replace the corresponding light chain constant region, hinge and $C_H1$ domains or regions of the non-human IgG2 antibody, e.g., a human IgG1, IgG3, IgG4, IgA, IgD, IgE or IgM.

It is a more specific object of the invention to provide agonistic antibodies that specifically bind to a receptor or ligand expressed on human immune cells, wherein said antibody agonizes one or more biological activities elicited by said receptor or ligand, or biological activities elicited by the interaction of said ligand and receptor, and further wherein said agonistic antibody comprises at least the $C_H1$ and hinge regions of human IgG2 ("H2 regions"), wherein one or more cysteine residues of said IgG2 regions are removed or changed to a different amino acid residue in order to increase the agonistic properties of the resultant agonistic antibody relative to an otherwise identical antibody wherein said one or more cysteine residues are unchanged.

It is another specific object of the invention to provide modified antibodies that specifically bind to a receptor or ligand expressed on the surface of human cells, wherein said modified antibody agonizes one or more biological activities elicited by said receptor or ligand, or biological activities elicited by the interaction of said ligand and its corresponding receptor, wherein said antibody is other than a human IgG2 antibody, and further wherein the entire or substantially the entire hinge and $C_H1$ domains of said modified antibody, and optionally the light chain constant region, which modified antibody is other than a human IgG2, are replaced with the corresponding entire or substantially the entire hinge and $C_H1$ domains ("H2 regions" or "H2 domains", and optionally the light chain constant region of an hIgG2 antibody.

It is another specific object of the invention to provide modified antibodies as above-described selected from an hIgG1, hIgG3, hIgG4, IgA, IgD, IgE, or IgM, wherein the entire or substantially the entire hinge and $C_H1$ domains of said antibody have been replaced with the corresponding entire or substantially the entire hinge and $C_H1$ domains ("H2 regions" or "H2 domains") of hIgG2.

It is another specific object of the invention to provide modified antibodies as above-described wherein either or both of the heavy chain cysteine residue at position 127 and the light chain cysteine residue at position 214 (wherein numbering is according to Kabat) are deleted or changed to a different amino acid residue, resulting in an increase in the agonistic properties of the resultant modified antibody relative to an otherwise identical antibody wherein either or both of said cysteine residues are unchanged.

It is another specific object of the invention to provide modified antibodies as above-described wherein the only cysteine residue in the H2 regions of said modified antibody which is mutated or deleted is the cysteine at position 214 in the light chain and said modified antibody comprises either (i) a heavy chain wherein no cysteine residues are deleted or modified in the H2 regions or (ii) one or more of the cysteine residues at positions 127, 232 or 233 of the heavy chain are deleted or mutated, resulting in a modified antibody wherein the agonistic properties of the resultant modified antibody are increased relative to an otherwise identical antibody lacking said deletions or modifications.

It is another specific object of the invention to provide modified antibodies as above-described which comprise modified hIgG1 or hIgG3.

It is another specific object of the invention to provide modified antibodies as above-described which specifically binds to human immune cells.

It is another specific object of the invention to provide modified antibodies as above-described which bind to dendritic cells, mast cells, monocytes, macrophages, NK cells, B lymphocytes, T lymphocytes or any combination of the foregoing.

It is another specific object of the invention to provide modified antibodies as above-described wherein absent said modifications the antibody lacks agonistic activity.

It is another specific object of the invention to provide modified antibodies as above-described wherein absent said modifications the antibody possesses no more than 10%, of the agonistic activity of the modified antibody, wherein agonistic activity is detected in an accepted assay for quantifying agonism.

It is another specific object of the invention to provide modified antibodies as above-described wherein absent said modifications the antibody possesses no more than 20%, of the agonistic activity of the modified antibody, wherein agonistic activity is detected in an accepted assay for quantifying agonism.

It is another specific object of the invention to provide modified antibodies as above-described, wherein absent said modifications the antibody possesses no more than 30%, of the agonistic activity of the modified antibody, wherein agonistic activity is detected in an accepted assay for quantifying agonism.

It is another specific object of the invention to provide modified antibodies as above-described, wherein absent said modifications the antibody possesses no more than 40%, of the agonistic activity of the modified antibody, wherein agonistic activity is detected in an accepted assay for quantifying agonism.

It is another specific object of the invention to provide modified antibodies as above-described, wherein absent said modifications the antibody possesses no more than 50%, of the agonistic activity of the modified antibody, wherein agonistic activity is detected in an accepted assay for quantifying agonism.

It is another specific object of the invention to provide modified antibodies as above-described wherein absent said modifications the antibody possesses no more than 50-80%, of the agonistic activity of the modified antibody, wherein agonistic activity is detected in an accepted assay for quantifying agonism.

It is another specific object of the invention to provide modified antibodies as above-described wherein said antibody agonizes one or more biological activities elicited by a human receptor or ligand, or biological activities elicited by the interaction of said ligand and its corresponding receptor, and further wherein said modified antibody comprises at least the light chain constant region and the $C_H1$ and hinge of heavy chain regions of hIgG2 ("H2 regions"), wherein either or both of the cysteine residues selected from the heavy chain cysteine residue at position 127 and the light chain cysteine residue at position 214 are removed or changed to a different amino acid residue, resulting in an increase in the agonistic properties of the resultant agonistic antibody relative to an otherwise identical antibody wherein both of said cysteine residues are unchanged (wherein amino acid numbering is according to Kabat).

It is another specific object of the invention to provide modified antibodies as above-described wherein the cysteine residue of the light chain of said modified antibody at position 214 is deleted or mutated and the modified antibody comprises either (i) a heavy chain wherein no cysteine residues within the H2 regions are deleted or mutated or (ii) said modified antibody comprises a heavy chain wherein at least one of the cysteine residues at positions 127, 232 or 233 are deleted or mutated.

It is another specific object of the invention to provide modified antibodies as above-described wherein no cysteine residues within the H2 regions of the heavy chain are deleted or mutated.

It is another specific object of the invention to provide modified antibodies as above-described wherein at least one of the cysteine residues at positions 127, 232 or 233 in the heavy chain are deleted or mutated.

It is another specific object of the invention to provide modified antibodies as above-described wherein any combination of one or two of the cysteine residues at positions 127, 232 or 233 in the heavy chain are deleted or mutated.

It is another specific object of the invention to provide modified antibodies as above-described wherein the H2 regions of the modified antibody are in the h2B conformation.

It is another specific object of the invention to provide modified antibodies as above-described wherein the only cysteine residue in the hIgG2 heavy chain H2 regions which is removed, modified or substituted with another amino acid residue comprises the heavy chain cysteine residue at position 127.

It is another specific object of the invention to provide modified antibodies as above-described wherein no cysteine residues in the light chain region is removed, modified or substituted with another amino acid residue.

It is another specific object of the invention to provide modified antibodies as above-described wherein the only cysteine residue in the hIG2 light chain constant region which is removed, modified or substituted with another amino acid residue comprises the light chain cysteine residue at position 214.

It is another specific object of the invention to provide modified antibodies as above-described wherein the only cysteine residue in the hIgG2 H2 regions which is removed, modified or substituted with another amino acid residue is selected from the heavy chain cysteine residue at position 127 and the light chain cysteine residue at position 214.

It is another specific object of the invention to provide modified antibodies as above-described which comprises a serine substituted for the cysteine at position 214 in the light chain and/or a serine residue substituted for the cysteine residue at position 127 in the heavy chain.

It is another specific object of the invention to provide modified antibodies as above-described of the hIgG1 or hIgG3 or hIgG4 isotype, wherein the entire hinge and $C_H1$ regions of said hIgG1, hIgG3 or hIgG4 are replaced with the corresponding hinge and $C_H1$ regions of hIgG2.

It is another specific object of the invention to provide modified antibodies as above-described which is a hIgG1.

It is another specific object of the invention to provide modified antibodies as above-described which comprises one or more modified cysteine residues within the light or heavy chain H2 regions.

It is another specific object of the invention to provide modified antibodies as above-described which comprises additional modifications outside the H2 regions which do not affect or appreciably affect (no more than 10% change) the agonistic properties of the modified antibody.

It is another specific object of the invention to provide modified antibodies as above-described, which specifically binds to a TNF or B7 superfamily member expressed on the surface of human cells, e.g., CD40, 4-1BB or CD28.

It is another specific object of the invention to provide modified antibodies as above-described which specifically binds to a receptor or ligand expressed on at least one type of human immune cell.

It is another specific object of the invention to provide modified antibodies as above-described which bind immune cells selected from T lymphocytes, B lymphocytes, monocytes, mast cells, macrophages, NK cells, and dendritic cells or combinations thereof.

It is another specific object of the invention to provide modified antibodies as above-described which comprises the entire human IgG2 CH1 and hinge regions.

It is another specific object of the invention to provide modified antibodies as above-described which lacks the human IgG2 Fc region.

It is another specific object of the invention to provide modified antibodies as above-described wherein the agonistic properties of said antibody or fusion are FcγR independent.

It is another specific object of the invention to provide modified antibodies as above-described, wherein the antibody specifically binds to a TNFR superfamily member selected from CD40, LTα, LTβ, CD30, CD27, OX40, 4-1BB, TNF-R, TRANCE-R, GITR or "glucocorticoid-induced TNF receptor", TWEAK, and FN14 or to a B7/CD28 family member selected from B7.1 (CD80), B7.2 (CD86), B7-H1, B7-H2, B7-H3 (CD276), B7-H4 (VTCN1), B7-H5 (VISTA), B7-H6 (NCR3LG1), B7-H7 (HHLA2), PD-1 (CD279), CD28, CTLA-4 (CD152), ICOS(CD278), BTLA, NCR3, CD28H, and NKp30.

It is another specific object of the invention to provide modified antibodies as above-described which bind a TNFR member selected from 4-1BB, CD40, or CD27 or the B7/CD28 family member is CTLA-4 or CD28.

It is another specific object of the invention to provide modified antibodies as above-described which comprises the variable region of LOB7.4.

It is another specific object of the invention to provide pharmaceutical compositions containing modified antibodies as above-described comprising a pharmaceutically effective amount of such modified antibody.

It is another specific object of the invention to provide the use of such antibodies or such compositions with other immune agonists.

It is another specific object of the invention to provide the use of modified antibodies as above-described in therapeutic methods which comprises the administration of at least one modified antibody or fusion protein containing same, said method comprising the administration of an effective amount of at least one modified antibody or fusion protein or composition containing according to the invention. In preferred embodiments, the treated condition is selected from cancer, infection, allergy, autoimmunity, transplant, GVHD, or inflammation.

It is another specific object of the invention to provide modified antibodies that specifically binds to a receptor or ligand expressed on the surface of human cells, wherein said modified antibody antagonizes one or more biological activities elicited by said receptor or ligand, or biological activities elicited by the interaction of said ligand and its corresponding receptor, wherein said antibody is other than a human IgG2 antibody, and further wherein the entire or substantially the entire hinge and $C_H1$ domains of said modified antibody, which is other than a human IgG2, and optionally the light chain constant region, are replaced with the corresponding entire or substantially the entire hinge and $C_H1$ domains and light chain constant region ("H2 regions" or "H2 domains") of an hIgG2 antibody, wherein one or more of the cysteine residues within the H2 regions are optionally modified, said modifications resulting in an increase in the antagonistic properties of the resultant modified antibody.

It is another specific object of the invention to provide modified antagonistic antibodies as above-described selected from an hIgG1, hIgG3, hIgG4, IgA, IgD, IgE, or IgM, wherein the entire or substantially the entire hinge and $C_H1$ domains, and optionally the light chain constant regions of said antibody have been replaced with the corresponding entire or substantially the entire hinge and $C_H1$ domains and light chain constant regions ("H2 regions" or "H2 domains") of hIgG2.

It is another specific object of the invention to provide modified antagonistic antibodies as above-described wherein at least one cysteine residue of said IgG2 H2 regions selected from the cysteine residues at positions 232, 233, 236 and 239 are removed or changed to a different amino acid residue, resulting in an increase in the antagonistic properties of the resultant modified antibody relative to an otherwise identical antibody wherein said one or more cysteine residues are unchanged.

It is another specific object of the invention to provide modified antagonistic antibodies as above-described wherein the cysteine at residue 214 in the light chain and the cysteine at residue 127 in the heavy chain of the modified antibody are not deleted, modified or substituted with another amino acid residue.

It is another specific object of the invention to provide modified antagonistic antibodies as above-described wherein the cysteine modifications within the H2 regions of the antibody selectively favor or result in the association of the heavy and light chains of the modified antibody via the cysteine at position 214 in the light chain and the cysteine at position 127 in the heavy chain.

It is another specific object of the invention to provide modified antagonistic antibodies as above-described wherein the H2 regions of the modified antibody are in the h2A conformation.

It is another specific object of the invention to provide modified antagonistic antibodies as above-described wherein at least one of the cysteine residues in the H2 regions other than C214 and C127 are changed to a serine residue.

It is another specific object of the invention to provide modified antagonistic antibodies as above-described which comprise a serine substituted for the cysteine at position 232 in the heavy chain.

It is another specific object of the invention to provide modified antagonistic antibodies as above-described which comprise a serine substituted for the cysteine at position 233 in the heavy chain.

It is another specific object of the invention to provide modified antagonistic antibodies as above-described which comprise a modified hIgG1 or hIgG3.

It is another specific object of the invention to provide modified antagonistic antibodies as above-described which specifically bind to human immune cells.

It is another specific object of the invention to provide modified antagonistic antibodies as above-described which bind immune cells including at least one of dendritic cells, mast cells, monocytes, macrophages, NK cells, B lymphocytes, T lymphocytes or any combination of the foregoing.

It is another specific object of the invention to provide modified antagonistic antibodies as above-described wherein absent said modifications the antibody lacks antagonistic activity.

It is another specific object of the invention to provide modified antagonistic antibodies as above-described wherein absent said modifications the antibody possesses no more than 10%, of the antagonistic activity of the modified antibody, wherein antagonistic activity is detected in an accepted assay for quantifying antagonism.

It is another specific object of the invention to provide modified antagonistic antibodies as above-described wherein absent said modifications the antibody possesses no more than 20%, of the antagonistic activity of the modified antibody, wherein antagonistic activity is detected in an accepted assay for quantifying antagonism.

It is another specific object of the invention to provide modified antagonistic antibodies as above-described wherein absent said modifications the antibody possesses no more than 30%, of the antagonistic activity of the modified antibody, wherein antagonistic activity is detected in an accepted assay for quantifying antagonism.

It is another specific object of the invention to provide modified antagonistic antibodies as above-described wherein absent said modifications the antibody possesses no more than 40%, of the antagonistic activity of the modified antibody, wherein antagonistic activity is detected in an accepted assay for quantifying antagonism.

It is another specific object of the invention to provide modified antagonistic antibodies as above-described wherein absent said modifications the antibody possesses no more than 50%, of the antagonistic activity of the modified antibody, wherein antagonistic activity is detected in an accepted assay for quantifying antagonism.

It is another specific object of the invention to provide modified antagonistic antibodies as above-described that specifically binds to a receptor or ligand expressed on human cells, wherein said antibody antagonizes one or more biological activities elicited by said receptor or ligand, or biological activities elicited by the interaction of said ligand and its corresponding receptor, and further wherein said antagonistic antibody comprises at least the $C_H1$ and hinge heavy and light chain constant regions of human IgG2 ("H2 regions"), wherein at least one cysteine residue of said IgG2 H2 regions selected from the cysteine residues at positions 232, 233, 236 and 239 are removed or changed to a different amino acid residue, resulting in an increase in the antagonistic properties of the resultant antagonistic antibody relative to an otherwise identical antibody wherein said one or more cysteine residues are unchanged.

It is another specific object of the invention to provide modified antagonistic antibodies as above-described wherein the cysteine residues at position 214 in the light chain and position 127 in the heavy chain are not deleted, modified or substituted with another amino acid.

It is another specific object of the invention to provide modified antagonistic antibodies as above-described wherein one or more cysteine or other amino acid residues in the hIgG2 H2 regions are removed, modified or substituted with another amino acid residue resulting in the H2 regions being in the h2A conformation.

It is another specific object of the invention to provide modified antagonistic antibodies as above-described wherein at least one of said cysteine residues in the hIgG2 H2 regions are changed to a serine residue.

It is another specific object of the invention to provide modified antagonistic antibodies as above-described which comprise a serine substituted for the cysteine at position 232 in the heavy chain.

It is another specific object of the invention to provide modified antagonistic antibodies as above-described which comprise a serine substituted for the cysteine at position 233 in the heavy chain.

It is another specific object of the invention to provide modified antagonistic antibodies as above-described which specifically bind to a TNF or TNFR superfamily member or B7 family member expressed on the surface of human cells.

It is another specific object of the invention to provide modified antagonistic antibodies as above-described which specifically binds to at least one type of human immune cell.

It is another specific object of the invention to provide modified antagonistic antibodies as above-described which specifically binds to a receptor or ligand expressed on T, B, mast, macrophage, monocyte, NK, or dendritic cells.

It is another specific object of the invention to provide modified antagonistic antibodies as above-described which comprises the entire human IgG2 constant heavy and light chain constant regions.

It is another specific object of the invention to provide modified antagonistic antibodies as above-described which lacks a human IgG2 Fc region.

It is another specific object of the invention to provide modified antagonistic antibodies as above-described wherein the antagonistic properties of said antibody are FcγR independent.

It is another specific object of the invention to provide modified antagonistic antibodies as above-described wherein the antibody specifically binds to a TNF/R superfamily member selected from CD40, CD40L (CD154), LTα, LTβ, FASL (CD178), CD30, CD30L (CD153), CD27, CD27L (CD70), OX40, OX40L, TRAIL/APO-2L, 4-1BB, 4-1BBL, TNF, TNF-R, TRANCE, TRANCE-R, GITR or "glucocorticoid-induced TNF receptor", TWEAK, and FN14.

It is another specific object of the invention to provide modified antagonistic antibodies as above-described wherein the TNF/R or B7 family member is 4-1BB, 4-1BBL, CD40, CD40L, CD27, CD28, B7.1, B7.2, or CD70.

It is another specific object of the invention to provide pharmaceutical compositions modified antagonistic antibodies as above-described comprising an effective amount of a modified antibody or fusion protein containing according to the invention.

It is another specific object of the invention to provide pharmaceutical compositions modified antagonistic antibodies as above-described or the use thereof which may which comprise another immune antagonist or other active agent.

It is another specific object of the invention to provide the use of modified antagonistic antibodies as above-described in therapeutic methods comprising the administration of at least one antagonistic antibody or fusion protein or composition containing, according to the invention, wherein such conditions preferably may include a cancer, allergy, infectious disease, autoimmunity, transplant, GVHD, or an inflammatory condition.

It is another specific object of the invention to provide modified antagonistic antibodies as above-described or the use thereof which comprises administration of an antibody comprising the variable region of LOB7.4 or of another antibody specific to CD40, 4-1BB, or CD28, e.g., which may be used to treat conditions such as cancer, infection, allergy, autoimmunity or inflammation.

It is another specific object of the invention to provide novel IgG2 agonistic antibodies or fusion proteins containing which comprise the entire human IgG2 constant regions, which are modified in the hinge region to alter disulfide shuffling.

It is another specific object of the invention to provide novel IgG2 agonistic antibodies or fusion proteins containing which do not contain the human IgG2 Fc or another Fc region.

It is another specific object of the invention to provide novel antagonistic or agonistic antibodies, wherein the entire or substantially the entire hinge and $C_H1$ regions of human IgG2 and optionally the light chain constant region of hIgG2 are used to replace the same domains or regions of human IgG1, IgG3 IgG4, IgA or IgM, optionally wherein said introduced hIgG2 hinge and/or hIgG2 $C_H1$ region and light chain constant region may comprise one or more mutations that enhance the agonistic or antagonistic properties of the resultant modified antibody.

It is another specific object of the invention to provide novel agonistic or antagonistic antibodies wherein the agonistic properties of said antibody or fusion are FcγR independent.

It is another specific object of the invention to provide novel agonistic or antagonistic antibodies wherein the antibody specifically binds to a TNFR superfamily member selected from CD40, LTα, LTβ, CD30, CD27, OX40, 4-1BB, TNF, TNF-R, TRANCE-R, GITR or "glucocorticoid-induced TNF receptor", TWEAK, and FN14, and the use thereof in human therapy.

BRIEF DESCRIPTION OF THE FIGURES

FIG. 1(a)-(f) contain the results of experiments showing that human IgG2 imparts FcγR independent agonistic activity to the anti-hCD40 mAb, LOB7.4.

FIG. 2(a)-(c) contain the results of experiments showing that human IgG2 imparts FcγR-independent activity to another anti-TNFRSF mAb.

FIG. 4(a)-(e) contain the results of experiments showing the agonistic activity of LOB7.4 h2 is dependent upon its ability to adopt its h2B conformation.

FIG. 5 (a)-(e) contains experiments showing the isotype dependence of the anti-mouse CD40 mAb, 3/23.

FIG. 6 (a)-(e) contain the results of experiments demonstrating that LOB7.4 human IgG2 is more active than human IgG1 on human cells and is independent of FcγR interaction.

FIG. 8 (a)-(h) contain experiments showing the effects of different human isotypes on anti-CD40 activity.

FIG. 9 (a)-(g) contains control experiments which further validate the isotype effects on anti-CD40 activity of experiments in FIG. 8.

FIG. 10 (a)-(e) contains experimental data showing the FcγR-independent activity of human IgG2.

FIG. 11 (a)-(f) contain further experimental data validating that ChiLob 7/4 h2 agonistic activity is FcγR-independent.

FIG. 12 (a)-(e) contain data showing the antagonistic effect of human IgG2 against multiple receptor targets.

FIGS. 13 (a) and (b) contain experiments showing that CH1 and hinge regions confer activity to ChiLob7/4 h2.

FIG. 15 (a)-(i) summarize the results of mutagenesis experiments showing that mutagenesis generates a range of ChiLob 7/4 h2 agonistic forms.

FIG. 16 (a)-(g) contain additional experimental data validating the differential activity of ChiLob 7/4 h2A and h2B forms.

FIG. 18 (a) contains a schematic representation of differentially disulfide linked h2 isoforms (adapted from (Martinez 2008), FIG. 18(b) shows nrCE-SDS profiles of the indicated ChiLob 7/4 mAb. The h2A and h2B positions and a 10 kDa standard are indicated.

DETAILED DESCRIPTION

Definitions

Figures 3A, 3B, 3C, 3D:
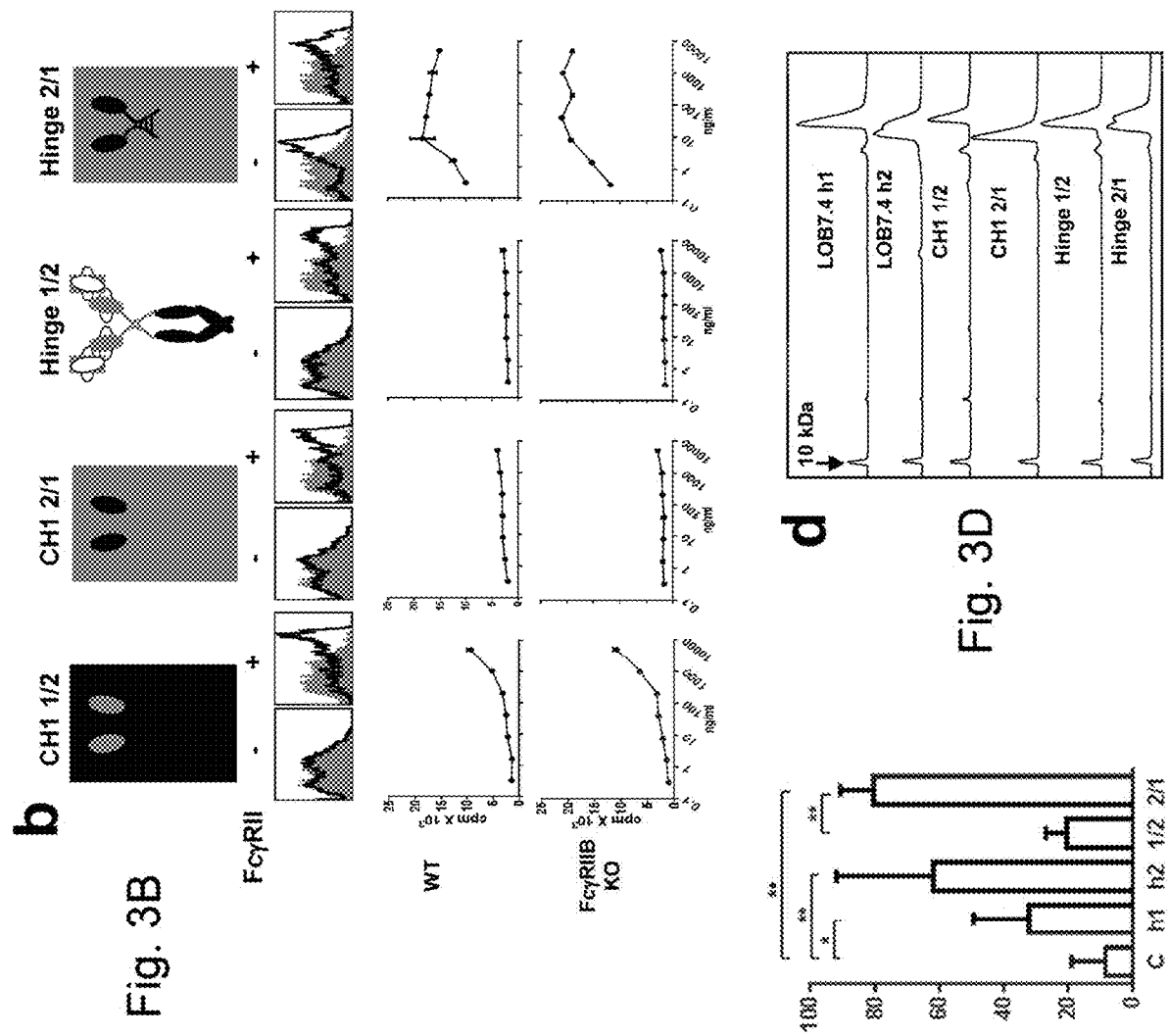
FIG. 3(a)-(d) contain the results of experiments showing that the h2 $C_H1$ and hinge regions impart FcγR-independent agonistic activity to LOB7.4

As mentioned, the present invention broadly relates to novel agonistic or antagonistic antibodies and fusion proteins, and the manufacture and use thereof in therapy, wherein said antibodies or fusion proteins comprise human IgG2 constant domains, where the antibody comprises specific mutations that result in the antibody or fusion protein possessing enhanced agonist or antagonist properties.

It is to be understood that this invention is not limited to the particular methodology, protocols, cell lines, animal species or genera described, as such may vary. It is also to be understood that the terminology used herein is for the purpose of describing particular embodiments only, and is not intended to limit the scope of the present invention which will be limited only by the appended claims. As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

"Agonist" refers to a compound that, in combination with a receptor, can produce a cellular response. An agonist may be a ligand that directly binds to the receptor. Alternatively, an agonist may combine with a receptor indirectly by, for example, (a) forming a complex with another molecule that directly binds to the receptor, or (b) otherwise resulting in the modification of another compound so that the other compound directly binds to the receptor. An agonist may be referred to as an agonist of a particular receptor or family of receptors (e.g., a TNF or TNFR agonist). A "superagonist" is one having mutations in the cysteines of the hinge and CH1 regions providing optimal agonistic properties.

"Antagonist" refers to a compound that when contacted with a molecule of interest, e.g., a TNF or TNFR family superfamily member or other ligand or receptor causes a decrease in the magnitude of a certain activity or function of the molecule compared to the magnitude of the activity or function observed in the absence of the antagonist. Particular antagonists of interest include antibodies and fusion proteins that are specific to TNFR superfamily members that comprise IgG2 constant domains.

"Antigen" refers to any substance that is capable of being the target of an immune response. An antigen may be the target of, for example, a cell-mediated and/or humoral immune response raised by a subject organism. Alternatively, an antigen may be the target of a cellular immune response (e.g., immune cell maturation, production of cytokines, production of antibodies, etc.) when contacted with immune cells.

"TNF/R" herein generally refers to any member of either the Tumor Necrosis Factor (TNF) Superfamily or the Tumor Necrosis Factor Receptor (TNFR) Superfamily. The TNF and TNFR Superfamily includes, for example, as CD40, CD40L (CD154), LTα, LTβ, LT-βR, FASL (CD178), CD30, CD30L (CD153), CD27, CD27L (CD70), OX40, OX40L, TRAIL/APO-2L, 4-1BB, 4-1BBL, TNF, TNF-R, TNF-R2, TRANCE, TRANCE-R, GITR or "glucocorticoid-induced TNF receptor", GITR ligand, RELT, TWEAK, FN14, TNFα, TNFβ, RANK, RANK ligand, LIGHT, HVEM, GITR, TROY, and RELT. Unless otherwise indicated, reference to a TNF/R agonist or antagonist compound can include the compound in any pharmaceutically acceptable form.

"B7 family member" or "B7-CD28 family member" refers to a member of a large family of receptors and ligands expressed on immune cells involved in immune signaling. The typical structural elements common to members of the B7 polypeptide family include an extracellular domain including a V-like and a C-like Ig domain. A signal sequence is found at the N-terminus of full-length B7 family polypeptides, and is followed, in N-to-C order, by a V-like Ig domain, a C-like Ig domain, a transmembrane domain, and an intracellular domain. There are certain key residues within the extracellular domains of B7 polypeptides, the two pairs of conserved cysteine residues—one pair in each Ig domain—that are involved in disulfide bond formation and the three-dimensional conformation of the polypeptide. The B7 polypeptide family is moderately conserved, with the Ig domains of human family members very similar to each other, and to the Ig domains of B7 family members from other species. The family includes subfamilies including B7-1 (CD80), B7-2 (CD86), and B7-H1, and the butyrophilin (BTN)/MOG (myelin oligodendrocyte glycoprotein-like) family members, with the immunomodulatory B7 subfamily lacking a B30.2 domain and the butyrophilin/MOG subfamily having a B30.2 domain. Members of the B7/CD28 superfamily include by way of example B7.1 (CD80), B7.2 (CD86), B7-DC (PD-L2 or CD273), B7-H1, 87-H2, B7-H3 (CD276), B7-H4 (VTCN1), B7-H5 (VISTA), B7-H6 (NCR3LG1), B7-H7 (HHLA2), PD-1 (CD279), PD-L3, CD28, CTLA-4 (CD152), ICOS(CD278), BTLA, NCR3, CD28H, and NKp30.

The terms "biological effects associated with X" and "X activity" e.g., a TNF or TNFR superfamily member or other immune cell receptor are used interchangeably and include any biological effect associated with the moiety with which the agonist or antagonist specifically interacts, e.g., a TNF or TNF/R superfamily member.

The term "host cell" herein in general refers to any cell engineered to express one or more antibody polypeptides according to the invention. This includes by way of example bacterial, fungal, yeast, mammalian, invertebrate such as insect, plant and avian cells.

The term "expression vector" refers to DNA vectors which contain elements that facilitate manipulation for the expression of a foreign protein within the target host cell. Conveniently, manipulation of sequences and production of DNA for transformation is first performed in a bacterial host, e.g. *E. coli*, and usually vectors will include sequences to facilitate such manipulations, including a bacterial origin of replication and appropriate bacterial selection marker. Selection markers encode proteins necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, (b) complement auxotrophic deficiencies, or (c) supply critical nutrients not available from complex media. Exemplary vectors and methods for transformation of yeast are described, for example, in Burke, D., Dawson, D., & Stearns, T. (2000). Methods in yeast genetics: a Cold Spring Harbor Laboratory course manual. Plainview, N.Y.: Cold Spring Harbor Laboratory Press. The polypeptide coding sequence of interest is operably linked to transcriptional and translational regulatory sequences that provide for expression of the polypeptide in yeast cells. These vector components may include, but are not limited to, one or more of the following: an enhancer element, a promoter, and a transcription termination sequence. Sequences for the secretion of the polypeptide may also be included, e.g. a signal sequence, and the like. A yeast origin of replication is optional, as expression vectors are often integrated into the yeast genome. In one embodiment of the invention, the polypeptide of interest is operably linked, or fused, to sequences providing for optimized secretion of the polypeptide from yeast diploid cells.

"Antibody domain" or "region" herein refers to the distinct portions or subunits of an antibody molecule. In the case of an IgG, the heavy chain has four subunits, "$C_H3$", "$C_H2$", "$C_H1$" (the constant portions) and $V_H$ (the variable portion). The light chain has two subunits, $C_L$ and $V_L$. The two $C_H3$ units are joined directly, while the $C_H2$ units are separated by oligosaccharides. The $C_H1$ is located past the "hinge" of the heavy chain and is joined to the $C_L$ unit by a disulfide bond. The "$C_H2$ domain" usually extends from about residues 231 to about 340 of the IgG according to the EU numbering system. The $C_H2$ domain is unique in that it is not closely paired with another domain. Rather, two N-linked branched carbohydrate chains are interposed between the two $C_H2$ domains of an intact native IgG molecule. It has been speculated that the carbohydrate may provide a substitute for the domain-domain pairing and help stabilize the CH2 domain. Burton, Molec. Immunol. 22:161-206 (1985). The "$C_{H3}$ domain" comprises the stretch of residues C-terminal to a $C_{H2}$ domain in an Fc region (i.e., from about amino acid residue 341 to about amino acid residue 447 of an IgG according to the EU numbering system).

The term "Fc region", generally refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. Although the boundaries of the Fc sequence of an immunoglobulin heavy chain might vary, the human IgG heavy chain Fc sequence is usually defined to stretch from an amino acid residue at about position Cys226, or from about position Pro230, to the carboxyl terminus of the Fc sequence. The Fc sequence of an immunoglobulin generally comprises two constant domains, a $C_{H2}$ domain and a $C_{H3}$ domain, and optionally comprises a C.sub.H4 domain. By "Fc polypeptide" herein is meant one of the polypeptides that make up an Fc region, e.g., a monomeric Fc. An Fc polypeptide may be obtained from any suitable immunoglobulin, such as IgG1, IgG2, IgG3, or IgG4 subtypes, IgA, IgE, IgD or IgM.

The term "h2A" conformation herein refers to a specific isoform of IgG2 or a modified antibody containing the hinge and CH2 regions of IgG2. Human IgG2 is unique among immunoglobulins in its ability to shuffle disulfide bonds in its $C_H1$ and hinge regions ((25-28)). Two isoforms of h2 predominate. h2A possesses a flexible, classical IgG conformation in which heavy chain (HC) C127 in $C_H1$ is linked to C214 in the light chain (LC) and 4 inter-HC disulfide bonds are present between opposing hinge cysteines 232, 233, 236 and 239.

The term "h2B" or "h2B conformation herein refers to a second specific isoform of IgG2 or a modified antibody containing the hinge and CH2 regions of hIgG2. ((25-28)). h2B is more compact than h2A and the HC C127 and LC C214 form disulfide bridges with HC hinge cysteines 232 and 233.

"Kabat" or "EU numbering scheme", also called the "EU index" is an art recognized and well accepted system of designating the specific amino acid residues of antibodies and particularly human antibodies, and specific domains which are comprised within whole antibodies or antibody fragments. Unless otherwise specified herein, the numbering of amino acid residues is according to the EU numbering system, also called the EU index, as described in Kabat et al., Sequences of Proteins of Immunological Interest, 5th Ed. Public Health Service, National Institutes of Health, Bethesda, Md., 1991.

The term "operably linked" refers to a nucleic acid that is placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites or alternatively via a PCR/recombination method familiar to those skilled in the art (Gateway® Technology; Invitrogen, Carlsbad Calif.). If such sites do not exist, the synthetic oligonucleotide adapters or linkers are used in accordance with conventional practice.

The term "promoter" refers to untranslated sequences located upstream (5') to the start codon of a structural gene (generally within about 100 to 1000 bp) that control the transcription and translation of particular nucleic acid sequences to which they are operably linked. Such promoters fall into several classes: inducible, constitutive, and repressible promoters (that increase levels of transcription in response to absence of a repressor). Inducible promoters may initiate increased levels of transcription from DNA under their control in response to some change in culture conditions, e.g., the presence or absence of a nutrient or a change in temperature.

The promoter fragment may also serve as the site for homologous recombination and integration of the expression vector into the same site in the host genome; alternatively a selectable marker is used as the site for homologous recombination.

The term "polypeptide of interest" herein generally refers to an agonistic or antagonistic human IgG2 antibody or human IgG2 fusion protein.

The terms "desired antibody" refers generally to a parent antibody or fragment specific to a target, e.g., a TNF or TNF/R superfamily member. The term "antibody" is intended to include any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammals, chicken, other avians, etc., are considered to be "antibodies."

Antibody coding sequences of interest include those encoded by native sequences, as well as nucleic acids that, by virtue of the degeneracy of the genetic code, are not identical in sequence to the disclosed nucleic acids, and variants thereof. Variant polypeptides can include amino acid (aa) substitutions, additions or deletions. The amino acid substitutions can be conservative amino acid substitutions or substitutions to eliminate non-essential amino acids, such as to alter a glycosylation site, or to minimize misfolding by substitution or deletion of one or more cysteine residues that are not necessary for function. Variants can be designed so as to retain or have enhanced biological activity of a particular region of the protein (e.g., a functional domain, catalytic amino acid residues, etc). Variants also include fragments of the polypeptides disclosed herein, particularly biologically active fragments and/or fragments corresponding to functional domains. Techniques for in vitro mutagenesis of cloned genes are known. Also included in the subject invention are polypeptides that have been modified using ordinary molecular biological techniques so as to improve their resistance to proteolytic degradation or to optimize solubility properties or to render them more suitable as a therapeutic agent.

Chimeric antibodies may be made by recombinant means by combining the variable light and heavy chain regions ($V_L$ and $V_H$), obtained from antibody producing cells of one species with the constant light and heavy chain regions from another. Typically chimeric antibodies utilize rodent or rabbit variable regions and human constant regions, in order to produce an antibody with predominantly human domains. The production of such chimeric antibodies is well known in the art, and may be achieved by standard means (as described, e.g., in U.S. Pat. No. 5,624,659, incorporated herein by reference in its entirety. Herein the recombinant chimeric antibody will comprise human IgG2 constant regions modified in the hinge region so as to result in antibodies that function either as receptor or ligand agonists or antagonists.

Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference.

Immunoglobulins and fragments thereof may be modified post-translationally, e.g. to add effector moieties such as chemical linkers, detectable moieties, such as fluorescent dyes, enzymes, toxins, substrates, bioluminescent materials, radioactive materials, chemiluminescent moieties and the like, or specific binding moieties, such as streptavidin, avidin, or biotin, and the like may be utilized in the methods and compositions of the present invention.

The general structure of antibodies in vertebrates now is well understood (Edelman, G. M., Ann. N.Y. Acad. Sci., 190: 5 (1971)). Antibodies consist of two identical light polypeptide chains of molecular weight approximately 23,000 Daltons (the "light chain"), and two identical heavy chains of molecular weight 53,000-70,000 (the "heavy chain"). The four chains are joined by disulfide bonds in a "Y" configuration wherein the light chains bracket the heavy chains starting at the mouth of the "Y" configuration. The "branch" portion of the "Y" configuration is designated the $F_{ab}$ region; the stem portion of the "Y" configuration is designated the $F_C$ region. The amino acid sequence orientation runs from the N-terminal end at the top of the "Y" configuration to the C-terminal end at the bottom of each chain. The N-terminal end possesses the variable region having specificity for the antigen that elicited it, and is approximately 100 amino acids in length, there being slight variations between light and heavy chain and from antibody to antibody.

The variable region is linked in each chain to a constant region that extends the remaining length of the chain and that within a particular class of antibody does not vary with the specificity of the antibody (i.e., the antigen eliciting it). There are five known major classes of constant regions that determine the class of the immunoglobulin molecule (IgG, IgM, IgA, IgD, and IgE corresponding to γ, μ, α, δ, and ε (gamma, mu, alpha, delta, or epsilon) heavy chain constant regions). The constant region or class determines subsequent effector function of the antibody, including activation of complement (Kabat, E. A., Structural Concepts in Immunology and Immunochemistry, 2nd Ed., p. 413-436, Holt, Rinehart, Winston (1976)), and other cellular responses (Andrews, D. W., et al., Clinical Immunobiology, pp 1-18, W. B. Sanders (1980); Kohl, S., et al., Immunology, 48: 187 (1983)); while the variable region determines the antigen with which it will react. Light chains are classified as either κ (kappa) or λ (lambda). Each heavy chain class can be prepared with either kappa or lambda light chain. The light and heavy chains are covalently bonded to each other, and the "tail" portions of the two heavy chains are bonded to each other by covalent disulfide linkages when the immunoglobulins are generated either by hybridomas or by B cells.

The expression "variable region" or "VR" refers to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

The expressions "complementarity determining region," "hypervariable region," or "CDR" refer to one or more of the hyper-variable or complementarity determining regions (CDRs) found in the variable regions of light or heavy chains of an antibody (See Kabat, E. A. et al., Sequences of Proteins of Immunological Interest, National Institutes of Health, Bethesda, Md., (1987)). These expressions include the hypervariable regions as defined by Kabat et al. ("Sequences of Proteins of Immunological Interest," Kabat E., et al., US Dept. of Health and Human Services, 1983) or the hypervariable loops in 3-dimensional structures of antibodies (Chothia and Lesk, *J Mol. Biol.* 196 901-917 (1987)). The CDRs in each chain are held in close proximity by framework regions and, with the CDRs from the other chain, contribute to the formation of the antigen binding site. Within the CDRs there are select amino acids that have been described as the selectivity determining regions (SDRs) which represent the critical contact residues used by the CDR in the antibody-antigen interaction (Kashmiri, S., Methods, 36:25-34 (2005)).

An "epitope" or "binding site" is an area or region on an antigen to which an antigen-binding peptide (such as an antibody) specifically binds. A protein epitope may comprise amino acid residues directly involved in the binding (also called immunodominant component of the epitope) and other amino acid residues, which are not directly involved in the binding, such as amino acid residues which are effectively blocked by the specifically antigen binding peptide (in other words, the amino acid residue is within the "footprint" of the specifically antigen binding peptide).

The phrase that a first antibody binds "substantially" or "at least partially" the same epitope as a second antibody means that the epitope binding site for the first antibody comprises at least 10%, 20%, 30%, 40%, 50%, 60%, 70%, 80%, 90%, or more of the amino acid residues on the antigen that constitutes the epitope binding site of the second antibody. Also, that a first antibody binds substantially or partially the same or overlapping epitope as a second antibody means that the first and second antibodies compete in binding to the antigen, as described above. Thus, the term "binds to substantially the same epitope or determinant as" a monoclonal antibody means that an antibody "competes" with the antibody.

The phrase "binds to the same or overlapping epitope or determinant as" an antibody of interest means that an antibody "competes" with said antibody of interest for at least one, or all residues on an antigen to which said antibody of interest specifically binds. The identification of one or more antibodies that bind(s) to substantially or essentially the same epitope as the monoclonal antibodies described herein can be readily determined using any one of variety of immunological screening assays in which antibody competition can be assessed. A number of such assays are routinely practiced and well known in the art (see, e.g., U.S. Pat. No. 5,660,827, issued Aug. 26, 1997, which is specifically incorporated herein by reference). It will be understood that actually determining the epitope to which an antibody described herein binds is not in any way required identifying an antibody that binds to the same or substantially the same or overlapping epitope as the monoclonal antibody described herein.

The term "fusion protein" refers to a molecule comprising two or more proteins or fragments thereof linked by a covalent bond via their individual peptide backbones, most preferably generated through genetic expression of a polynucleotide molecule encoding those proteins. In the present invention, the fusion protein will generally include IgG2 constant domains, typically wherein the hinge region is mutated in order to lock the H2 in an agonistic or antagonistic conformation.

The term "immunoglobulin fusion protein" refers to a fusion of a functional portion of a polypeptide (generally comprising the extracellular domain of a cell surface protein) with one or more portions of an immunoglobulin constant region, e.g. the hinge, $C_{H1}$, $C_{H2}$ or $C_{H3}$ domains or portions or combinations thereof. In one embodiment, the polypeptide from which the extracellular domain or fragment is derived is a member of the TNF superfamily of ligands and receptors. The Ig portion of the molecule will be derived in whole or part from IgG2 immunoglobulin and potentially will include portions of other immunoglobulin isotypes, including, for example, IgG1, IgG3, IgG4, IgM, IgA etc. Immunoglobulin fusion proteins are referred to herein as Ig for Fc fusion proteins wherein cysteines in the hinge and/or CH1 region are modified or deleted.

Thus, the subject invention generally relates to agonistic or antagonistic antibodies and immunoglobulin fusion proteins comprising the domains of IgG2 constant regions, preferably IgG2 constant regions containing specific mutations in the hinge region. The inventors demonstrate herein, using a combination of in vitro and in vivo approaches, that human IgG2 (h2) delivers unique FcγR-independent agonistic activity to antibodies, in particular anti-CD40 antibodies and antibodies to other TNF/TNFR receptors, including 4-1BB and CD28. More particularly, the present inventors demonstrate using the Materials and Methods as disclosed in the Examples infra the following:

Human IgG2 Imparts Greater Agonistic Activity to Anti-CD40 than Human IgG1

Prior to the present invention, the optimal isotype to use for agonistic mAb's was unknown as a formal investigation of human isotypes for agonistic mAb's had not been reported. In particular, as disclosed in detail infra, an investigation of the anti-human CD40 mAb, LOB7.4, surprisingly revealed that the unique activity of h2 is dependent upon the precise arrangement of hinge and $C_H1$ disulfide bonds.

Chemical 'shuffling' or mutagenesis to 'lock' LOB7.4 into either a more flexible '112A' or more compact 'h2B' conformation endows antagonistic and agonistic properties, respectively. Engineering of h2 in this way allows the development of polypeptides with either immunostimulatory or immunosuppressive characteristics, with direct implication for the design of therapeutic mAbs and therapeutic fusion proteins.

As disclosed in detail infra, the inventors compared the immunostimulatory properties of a mAb against CD40, as well as the co-stimulatory T cell receptors, CD28 and 4-1BB, when expressed with h1 or h2 constant regions. In all cases the inventors found that h2 was more agonistic than h1, independent of both the mAb Fc and FcγR interaction. Analysis of chimeric forms of the anti-human CD40 mAb, LOB7.4, revealed activity was dependent upon the arrangement of disulfide bonds in the h2 hinge. Moreover, mutation of specific cysteine residues could lock the mAb into agonistic or antagonistic conformations. Based on these observations, human IgG2 therefore provides a unique opportunity to manipulate mAb function allowing selection of both FcγR-independent agonistic agents, as well as inhibitors to block inappropriate immune activation.

Previous studies using the anti-mouse CD40 mAb, 3/23, demonstrated that 3/23 m1 was highly agonistic whereas 3/23 m2a was non agonistic due to differences in binding to FcγRIIB (White A L, et al. (2013); White et al (2011)). To analyze the effect of human isotypes on activity, the inventors cloned the variable regions of 3/23 and the anti-human (h) CD40 mAb LOB7.4 onto h1 and h2 constant regions and compared their activity with that of m1 and m2a in a number of in vitro and in vivo assays.

For both mAb, h2 demonstrated similar immunostimulatory properties to m1, whereas h1 and m2a were largely inactive (See FIGS. 1, 2 and 5). In vivo, 3/23 m1 and h2 potently stimulated both Ab and CD8 T cell responses against OVA, activation of splenic DC, and provided protection against tumor development in both a vaccination setting (OVA expressing solid EG7 tumors) and a therapeutic setting (BCL1 lymphoma model) whereas 3/23 h1 and m2a did not (FIG. 5 a-e and (18)). Similarly, in vitro, LOB7.4 h2 caused much greater activation of isolated human B cells, as assessed by cell clumping or cell aggregation as a marker of activation, upregulation of the activation marker CD23 and $^3$H-thymidine incorporation, as well as activation of isolated primary human Langerhans cells as assessed by CD70 upregulation, than did LOB7.4 h1 (See FIG. 6a,b).

LOB7.4 m1 and h2, but not m2a or h1, also allowed activation and proliferation of hCD40 Tg mouse B cells in vitro (See FIG. 1a) and stimulated substantial and significant increases in Ab and endogenous CD8 T cell responses against OVA in hCD40 Tg mice (FIG. 1b,c). Thus, in a number of model systems, with mAb against both mouse and human receptors, h2 constant regions imparted greater agonistic activity to anti-CD40 than h1.

Fc- and FcγR-Independent Activity of Human IgG2

Surface plasmon resonance (SPR) confirmed the low affinity of LOB7.4 h2 for FcγR including FcγRIIB (FIG. 6c), the only FcγR on mouse B cells, suggesting the agonistic activity of h2 was FcγR-independent. Consistent with this, removal of the LOB7.4 h2 Fc to produce Fab'$_2$ did not reduce its ability to promote human or hCD40 Tg mouse B cell activation and proliferation, whereas further cleavage to Fab' or use of h1 or h1 Fab'$_2$ prevented activity (FIG. 1d and data not shown). Additionally, a pan blocking anti-FcγRII mAb did not affect the ability of LOB7.4 h2 to activate human B cells, whereas it did block the activity of LOB7.4 h1 induced by FcγRII over-expressing cross-linking cells (FIG. 6e). Furthermore, although both LOB7.4 m1 and h2 promoted activation and proliferation of hCD40 Tg B cells in vitro, genetic deletion of FcγRIIB ablated the activity of m1 but not h2 (FIG. 1e). Finally, when hCD40 transgenic FcγRIIB WT or KO mice were immunized with OVA, the ability of LOB7.4 m1 to increase CD8 T cell expansion was reduced by >80% in the KO animals, whereas loss of FcγRIIB did not influence the agonistic activity of LOB7.4 h2 (FIG. 1f).

Human IgG2 is Agonistic for Other Co-Stimulatory Receptors

H2 constant regions also imparted FcγR-independent activity to other immunostimulatory mAb. A chimeric h2 of another anti-hCD40 mAb specificity (currently in clinical development, SGN40 (Seattle Genetics)), originally derived from the parental m1 SC26 (24), activated isolated human B cells as assessed by clumping, CD23 upregulation and proliferation, whereas a chimeric h1 did not (FIG. 2a). In addition, both the parental SC26 m1 and SGN40-Soton h2, promoted proliferation of hCD40 Tg mouse B cell (FIG. 2b), whereas only SGN40-Soton h2 stimulated proliferation when FcγRIIB was genetically deleted (FIG. 2b).

Similar observations were made using mAb against two human T cell receptors, 4-1BB (CD137; mAb produced in-house) and CD28 (based on TGN1412 patented sequence). For both targets, h2 was more agonistic than h1 when promoting in vitro human T cell proliferation (FIG. 2c). The anti-hCD28 h2 mAb caused clumping and proliferation of purified T cells that do not express FcγR, again supporting an FcγR-independent mechanism of action (FIG. 2c).

The Human IgG2 Hinge and $C_H1$ Domains are Essential for Agonistic Activity

As the h2 Fc was not required for activity, we investigated the role of the $C_H1$ and hinge domains using chimeric mAb in which either the $C_H1$ or both the $C_H1$ and hinge domains of LOB7.4 h1 and h2 were switched (FIG. 3). Proliferation of hCD40 Tg WT or FcγRIIB KO B cells over an extended mAb concentration range (<1 to >5,000 ng/ml) was used to measure activity. Native LOB7.4 h2 caused marked activation and proliferation of both cell types, with activity peaking around 200 ng/ml whereas little response was observed to h1 at any concentration (FIG. 3a). LOB7.4 m1 stimulated proliferation in FcγRIIB WT but not KO cells and was considerably less potent than h2 at low concentrations (FIG. 3a, bottom 2 panels). The mAb with switched $C_H1$ domains (CH1 1/2 and $C_H1$ 2/1) or where the $C_H1$ and hinge of h1 were transferred into to h2 (Hinge 1/2) had little activity in either cell type. In contrast, transfer of the h2 CH1 and hinge regions into h1 (Hinge 2/1) produced activity similar to that of native h2 (FIG. 3b). These data suggest both the $C_H1$ and hinge domains of h2 are essential for agonistic activity.

Consistent with the in vitro data, LOB7.4 h1 and the Hinge 1/2 mutant caused little stimulation of CD8 T cell responses against OVA in hCD40 Tg mice, whereas both LOB7.4 h2 and the Hinge 2/1 chimera caused substantial and significant increases in anti-OVA-specific CD8 T cell expansion (FIG. 3c).

Disulfide Shuffling Dictates huIgG2 Agonistic Activity

Figure 17:
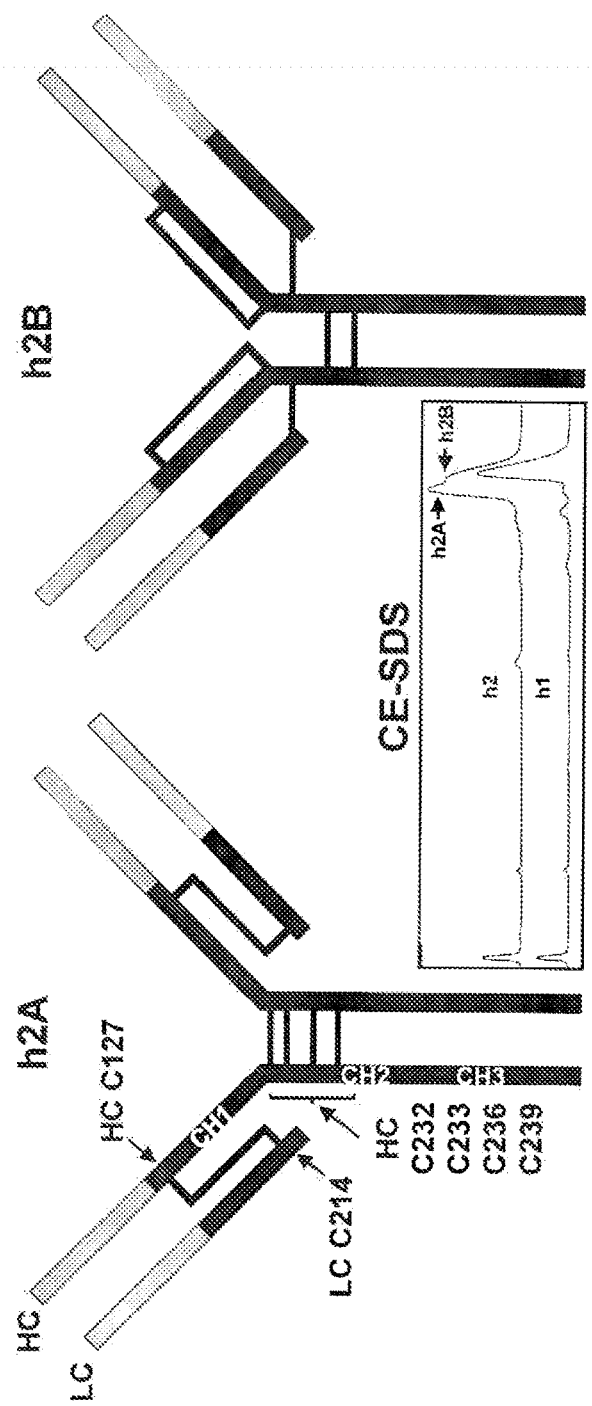
FIG. 17 contains a schematic representation of differentially disulfide linked h2 isoforms (adapted from (Martinez 2008) The left panel shows the structure of h2A, believed to be the form in which h2 is synthesized, and the right panel h2B, shows the predominant alternatively arranged form. Cysteine residues involved in shuffling are highlighted. Disulfide bonds are represented by black lines between or within chains. The CE-SDS profiles shown illustrate the resolution of the h2A and h2B forms (as described, ref) whereas h1 resolves as a single peak.
Figure 19:
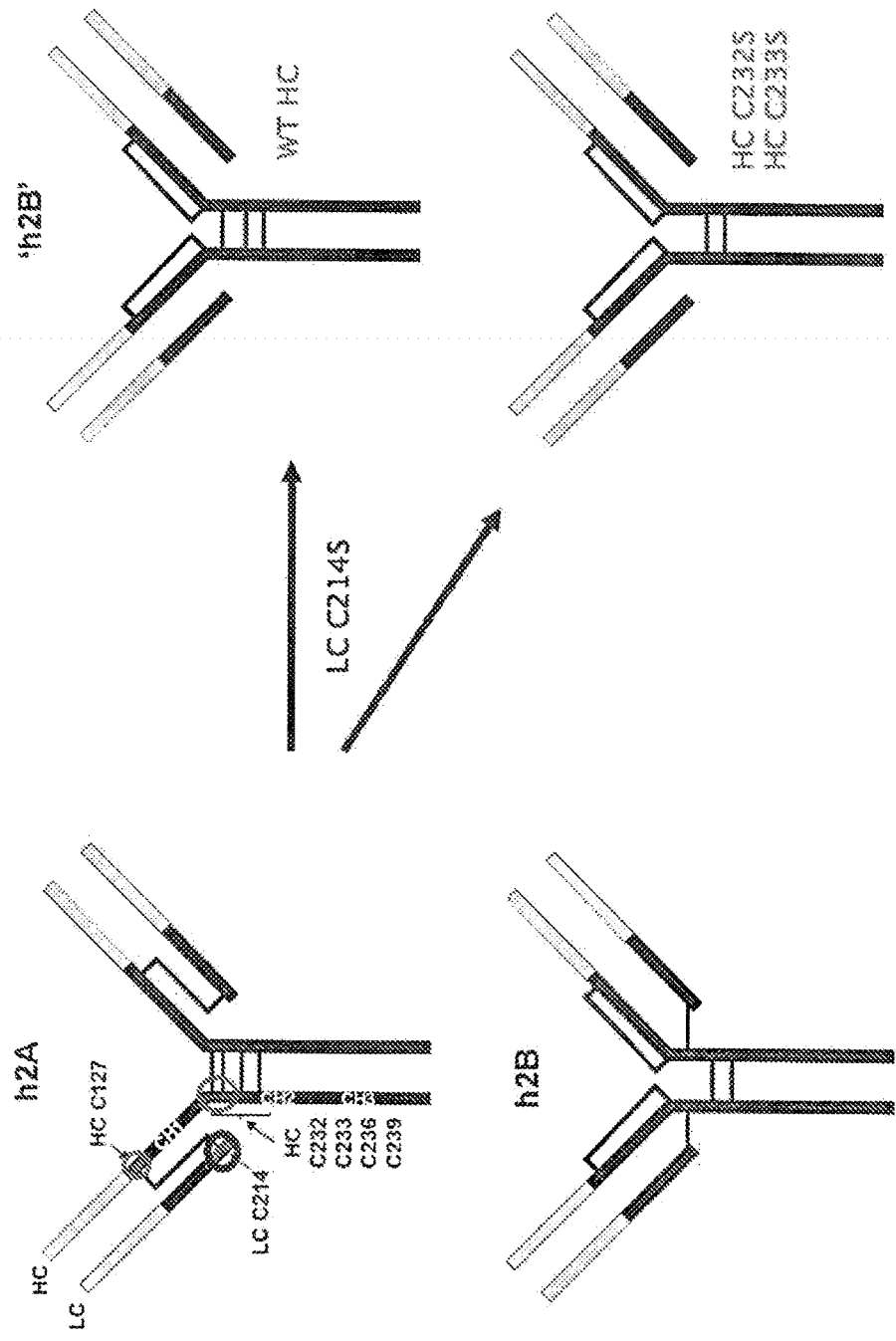
FIG. 19, FIG. 20 and FIG. 21 schematically show how mutagenesis can 'lock' antibodies into h2a and h2B forms.
Figure 20:
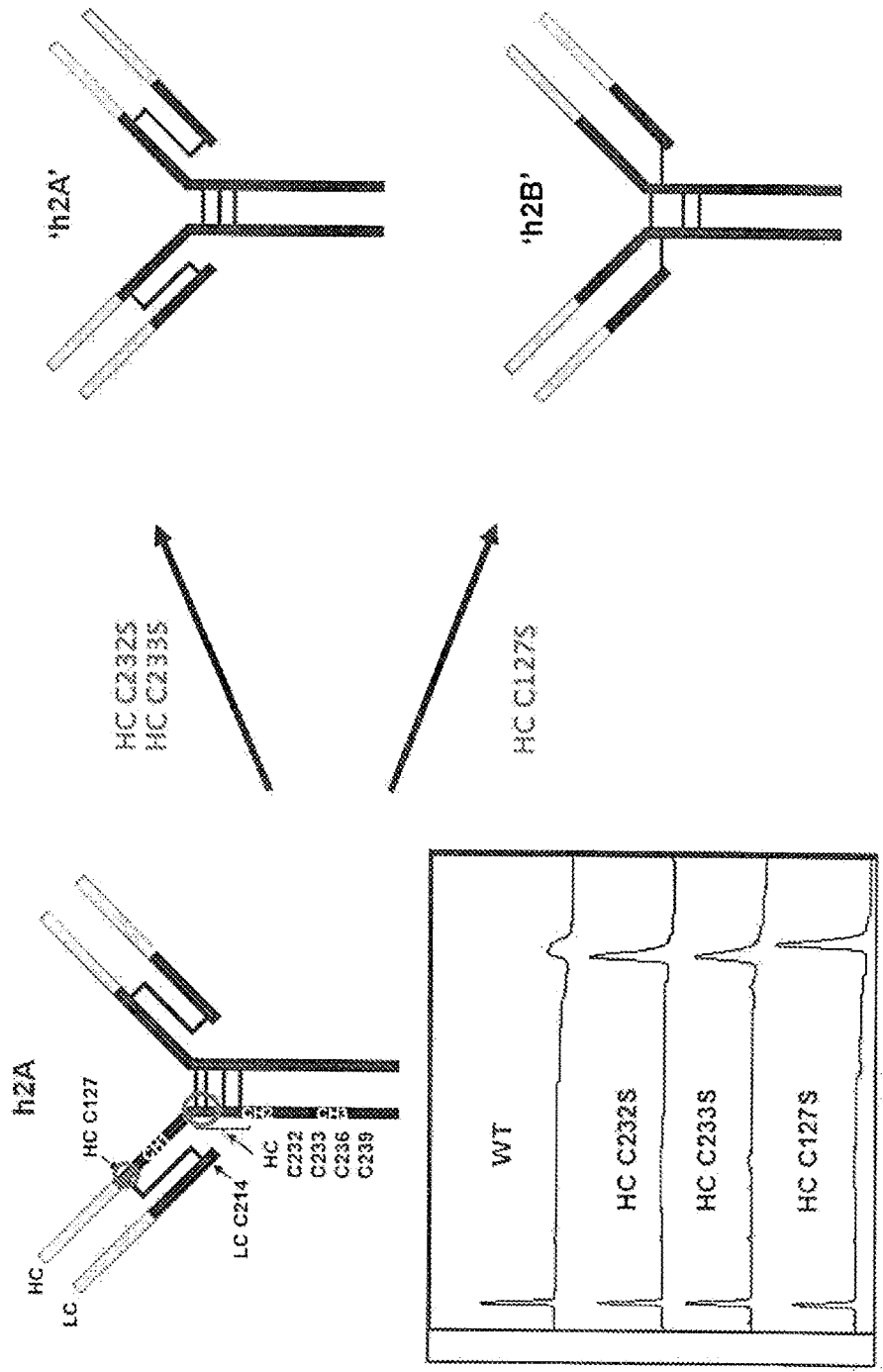
Figure 21:
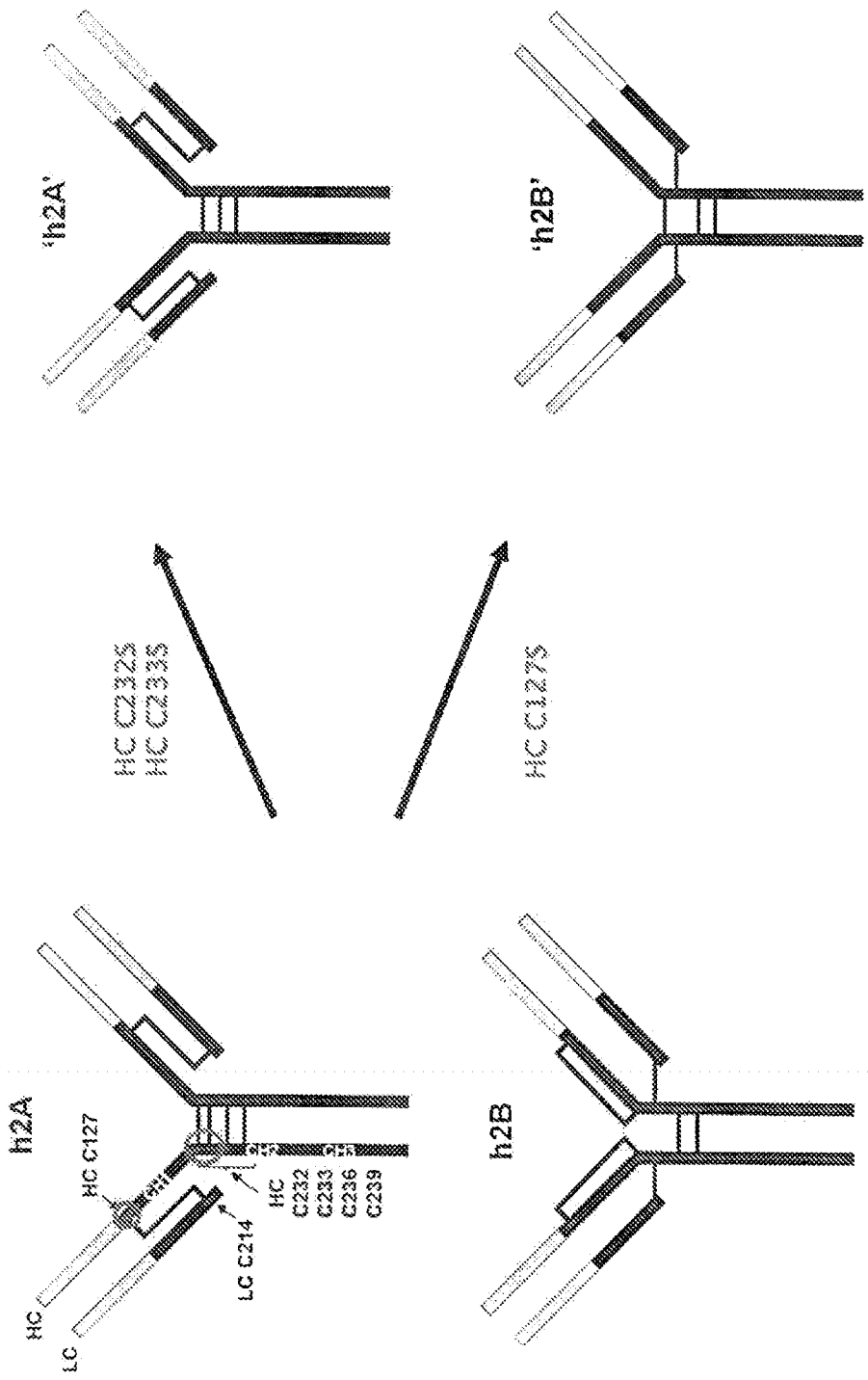
Figure 22:
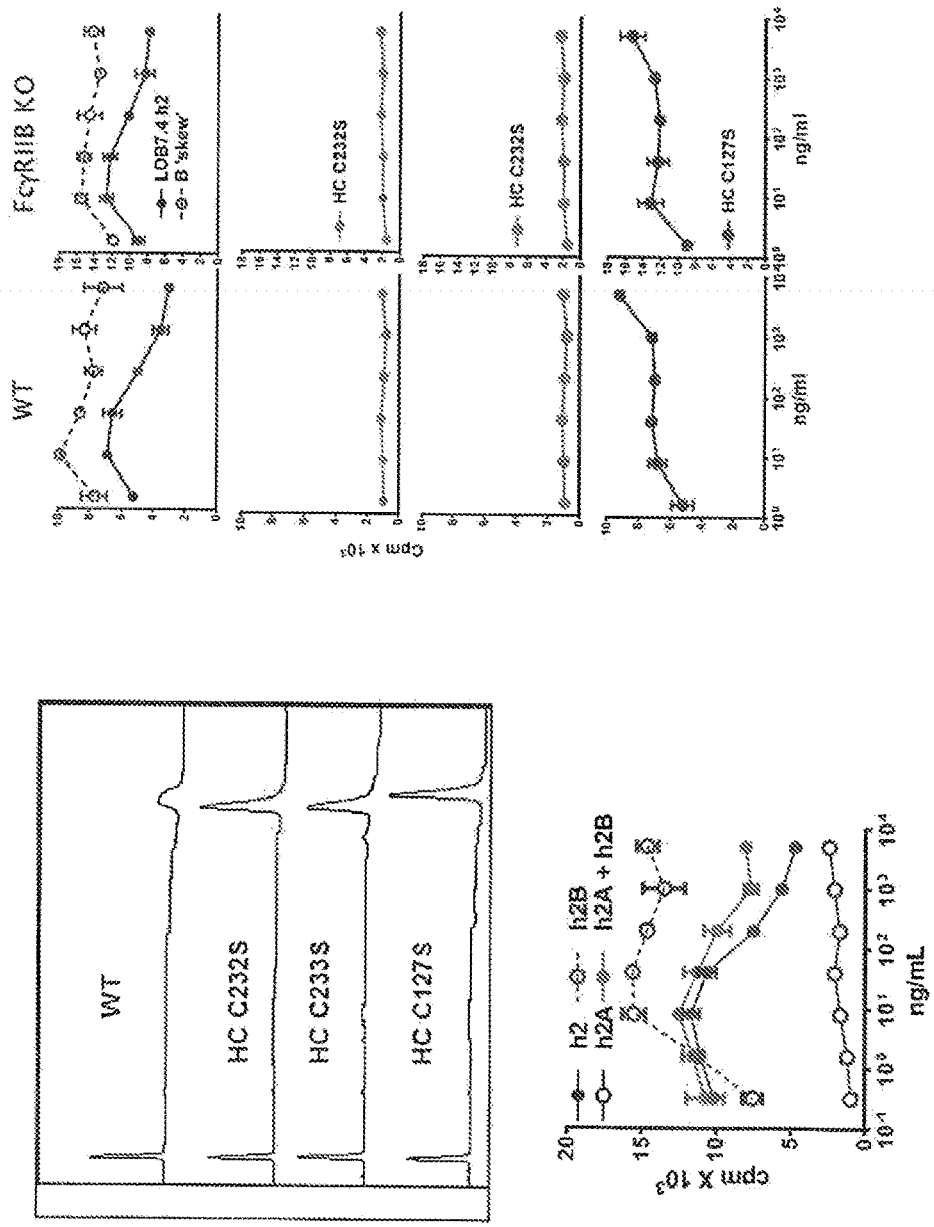
FIG. 22, FIG. 23, FIG. 24 and FIG. 25 contain experimental data showing how mutagenesis of h2 produces different agonists and antagonists.
Figure 23:
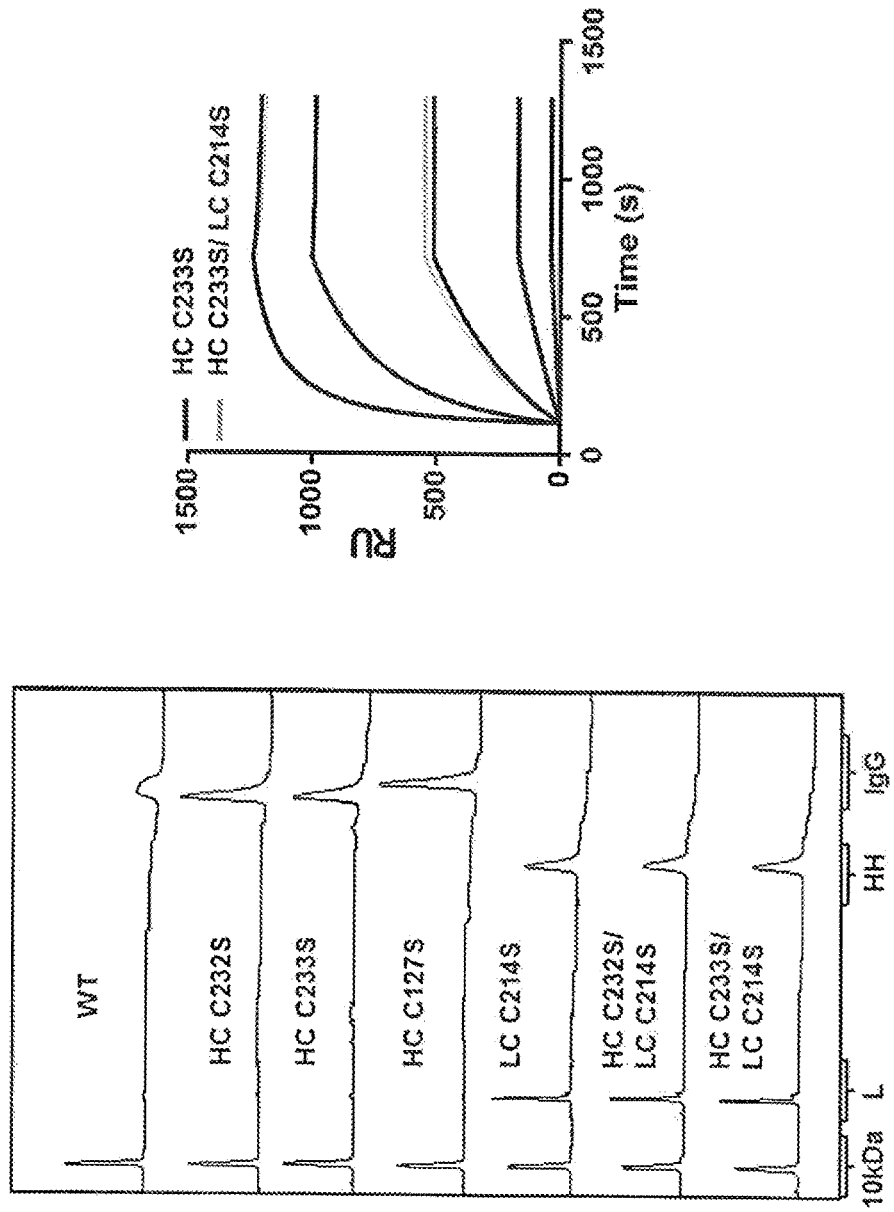
Figure 24:
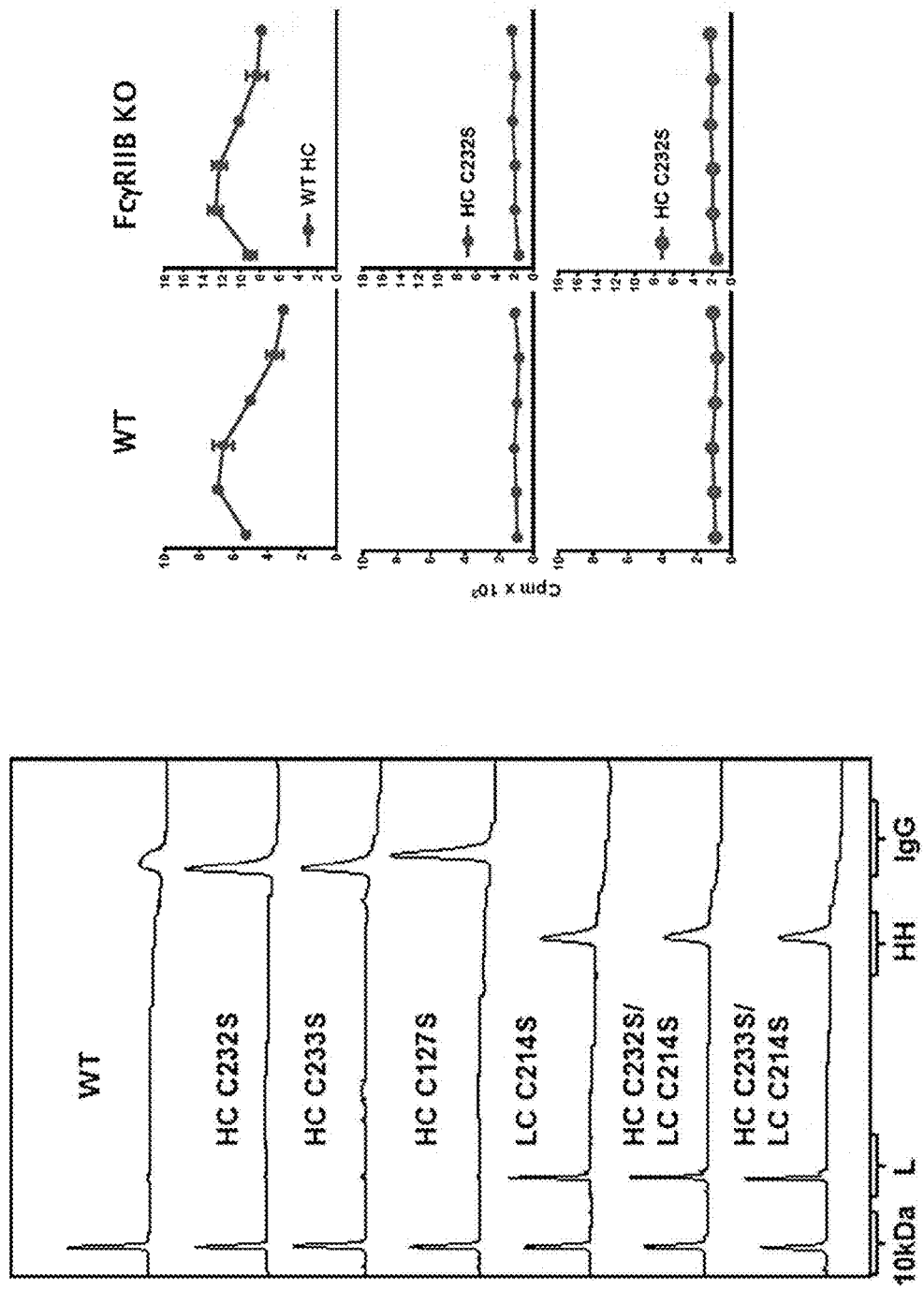
Figure 25:
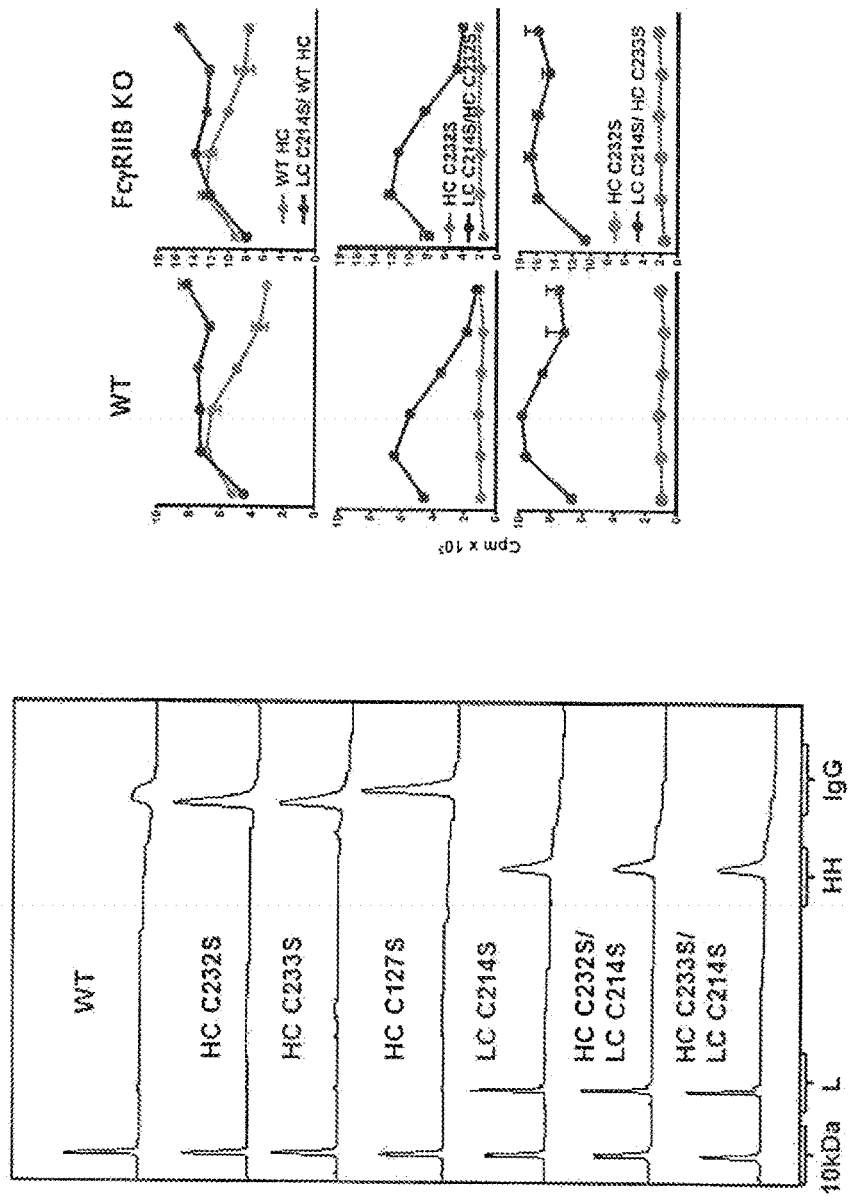
Figure 26:
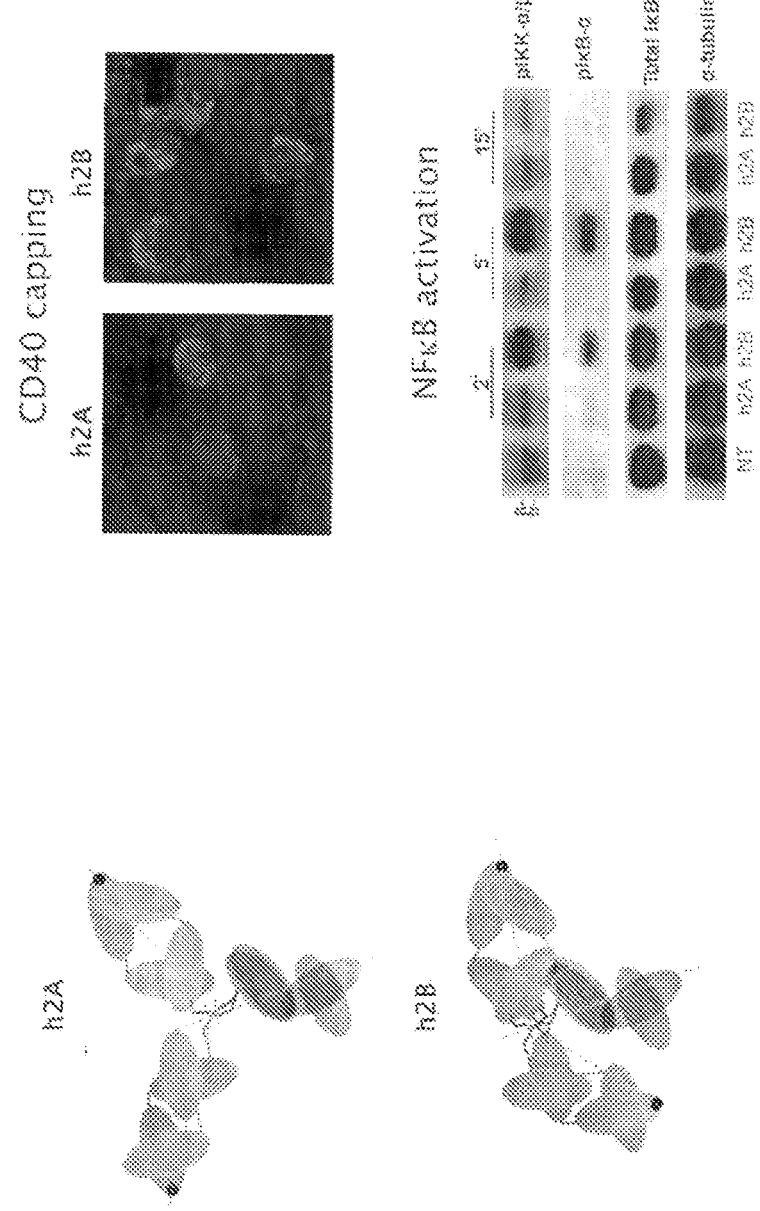
FIG. 26 contains experimental data suggesting that the agonistic or antagonistic properties of h2B versus h2A forms may involve antigen capping or NFkB activation (suggesting that multimerization may overcome requirement for FcγR x-linking).
Figure 27:
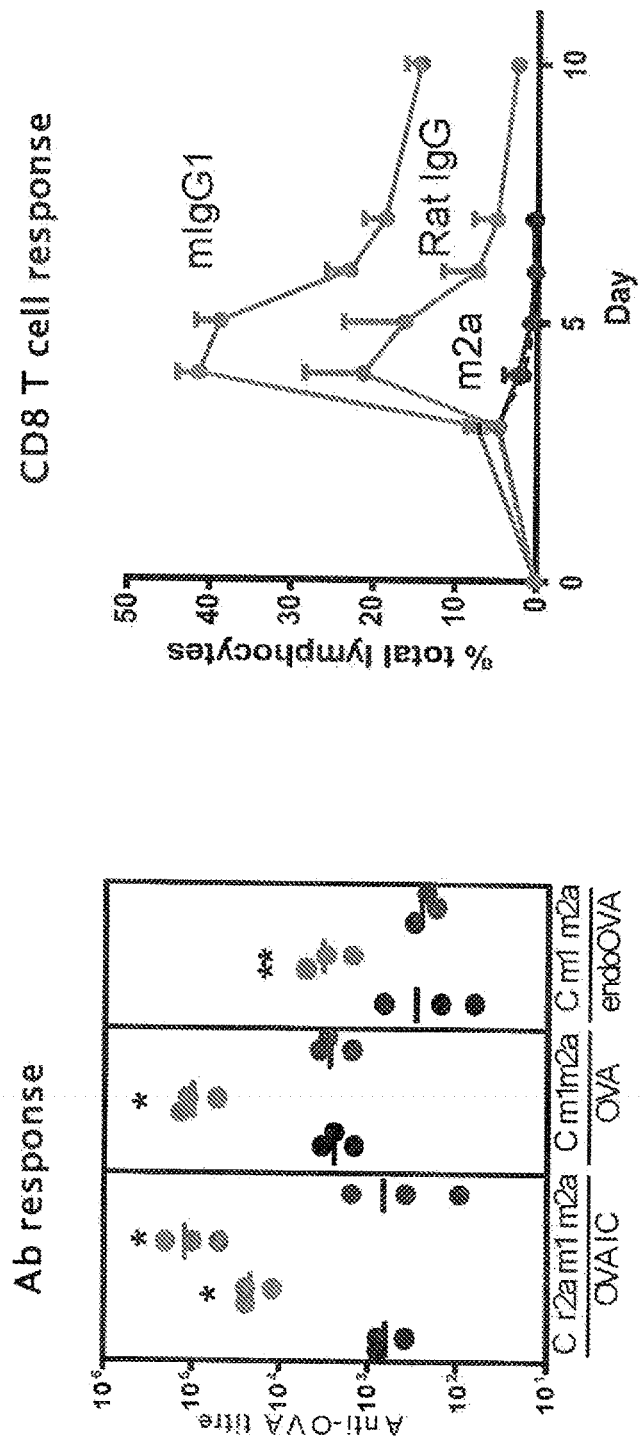
FIG. 27 contains experimental data showing immunostimulatory properties of different isotype forms of an anti-CD40 antibody.
Figure 28:
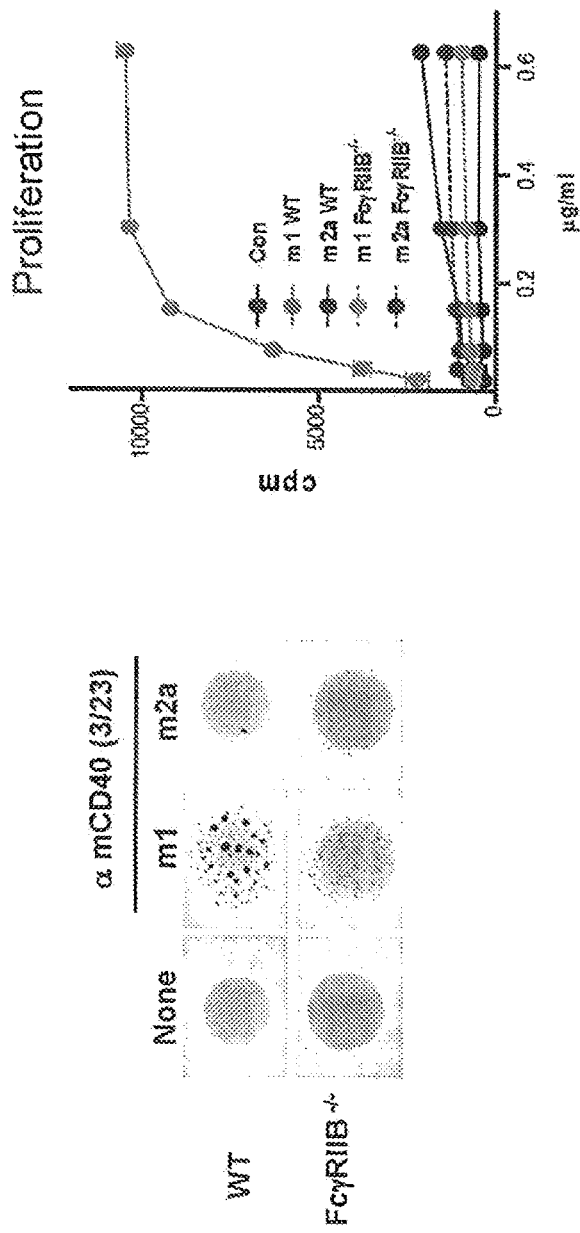
FIG. 28 contains results of B cell assays showing effects of different isotype forms of an anti-CD40 antibody on B cell proliferation.

Human IgG2 is unique among immunoglobulins in its ability to shuffle disulfide bonds in its $C_H1$ and hinge regions (FIG. 17; (Wpych et al., (2008); Martinez et al. (2008); Zhang et al., (2010)) Two isoforms of h2 predominate: h2A, with a flexible, classical IgG conformation in which heavy chain (HC) C127 in $C_H1$ is linked to C214 in the light chain (LC) and 4 inter-HC disulfide bonds are present between opposing hinge cysteines 232, 233, 236 and 239 (FIG. 17); and h2B that is more compact and in which HC C127 and LC C214 form disulfide bridges with HC hinge cysteines 232 and 233 (FIG. 17). The h2A and h2B forms can be separated analytically by non-reducing capillary electrophoresis (nrCE-SDS (26, 29) that reveals a double peak for h2 and a single peak for h1 (FIG. 17).

nrCE-SDS analysis of the chimeric LOB7.4 mAbs revealed only the Hinge 2/1 mutant retained the ability to shuffle disulfides and produce a double peak (FIG. 3d). This is consistent with the observation that mutation of any one of HC cysteines 127 (in $C_H1$), 232 or 233 (in the hinge) prevents disulfide rearrangement (26, 30) and suggest the agonistic activity of LOB7.4 h2 is associated with its ability to shuffle disulfide bonds.

To determine whether the h2A and h2B forms were associated with different levels of agonistic activity, we chemically 'skewed' LOB7.4 towards its h2A or h2B forms in redox buffer with or without denaturant, as described (28). Incubation in redox buffer alone forced the majority (~75%) into h2B as assessed by nrCE-SDS whereas the addition of guanidine hydrochloride skewed >70% to h2A (FIG. 4A, left panel). The skewed mAb were associated with markedly different activities as assessed by their ability to cause clumping and activation of human B cells or the proliferation of hCD40 Tg B cells (FIG. 4a and data not shown), with h2B considerably more active than h2A. Similar differences in activity were observed when the anti-mouse CD40 mAb, 3/23, h2 was skewed towards it's A and B forms (FIG. 1a-c).

Point Mutations can Lock h2 into Agonistic and Antagonistic Conformations

Figure 7B:
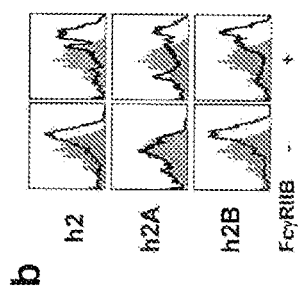
FIG. 7 (a)-(d) contain the results of experiments demonstrating the antagonistic and agonistic properties of h2A and h2B.
Figure 7D:
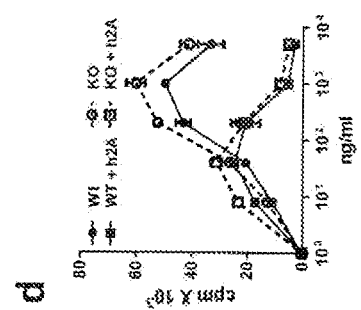
Figure 7A:
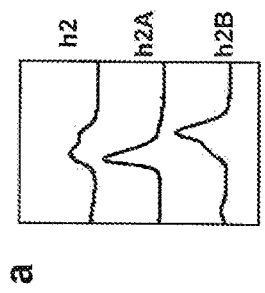
Figure 7C:
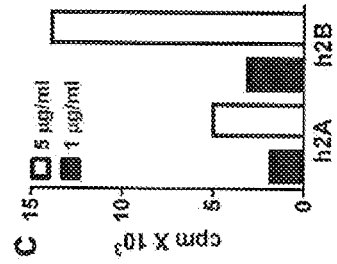

Elegant studies by Ballard and others (26, 30) demonstrated that mutation of HC C232 or C233 to S can lock h2 into its h2A form, whereas HC C1275 produces a form similar to that of h2 B. We introduced these mutations into LOB7.4 h2 and confirmed their shift to h2A or h2B by nrCE-SDS (FIG. 4b). HC C232S or C233S resulted in a complete loss of LOB7.4 h2 agonistic activity as measured by hCD40 Tg B cell proliferation (either WT or FcγRIIB KO; FIG. 4c, blue traces). In contrast, HC C127S increased activity at high concentrations relative to native h2, to a level almost as high as that for skewed h2B (FIG. 4c, bottom panel, blue trace). Intriguingly, co-incubation with HC C233S h2A reduced the activity of LOB7.4 h2B, particularly at high concentrations, producing a characteristic bell-shaped curve almost identical to that of native h2 (FIG. 4d). Similarly, LOB7.4 HC C233S also drastically reduced the agonistic activity of SGN40 h2 on hCD40 Tg B cell in vitro (FIG. 7d).

Mutagenesis of LC C214 also produced marked changes in activity. LC C214S prevented disulfide linkage between the LC and HC, resulting in separate LC and HC dimer peaks on nrCE-SDS (FIG. 4c). It is important to note that loss of the H:L disulfide bond does not affect antibody binding as in physiological buffers the two chains are held together by non-covalent bonds. This was confirmed by the identical affinity for CD40 on SPR of HC C233S when combined with either the WT LC or LC C214S (FIG. 4e).

When LC C214S was combined with WT HC, HC C232S or C233S, the HC dimer ran as a single species on nrCE-SDS suggesting a single conformation in each case. In all cases, LC C214S increased agonistic activity and provided characteristic B cell proliferation profiles: with WT HC a profile similar to the C127S mutant was observed; with HC 232S a profile similar to native h2 was produced; and when combined with HC C233S maximum activity was seen very similar to that of skewed h2B (FIG. 4c, red traces). These profiles were highly reproducible and similar using hCD40 Tg or human B cells (data not shown). Thus, subtle changes in primary sequence can have drastic effects on h2 activity enabling the engineering of a spectrum of agonistic and antagonistic agents.

Human IgG Isotypes and Anti-CD40 Activity.

To examine the effect of human constant regions on agonistic activity we used the anti-human CD40 mAb, ChiLob 7/4 (Chowdhury, 2014), currently in Phase 1 clinical trial in cancer patients. Agonistic activity was initially assessed by the ability of ChiLob 7/4 to cause human B cell activation and proliferation in vitro when chimerized onto different human constant regions. All chimeras bound similarly to CD40 as determined by flow cytometry (FIG. 8D). Fab' fragments of ChiLob 7/4 h1 and h2 also bound to immobilized hCD40 with similar affinities (10.0 and 10.2× $10^{-9}$ M, respectively) as measured by SPR (FIG. 8E). When added to purified human B cells ChiLob 7/4 h2 caused much greater B cell activation and proliferation as assessed by homotypic adhesion (cell clumping) and 3H thymidine uptake, respectively, compared to ChiLob 7/4 h1 or h4 (FIG. 8A). To determine that Fab' arm exchange did not account for the lack of activity of h4, we introduced a stabilizing S228P mutation into h4 (Angal et al., 1993). This alteration (h4*in FIG. 8A) did not alter h4 activity.

In pre-clinical models immune stimulatory and therapeutic effects of anti-CD40 mAb can be mediated through upregulation of the co-stimulatory molecule, CD70, on DC resulting in enhanced CD8 T cell immunity (French et al., 1999; French et al., 2007; Sanchez et al., 2007). To compare the ability of ChiLob 7/4 h1 and h2 to activate human DC we assessed their capacity to upregulate CD70 expression on primary human Langerhans cells in vitro (FIG. 8B), as well as their ability to enhance Langerhans cell-induced priming of EBV-specific human CD8 T cells measured by IFNγ measured by I FIG. 8C). Consistent with effects on B cells, ChiLob 7/4 h2 enhanced both Langerhans cell CD70 expression and CD8 T cell priming whereas ChiLob 7/4 h1 did not.

The in vivo agonistic activity of ChiLob 7/4 isotypes was examined in hCD40 Tg mice (Ahonen et al., 2002). Initial in vitro studies confirmed that hCD40 in mouse cells responded to ligation with ChiLob 7/4 similarly to that in human cells, as ChiLob 7/4 h2 stimulated much greater activation and proliferation of isolated hCD40 Tg mouse B cells than h1 (FIG. 8D) that was dependent upon the expression of hCD40 (FIG. 9F). To test in vivo agonistic activity, we examined the ability of ChiLob 7/4 to enhance CD8 T cell and Ab responses when co-administered with the model antigen, OVA. Consistent with the in vitro data, ChiLob 7/4 h2 stimulated significantly greater anti-OVA CD8 T-cell expansion as well as Ab responses than observed with h1 (FIG. 8E). Thus using a series of both in vitro and in vivo approaches ChiLob 7/4 demonstrated greater immunostimulatory activity when expressed with h2 versus h1 or h4 constant regions.

Similar differences between h1 and h2 agonistic activity were also observed in vivo when we examined the anti-mouse CD40 mAb, 3/23, where again 3/23 h2 but not h1 stimulated potent anti-OVA CD8 T-cell and Ab responses (FIG. 8F) and upregulated CD70 on splenic DC (FIG. 9G). Importantly, this difference in immunostimulatory capacity correlated with differences in therapeutic activity where 3/23 h2 but not h1 provided protection against tumor development in both a vaccination setting where mice immunized with OVA plus anti-CD40 were challenged with the OVA-expressing EG7 tumor (FIG. 9G) and a therapeutic setting where mice with established B cell lymphoma (BCL$_1$ lymphoma model (White, 2014); FIG. 8H) were treated with a single 100 µg dose of mAb.

Human IgG2 Activity is FcγR-Independent.

The low affinity of h2 for FcγRIIB (Bruhns et al., 2009), the predominant FcγR on B cells, suggested that, unlike agonistic m1 which uses FcγRIIB as a crosslinker (White et al., 2011), its activity may be FcγR independent. Indeed, surface plasmon resonance (SPR) where soluble FcγRs were passed over immobilized mAb revealed very little binding of ChiLob 7/4 h2 to any human or mouse FcγR (FIGS. 11A and B) whereas ChiLob 7/4 h1 clearly bound hFcγRI, IIA and IIIA as well as mFcγRI and IV under the same conditions (FIGS. 11A and B). A number of approaches confirmed the FcγR independent activity of h2. First, a pan-blocking anti-FcγRII mAb (AT10) failed to prevent activation of human B cells by ChiLob 7/4 h2, as assessed by homotypic adhesion and CD23 upregulation (FIG. 10A). In contrast, AT10 completely blocked activation by ChiLob 7/4 h1 induced in the presence of FcγII-expressing cross-linking cells (FIG. 10A).

Second, removal of the ChiLob 7/4 h2 Fc through pepsin cleavage (producing F(ab')2 fragments) did not prevent activation and proliferation of human B cells whereas reduction to Fab' eliminated activity (FIG. 10C). In contrast, under the same conditions ChiLob 7/4 h1 was unable to activate cells when added as IgG, F (ab')$_2$ or Fab', although when added in excess, each form prevented activation by ChiLob 7/4 h2 (FIG. 10B; FIG. 11F). Third, genetic deletion of FcγRIIB from mouse B cells, the only FcγR expressed by these cells, did not prevent their proliferation in response to ChiLob 7/4 h2 over a wide concentration range (FIG. 10C) whereas response to ChiLob 7/4 m1, that is dependent on FcγRIIB cross-linking for activity (White et al., 2011), was lost (FIG. 10C). Of note, ChiLob 7/4 h2 produced a characteristic 'bell' shaped response curve when used to stimulate B cells at different concentrations and was active at very low levels in contrast to cross-linking dependent ChiLob 7/4 m1 whose activity increased as concentrations rose (FIG. 10D). These different curves presumably reflect the different mechanisms by which the isotypes impart agonistic activity and are discussed further below.

The FcγR-independent activity of ChiLob 7/4 h2 was also confirmed, in vivo. Genetic deletion of FcγRIIB, previously shown to result in loss of agonistic activity of mAb against CD40 (Li and Ravetch, 2011; White et al., 2011; White, 2014) Fas, DR4 and DR5 (Li and Ravetch, 2012; Wilson et al., 2011; Xu et al., 2003) did not reduce expansion of OVA-specific CD8 T cells induced by ChiLob 7/4 h2 compared to that observed in wild type (WT) mice, whereas, as expected, activity of ChiLob 7/4 m1 was lost in the FcγRIIB KO (FIG. 10D). Both mAb remained active in γ chain KO mice that have no activatory FcγR (FIG. 10D). Finally, ChiLob 7/4 provided robust stimulation of CD8 T cell responses in vivo when administered as a F(ab')$_2$ fragment, whereas no response was observed with F(ab')2 of ChiLob 7/4 h1 (FIG. 10E).

Human IgG2 is Agonistic for Multiple Targets.

We next evaluated the influence of h2 constant regions on the activity of another hCD40 mAb in clinical trial, SGN40, also a chimeric h1 (Advani et al., 2009). The variable regions of SGN40 were synthesized from the patent sequence and chimerized onto h1 and h2 constant regions, to produce SGN40-Soton h1 and h2. Similar to ChiLob 7/4, SGN40-Soton h2 provided greater activation and proliferation of human B cells than SGN40-Soton h1 (FIG. 12A) and proliferation of hCD40 Tg B cells in response to SGN40-Soton h2 but not its parental m1, SC26 (Hanks et al., 2005), was independent of FcγRIIB expression (FIG. 12B). In addition, SGN40-Soton h2 significantly and potently increased OVA-specific CD8 T cell responses in vivo in FcγRIIB KO mice whereas SGN40-Soton h1 did not (FIG. 12C). Further studies with mAb directed against two other co-stimulatory receptors in clinical development, h4-1BB and hCD28, revealed similar differences in h1 and h2 agonistic function assessed by human T-cell proliferation in vitro (FIGS. 12D-E). For hCD28, purified T cells were used. T cells generally lack FcγR but displayed homotypic adhesion as well as increased proliferation in response to anti-hCD28 h2, again supporting an FcγR-independent mode of action (FIG. 12E). Similar to ChiLob 7/4 (FIG. 8A), h4 constant regions did not confer activity to anti-hCD28 in purified T-cell cultures (FIG. 12E).

H2 Activity Depends on Both the Human IgG2 CH1 and Hinge Regions.

Figure 14:
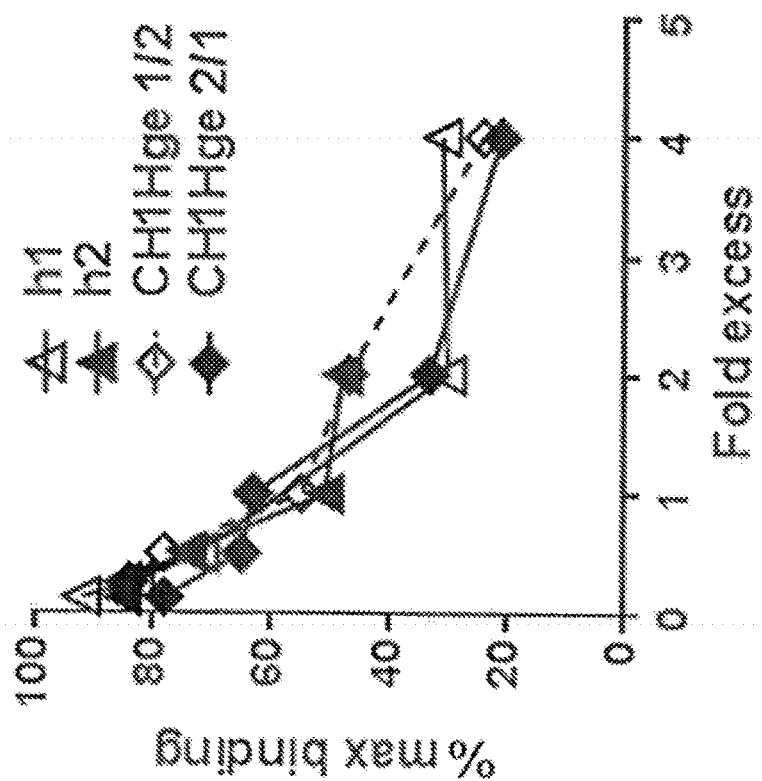
FIG. 14 contains control experiments validating that ChiLob 7/4 switch mutants bind similarly to CD40.

As the variable regions of the h1 and h2 ChiLob 7/4 mAb were identical and the activity of h2 was independent of its Fc domain, we examined the role of the CH1 and hinge domains of ChiLob 7/4 h2 in agonistic activity. To this end we produced mutants in which either the CH1 domain alone or both the CH1 and hinge domains of ChiLob 7/4 h1 and h2 were switched (FIG. 13A). Domain swapping did not interfere with antigen binding as assessed by flow cytometry (FIG. 14). Comparative agonistic activity of the different mAb was assessed by their ability to promote activation of human B cells and proliferation of hCD40 Tg B cells in vitro (FIG. 13A). When either the CH1 domain of h2 was replaced with that of h1 (CH1 1/2) or the CH1 of h1 was replaced with that of h2 (CH1 2/1) (FIG. 13A, (i) and (ii)) little B cell proliferation was seen and human B cells were not activated unless cells expressing high levels of FcγRIIB were provided to cross-link the mAb. Thus the presence of either the h2 CH1 domain alone (in CH1 2/1) or the h2 hinge region alone (in CH1 1/2) did not confer activity. Similarly, no activity was seen when both the CH1 and hinge of h2 was replaced with that of h1 (CH1Hge 1/2) (FIG. 13A (iii)). However, when the CH1 and hinge of h1 was replaced with that of h2 (CH1Hge 2/1) (FIG. 13A (iv)) robust human B-cell activation and proliferation of both FcγRIIB WT and KO hCD40 Tg B cells was observed similar to that seen with native h2. Similarly, in vivo, ChiLob 7/4 CH1Hge 2/1 produced significant increases in OVA-specific CD8 T-cell expansion whereas CH1Hge 1/2 was inactive (FIG. 13B). These data show that the unusual agonistic activity of h2 requires both its CH1 and hinge domains.

Human IgG2 Activity is Dependent Upon its Disulfide Bond Configuration.

IgG2 is unique amongst human IgG in its ability to 'shuffle' disulfide bonds in its CH1 and hinge regions (FIG. 18) resulting in a range of isoforms (Dillon et al., 2008; Martinez et al., 2008; Wypych et al., 2008; Zhang et al., 2010). The molecule is believed to be synthesized in its 'h2A' form, wherein the heavy chain (HC) Cys127 in CH1 is linked to Cys214 in the light chain (LC), which then gradually converts in the blood through a series of intermediates (Liu et al., 2008) to its 'h2B' form in which HC Cys127 and LC Cys214 form disulfide bonds with the HC hinge Cys232 and Cys233 (FIG. 18A). Importantly, physicochemical properties (Dillon et al., 2008), and electron microscopy (Ryazantsev et al., 2013), suggest that h2A has a classical IgG flexible 'Y' conformation, whereas h2B adopts a more compact shape with the Fab' arms held in close proximity to the hinge. The h2A and h2B forms can be distinguished by non-reducing capillary electrophoresis (nrCE-SDS; (Martinez et al., 2008)) where they are revealed as a double peak in unfractionated h2 compared to a single peak for h1 (FIG. 18B). Of the ChiLob 7/4 mAb mutants analyzed above, only CH1Hge 2/1 retained a double peak on nrCE-SDS (FIG. 18B), supporting our hypothesis that disulfide shuffling is important for agonistic activity.

To determine whether differentially disulphide-linked forms of ChiLob 7/4 were associated with different agonistic activities, two approaches were taken. First, chemical 'skewing' of ChiLob 7/4 in redox buffer in the presence or absence of denaturant was used to enrich for h2A or h2B, respectively (Dillon et al., 2008) (FIG. 15A, top panel). This resulted in markedly different activities, with much greater activation of hCD40Tg B cells with skewed h2B than h2A (FIG. 15A). Similar differences in B cell activation were observed when the skewed forms were added to human B cells (FIG. 16A), for skewed forms of the ChiLob 7/4 CH1Hge 2/1 mutant (FIG. 16B) and for the anti-mouse CD40 mAb 3/23 where 3/23 h2B was able to activate mouse B cells in soluble form whereas h2A required co-incubation with FcγRIIB expressing cross-linking cells (FIG. 15B; these cells express non-physiologically high levels of FcγRIIB (White et al., 2011) capable of cross-linking h2). The skewed h2B form of ChiLob 7/4 was also able to activate FcγRIIB KO B cells as both whole IgG (FIG. 15D (i)) or as a F(ab')$_2$ fragment (FIG. 16C), confirming its activity remained FcγR-independent. Second, mutagenesis was used to produce 'locked' h2A- and h2B-like forms as previously described (Allen et al., 2009; Martinez et al., 2008). HC C232S or C233S mutation of ChiLob 7/4 produced homogenous h2A mAbs as assessed by nrCE-SDS (FIG. 15C (HC C232S, HC C233S)) that did not stimulate hCD40 Tg mouse B-cell proliferation at any concentration tested over a wide range (FIG. 15D (ii) and (iii)), whereas the h2B-like HC C127S mutant (FIG. 15C (HC C127S)), showed increased activity relative to native h2 at high concentrations for both FcγRIIB WT and KO cells (FIG. 15D (iv)).

These combined data suggested that the FcγR independent agonistic activity of h2 is contingent upon the precise conformation of disulfide bonds in its hinge and CH1 domains, and specifically on its ability to adopt the more compact h2B form. Immune activation through CD40 ligation appears to require receptor clustering in the cell membrane to allow TRAF recruitment and propagation of downstream intracellular signals. Many of the effects are mediated through NFkB activation (Elgueta et al., 2009). Experiments with both primary hCD40Tg B cells (FIG. 15E) and transformed human Ramos B cells (FIG. 16D) revealed a much greater capacity of ChiLob 7/4 h2B to activate NFkB as reflected by greatly enhanced IkB phosphorylation after cell stimulation compared to h2A. This is consistent with an ability of the more compact h2B to promote clustering of CD40 in the membrane leading to NFkB signalling and cellular activation.

Mutagenesis Produces a Range of IgG2 Agonistic Activities.

Further studies revealed ChiLob 7/4 h2 could be manipulated to achieve a range of agonistic activities. Mutation of LC Cys214 to Ser prevented the LC-HC disulfide linkage resulting in two peaks on nrCE-SDS (FIG. 15C (LC C214S)). However, the mAb remained intact under nondenaturing conditions with no reduction in binding to CD40 as measured by SPR (FIG. 15F) or flow cytometry (FIG. 16E). LC C214S caused an increase in hCD40 Tg B-cell proliferation similar to that of the C127S mutant (FIG. 15D (i)). However, LC C214S combined with HC 232S gave a profile similar to that of native h2 where activity was greatly reduced at high concentrations (FIG. 15D (ii)), whereas LC C214S combined with HC C233S provided maximum activity similar to that of skewed h2B (FIG. 15D (iii) vs (i)). As noted herein, native ChiLob 7/4 (a mixture of isoforms) produced a characteristic 'bell' shaped concentration curve when used to stimulate B cells in vitro, in which B cell responses were lower at high concentrations (e.g., FIGS. 10D, 12B and 15D (i)). This effect was largely lost with pure h2B, where high concentrations remained fully active (FIG. 15D), but was recapitulated with a 1:1 mixture of h2A and h2B (FIG. 15G). Given the complete lack of response to the h2A form, this suggests h2A can block the activity of h2B, reducing its potency at high concentrations and suggesting that h2A possesses a certain level of antagonistic activity. Finally, differences in ChiLob 7/4 h2A and h2B activity were recapitulated in vivo, where h2B caused significantly greater expansion of both OVA-specific CD8 T cells (FIG. 15H) and OVA specific IgG (FIG. 15I) than h2A in hCD40Tg FcγRIIB KO mice. Similar differences in in vivo activity were observed for h2A and h2B skewed forms of the CH1Hge 2/1 mutant (FIGS. 16F and 16G). In conclusion our data demonstrate that manipulation of the disulfide structure of h2 may enable the production of therapeutic agents with defined and diverse immunostimulatory function that, importantly, is independent of the presence of FcγR in target tissue.

The experiments which were conducted are further described in the Examples and the Materials and Methods used therein which are described in detail below.

EXAMPLES

Materials and Methods Used in Examples 1-7

Mice

C57Bl/6 and RAG$^{-/-}$ mice were from Charles River Laboratories (Kent, UK). Other genetically altered strains (all on C57BL/6 background) were C57BL/6 FcγRIIB$^{-/-}$, OTI TCR transgenic (from Dr. Matthias Merkenschlager, Imperial College, London) and human CD40 transgenic (hCD40 Tg) were from Randolph Noelle (Kings College, London). Human CD40 Tg/FcγRIIB$^{-/-}$ mice were obtained by crossbreeding with genotypes confirmed by flow cytometry. Animals were bred and housed in a local animal facility and were used at approximately 8-12 weeks of age. All experiments were carried out according to local ethical committee guidelines under UK Home Office license numbers PPL30/2451 and PPL30/2964.

Antibodies and Reagents

The following hybridomas were used: anti-human CD23 (MHM6) was from J Gordon (University of Birmingham). Anti-human FcγRII (AT10), that binds both FcγRIIA and IIB (33), anti-human CD40 (LOB7.4; (22)) and anti-human 4-1BB were produced in house using conventional hybridoma technology. Anti-mouse CD19-PE (clone 1D3), anti-human CD19-PE (clone RFB9) were from AbDSerotec (Oxford, UK). Anti-mouse CD23-PE was from BD Biosciences. For OTI cell staining APC-labelled anti-CD8a (clone 53-6.7; BD Biosciences), and PE labelled SIINFEKL tetramers produced in house as described previously (12) were used. Flow cytometry was performed using a FACS Caliber (BD Biosciences). Chicken ovalbumin (OVA) was purchased from Sigma-Aldridge (Poole, UK). Endotoxin-free OVA was from Profos AG (Regensberg, Germany).

Chimeric Antibodies

DNA constructs encoding heavy and light chain variable regions of various antibodies were either amplified from hybridoma by PCR reactions or synthesized by Genewiz, Inc. SGN40-Soton and TGN1412-Soton were produced using published sequences (US patent numbers WO 2007/075326 and U.S. Pat. No. 7,585,960). Variable regions were subcloned into expression vectors (pEE6.4 vector for heavy chain and pEE12.4 vector for light chain, Lonza) containing constant regions of different antibody isotypes. Heavy and light chain vectors were further subcloned together before transfection into 293F cells for transient production or CHO-K1 cells for stable production of antibodies. Secreted antibody was purified by Protein A-Sepharose (Sigma-Aldrich) chromatography and aggregates removed by gel filtration through Sephadex 200 (Sigma-Aldrich). All preparations were endotoxin low (<1 ng/mg protein) as determined by an Endosafe-PTS portable test system (Charles River Laboratories).

Immunization and Assessment of Immune Responses

Mice were immunized as detailed for individual experiments via tail vein injection in 200 µL saline. Serum anti-OVA Ab levels were determined by ELISA (34). In some experiments, $3 \times 10^5$ splenic OVA-specific splenic CD8 (OTI) T cells were given via tail vein the day before immunization. OTI cell preparations were depleted of B cells prior to injection using anti-CD19-PE and anti-PE microbeads (Miltenyi Biotech).

Tumor Therapy

For vaccination against the OVA-expressing tumor, EG7, mice were adoptively transferred with $5 \times 10^4$ OTI cells on D−6 then received 0.5 mg Sigma OVA+100 µg anti-CD40 mAb on D−5. The mice were challenged with $5 \times 10^5$ EG7 tumor cells subcutaneously on DO. Tumor growth was monitored and mice sacrificed when the humane endpoint was reached (tumor >1.5 cm in any direction). B cell lymphoma (BCL1) therapies were performed as described previously (18).

Cell Activation and Proliferation

Dendritic Cells:
For microscopy, spleens were harvested from RAG$^{-/-}$ mice 2 days after i.v. injection with 100 µg anti-CD40 mAb and sections stained for CD70 and MIDC8 as previously described (12). Human primary Langerhans cells (LCs) were isolated as described previously (35). Briefly, skin specimens were acquired from healthy individuals after obtaining informed written consent with approval by the Southampton and South West Hampshire Research Ethics Committee in adherence to Helsinki Guidelines. Epidermal sheets were separated following 20 h enzymatic digestion (Disopase,2 IU, Gibco, UK). LCs were harvested following 48 h migration from epidermal sheets, and enriched to >70% CD1a+ HLADR+ cells by Optiprep™ density gradient (Axis Shield, Norway). Cells were plated into 96 U-bottom plates at $5 \times 10^4$ cells/well in RPMI 1640 (Gibco, UK) supplemented with Penicillin/Streptomycin (1%, Sigma, UK) and FBS (10%, Invitrogen, UK) and stimulated with LOB7.4 human IgG1 or human IgG2 antibodies or isotype control (0.001 µg/ml-10 µg/ml) for 18 h. Expression of activation markers (CD40, CD86, CD70, BD Biosciences, UK) on CD1a+ HLADR+(BD Biosciences, UK) LC was assessed by flow cytometry.

B Cells:
B cells were purified from spleen (mouse) or peripheral blood monocytic cells (PBMC, human) using magnetic negative selection kits (Miltenyi Biotech or StemCell Technologies). Human PBMC (lymphoprep, Axis-Shield) were isolated from blood cones obtained from anonymous healthy donors through the National Blood Service (Southampton General Hospital). Cells were plated into 96-well round-bottom dishes at $1 \times 10^5$ cells/well with various concentrations of mAb as described for individual experiments. For human cells, cultures with and without recombinant human IL-4 (20 ng/ml) were used. In some cases, $1 \times 10^5$ 293 cells transfected with human FcγR were also added. Transfections were performed as previously described (White et al (2011)). To assess activation, cells were photographed (Olympus CKX41 microscope with CC12 soft imaging system) after overnight incubation and activation marker expression analyzed by flow cytometry (FACSCalibur, BD Biosciences). Proliferation was assessed by [methyl-$^3$H] thymidine (PerkinElmer, Cambridge, UK) incorporation after 5 (mouse) or 8 (human) days of culture, as described (White et al., (2011)).

T Cells:
Human PBMCs were labelled with 2 mM CFSE and then pre-cultured for 2 days at high density in 24-well plates as described (36), with 1.5 ml of cells at $1 \times 10^7$/ml per well. Pre-cultured cells were washed and resuspended at $1 \times 10^6$/ml for the assay. For some experiments T cells were isolated from pre-cultured PBMCs using a total T-cell isolation kit (Miltenyi Biotec). For the anti-h4-1BB mAbs, wells of 96-well round-bottomed plates were coated with 0.02 µg/ml OKT3 in PBS for 4 h, then washed twice and $10^5$ PBMCs/well incubated with 5 µg/ml mAb (final volume 150 µl) for 5 days. Proliferation of CD4$^+$ cells was assessed by flow cytometric analysis of CFSE dilution. For the anti-CD28 mAbs, $10^5$ isolated T cells were incubated with mAb in uncoated wells and proliferation assessed as above. Results are expressed as the percentage of divided cells.

Surface Plasmon Resonance

A Biacore T100 was used to assay the interaction between soluble Fcγ receptors and 3/23 and LOB7.4 mAb isotypes. Antibodies or BSA as a control were immobilized at high (15,000 RU) and low (1,000 RU) densities to the flow cells of CM5 sensor chips (Biacore) by standard amine coupling according to the manufacturer's instructions. Soluble Fc receptors (FcγRI, IIA, IIB, IIIA and IIIB, R and D Systems, Abingdon, UK) were injected through the flow cell at 200, 100, 50, 25, 12.5 and 6.25 nM (50 nM point in duplicate) in HBS-EP running buffer (Biacore) at a flow rate of 30 µL/min. Soluble Fc receptors were injected for 5 min and dissociation was monitored for 10 min. Background response for the control flow cell was subtracted automatically.

Statistical Analyses

Students T-tests (unpaired) were performed using Graph-Pad' Prism software (GraphPad™ Software, inc., La Jolla, Calif.). For comparison of Ab responses, data were log-transformed before analysis. Significance was accepted when p<0.05 log-transformed before analysis. Significance was accepted when p<0.05.

Example 1

Example 1 relates to the experiments in FIG. 1(a)-(f) showing that human IgG2 imparts FcγR independent agonistic activity to the anti-hCD40 mAb, LOB7.4. Panel (a) shows the results experiments wherein purified hCD40 Tg mouse splenic B cells which were incubated with LOB7.4 mAb of the indicated isotypes at 200 ng/ml. B cell activation was assessed by cell clumping (top) and CD23 upregulation (middle; filled grey histograms, untreated controls, black line treated cells) after overnight incubation and $^3$H thymidine incorporation (bottom; mean+/−SE of triplicate samples) as a measure of proliferation. Data from 1 of 7 experiments shown. Panels (b and c) show results wherein hCD40 Tg mice were immunized with 0.5 mg Sigma OVA+100 μg of the indicated mAb. Circulating SIINFEKL-specific endogenous CD8+ T cells (b) and anti-OVA Ab (c) were determined 8 and 14 days later, respectively. Combined data from 2 experiments (n=7) is shown. Panel (d) shows the results of experiments wherein hCD40 Tg B cells were analyzed as in (a) after incubation with LOB7.4 h1 and h2 whole IgG, Fab'$_2$ or Fab' fragments for 16 h at 1 μg/ml. (1 of 5 experiments shown) Panel (e) shows the results of experiments wherein hCD40Tg B cells that were FcγRIIB$^{+/+}$ (WT) or FcγRIIB$^{-/-}$ (KO) were incubated with the indicated LOB7.4 mAb at 1 μg·ml and analyzed as in (a). Results from 1 of 5 experiments shown. (f) hCD40 Tg mice that were FcγRIIB$^{+/+}$ (WT) or FcγRIIB$^{-/-}$ were adoptively transferred with OTI cells then immunized with 100 ? g Sigma OVA+ 100 μg of the indicated LOB7.4 mAb. Circulating OTI cells were enumerated 5 days later. Values are mean+/−SD for triplicate mice. Results from 1 of 2 experiments shown.

Example 2

This example relates to the experiments in FIG. 2 which show that human IgG2 imparts FcγR-independent activity to other anti-TNFRSF mAb. Panel (a) contains the results of experiments wherein human B cells were incubated with the anti-hCD40 mAb SGN40-Soton h1 or h2 and activation and proliferation assessed as in FIG. 1(a). Panel (b) contains the results of experiments wherein hCD40 Tg B cell proliferation (WT or FcγRIIB$^{-/-}$) in response to SGN40 h1 and h2 or SC26 m1 (SGN40 parent mAb) at 200 ng/ml was assessed as in FIG. 1(e). Results from 1 of 2 experiments shown. Panel (c) contains the results of experiments wherein human T cell proliferation in response to chimeric h1 and h2 anti h4-1BB in PBMC cultures or anti-hCD28 in purified T cell cultures. Isotype-treated controls (C) are shown for comparison. Photos in the lower panel are of purified T cells treated with anti-CD28 h1 and h2.

Example 3

This example relates to the experiments in FIG. 3(a)-(d) which show that the h2 $C_H1$ and hinge regions impart FcγR-independent agonistic activity to LOB7.4. Panels (a and b) contain (top) schematics of LOB7.4 h1 and h2 mAb either native (a) or where the $C_H1$ ($C_H1$ 1/2 and $C_H1$ 2/1) or $C_H1$ and hinge regions (Hinge 1/2 and Hinge 2/1) have been swapped (b). In the middle of these panels CD23 expression on human B cells is shown after overnight incubation with the indicated mAb (black line) compared to unstimulated cells (grey histogram). In the bottom of these panels hCD40 Tg FcγRIIB$^{+/+}$ (WT) or FcγRIIB$^{-/-}$ (KO) B cell proliferation was assessed by $^3$H thymidine incorporation in response to various concentrations of the chimeric mAb. In (a) proliferation in response to LOB7.4 h1, h2 and m1 is compared. (c) hCD40 Tg mice were adoptively transferred with OTI cells then immunized with 0.5 mg Sigma OVA plus 100 μg of LOB7.4 h1 or h2 or chimeric Hinge 1/2 or Hinge 2/1 as indicated. Circulating OTI cells (mean+/−SD, n=6 combined from 2 experiments) at the peak of the response (day 5) are shown. *p<0.05 **p<0.01. (D) CE-SDS profiles of LOB7.4 h1, h2 and the chimeric mAb.

Example 4

This example relates to the experiments in FIG. 4 (a)-(e) showing that the agonistic activity of LOB7.4 h2 is dependent upon its ability to adopt its h2B conformation. Panel (a) contains CE-SDS profiles and shows hCD40 Tg B cell proliferation in response to LOB7.4 native h2, or h2 chemically skewed towards its h2A ('A' skew) and h2B ('B' skew) forms. The results of 1 of 2 experiments are shown. Panel (b) contains CE-SDS profiles of LOB7.4 mAb with the indicated point mutations. The LC C214S mutation prevents covalent linkage of the HC and LC and these forms therefore separate on electrophoresis. The positions of whole IgG, HCHC complexes (HH), free LC (L) and an internal 10 kDa marker are indicated. Panel (c) shows the proliferation of FcγRIIB$^{+/+}$ (WT) or FcγRIIB (KO) hCD40 Tg B cells in response to various concentrations of the manipulated LOB7.4 mAb. (Results from 1 of at least 3 experiments are shown). Panel (d) shows the proliferation of hCD40 Tg B cells, in response to native LOB7.4 h2, h2A (HC C233S), skewed h2B, or a 1:1 mixture of h2A:h2B. (Data from 1 of >5 similar experiments is shown). Panel (e) shows SPR profiles of the indicated LOB7.4 h2 mutants binding to immobilized hCD40. The mAb concentrations used were: 100, 20, 4, 0.8 and 0.16 nM, hCD40~8000 RU. Similar results were obtained at 1200 RU hCD40.

Example 5

This example relates to the experiments in FIG. 5 (a)-(e) showing the isotype dependence of the anti-mouse CD40 mAb, 3/23. Panels (a and b) contain experimental results wherein mice were adoptively transferred with OTI cells then immunized with 500 μg Sigma OVA or 100 μg endoOVA without (Con) or with 100 μg of the indicated 3/23 mAb. In (a) and (b) circulating OTI cells and anti-OVA Ab concentrations were respectively measured 5 and 14 days later. Results are Mean+/−SD for triplicate mice and represent 1 of 5 (Sigma OVA) or 3 (endo OVA) experiments. (*p<0.05 **p<0.01). Panel (c) contains experiments wherein splenic sections of ice administered 100 μg of the indicated 3/23 isotypes were stained for CD70 (green, left) and the DC marker MIDC8 (red, middle; merge on right). (Bar=100 μm). Panel (d) shows an experiment wherein C57BL/6 ice were adoptively transferred with OTI cells, immunized with OVA+100 μg of the indicated mAb and five days later challenged with EG7 tumor subcutaneously. Survival curves for groups of 5 mice from 1 of 2 experiments are shown. Curves for m1 and h2 overlay each other. (e) BALB/c mice were injected i.v. with 1×10$^4$ BCL$_1$ tumor cells. Fourteen days later, when the tumor represented 5-10% of total splenocytes, mice received a single 100 μg i.

v. dose of 3/23 h1 or h2 or PBS (control) as indicated. Survival for groups of 5 mice from 1 of 2 experiments is shown.

Example 6

This example relates to the experiments in FIG. 6(a)-(e) demonstrating that LOB7.4 human IgG2 is more active than human IgG1 on human cells and is independent of FcγR interaction. Panel (a) shows an experiment wherein purified human peripheral blood B cells were incubated with LOB7.4 h1 or h2 at 1 μg/ml and cell activation and proliferation analyzed as in FIG. 1(a), except that proliferation was assessed after 8 days. The results of 1 of >10 separate experiments is shown. Panel (b) contains an experiment wherein human skin derived Langerhans cells were incubated with LOB7.4 h1 or h2 or isotype control mAb for 18 h and CD70 expression analyzed by flow cytometry. (Results from 1 of 2 experiments are shown). (*$p<0.05$ **$p<0.01$). Panel (c) shows surface plasmon resonance (SPR) sensograms of LOB7.4 h1 and h2 binding to human FcγR. Similar results were obtained with mAb immobilized at 1,000 or 15,000 RU. Panel (d) shows an experiment wherein CFSE-labeled human B cells were incubated with LOB7.4 h1 or h2 plus untransfected 293 cells (Con) or cells expressing high levels of the indicated human FcγR. B cell proliferation was assessed by flow cytometric analysis of CFSE dilution after 8 days. Grey histograms represent unstimulated cells. Panel (e) shows an experiment wherein isolated human B cells were incubated with LOB7.4 h1 or h2 for 16 h in the presence or absence of a 50-fold excess of AT10 Fab'$_2$ and/or 293 cells expressing high levels of hFcγRIIA as indicated. CD23 expression (black line) was compared to unstimulated cells (grey histogram).

Example 7

This example relates to the experiments in FIG. 7(a)-(d) which demonstrate the antagonistic and agonistic properties of h2A and h2B. Panel (a) shows nrCE-SDS profiles of native 3/23 h2, or h2 chemically skewed towards its h2A and h2B forms. Panel (b) shows the upregulation of CD23 expression on mouse B cells incubated with native or skewed forms of 3/23 h2 in the absence or presence of FcγRIIB-expressing cross-linking cells. (One of 3 experiments is shown). Panel (c) shows the proliferation of mouse B cells in response to the indicated concentrations of 3/23 h2A and h2B. Panel (d) shows the proliferation of hCD40 Tg B cells either WT or FcγRIIB KO, in response to SGN40-Soton h2 alone or mixed 1:1 with LOB7.4 HC C233S (h2A). (Mean and range of duplicate samples from 1 of 2 experiments is shown).

The following methods and materials were used in the experiments described in examples 8-16.

Materials and Methods

Mice

C57Bl/6 and RAG−/− mice were from Charles River Laboratories (Kent, UK). Other genetically altered strains (all on C57BL/6 background) were FcγRIIB−/− (Boross et al., 2011), OTI TCR transgenic (kindly provided by Dr. Matthias Merkenschlager, Imperial College, London) and human CD40 transgenic (hCD40 Tg) kindly provided by Randolph Noelle (Kings College, London) (Ahonen et al., 2002). Human CD40 Tg/FcγRIIB−/− and g chain−/− mice were generated by crossbreeding with genotypes confirmed by flow cytometry. Animals were bred and housed in a local animal facility and were used at approximately 8-12 weeks of age. All experiments were carried out according to local ethical committee guidelines under UK Home Office license numbers PPL30/2451 and PPL30/2964.

Antibodies and Reagents

The following hybridomas were used: anti-human CD23 (MHM6) was from J Gordon (University of Birmingham). Anti-human Fc☒ nti-human Fc)3 (MHM6) was from γRIIA and IIB (Greenman et al., 1991), anti-human FcγRIIB (KB61), anti-human CD40 (ChiLob 7/4; (Chowdhury, 2014)) and antihuman 4-1BB were produced in house using conventional hybridoma technology. Anti-mouse CD23-PE was from BD Biosciences. For OTI cell staining, APC-anti-mouse CD8a (clone 53-6.7; BD Biosciences), and PE labelled SIINFEKL tetramers produced in house as described previously (White et al., 2011) were used. Flow cytometry was performed using a FACS Calibur (BD Biosciences). Chicken ovalbumin (OVA) was from Sigma-Aldridge (Poole, UK). Endotoxin-free OVA was from Profos AG (Regensberg, Germany).

Chimeric Antibodies

DNA constructs encoding heavy and light (kappa) chain variable regions of various mAbs were either amplified from hybridoma by PCR reactions or synthesized by Genewiz, Inc. The anti-CD40 mAb SGN40-Soton and the anti-CD28 TGN-Soton were produced using published sequences (US patent numbers WO 2007/075326 and U.S. Pat. No. 7,585,960 respectively). Details of mAb purification and quality control methods can be found in Supplemental Experimental Procedures

Immunization and Assessment of Immune Responses

Mice were immunized as detailed for individual experiments via tail vein injection in 200 μL PBS. Serum anti-OVA Ab levels were determined by ELISA (White et al., 2010). In some experiments, 3×10$^5$ splenic OVA-specific CD8 (OTI) T cells were given via tail vein the day before immunization.

Tumor Therapy

For vaccination against the OVA-expressing thymoma, EG7, mice were adoptively transferred with 5×10$^4$ OTI cells on day−6 then received 0.5 mg Sigma OVA 100 mg anti-CD40 mAb on day−5. The mice were challenged with 5×10$^5$ EG7 tumor cells subcutaneously on day 0. Tumor growth was monitored and mice sacrificed when the humane endpoint was reached (15 mm mean tumor diameter when taking the two greatest perpendicular measurements). B-cell lymphoma (BCL1) therapies were performed as described (White, 2014). Briefly, mice were inoculated via tail vein with 1×10$^4$ BCL$_1$ cells on day 0. On day 14 (when the tumor was well established and represented 5-10% spleen weight) mice were treated with a single 100 μg dose of anti-CD40.

Cell Activation and Proliferation

Details of the isolation and assays to assess the activation and/or proliferation of dendritic cells, B cell and T cells are described infra.

Surface Plasmon Resonance

A Biacore T100 (GE Healthcare) was used to assay the interaction between soluble Fcγ receptors and ChiLob7/4 mAb isotypes, as well as between soluble mAb and immobilized CD40, as described infra.

Statistical Analyses

Students T-tests (unpaired, two-tailed) and survival analyses (Log-rank Mantel-Cox tests) were performed using GraphPad™ Prism software (GraphPad™ Software, inc., La Jolla, Calif.). For comparison of Ab responses, data were log-transformed before analysis. In some cases data from multiple experiments were combined. However, this was not always possible as although relative differences remained the same between experiments, absolute measures often varied too much to allow combination. When this was the case, a single representative experiment is shown with the number of experiments performed stated in the figure legend.

Chimeric Antibody Production and Quality Control

Variable regions were subcloned into expression vectors (pEE6.4 vector for heavy chain and pEE12.4 vector for light chain, Lonza) containing constant regions of different antibody isotypes. Heavy and light chain vectors were further subcloned together before transfection into 293F cells for transient or CHO-K1 cells for stable production of mAbs. Secreted mAb was purified by Protein A-Sepharose (Sigma-Aldrich) chromatography and aggregates (as revealed by SEC-HPLC) removed by gel filtration through Sephadex 200 (Sigma-Aldrich). All preparations were endotoxin low (<1 ng/mg protein) as determined by an Endosafe-PTS portable test system (Charles River Laboratories). Contaminating endotoxin could not account for the mAb functions described in this study as i) mAb concentrations of >10 mg/ml would be required to provide enough endotoxin to cause mouse B cell proliferation in vitro (FIG. 9A); ii) human B cells do not respond to endotoxin in vitro (Bourke et al., 2003) and FIG. 9B), but do show isotype dependent differences in activation with ChiLob 7/4; iii) a dose of at least 50 mg of mAb (500-fold that given) would be required to provide enough endotoxin to boost immune responses to this level in vivo (FIG. 9C).

Flow cytometry and/or SPR were used to assess differences in Ag binding. Non-reducing denaturing capillary electrophoresis (nrCE-SDS) of mAb preparations was performed using a chemically reduced to produce Fab' as described (Glennie et al., 1987). Protein A chromatography was used to remove any residual Fc.

Cell Isolation, Activation and Proliferation

Dendritic Cells:

Human primary Langerhans cells were isolated as described previously (Polak et al., 2012). Briefly, skin specimens were acquired from healthy individuals after obtaining informed written consent with approval by the Southampton and South West Hampshire Research Ethics Committee in adherence to Helsinki Guidelines. Epidermal sheets were separated following 20 h enzymatic digestion (Disopase, 2 IU, Gibco, UK). LCs were harvested following 48 h migration from epidermal sheets, and enriched to >70% CD1a+ HLADR+ cells by Optiprep™ density gradient (Axis Shield, Norway). Cells were plated into 96 well U-bottom plates at $5 \times 10^4$ cells/well in RPMI 1640 (Gibco, UK) supplemented with Penicillin/Streptomycin (1%, Sigma, UK) and FBS (10%, Invitrogen, UK) and stimulated with ChiLob 7/4 human IgG1 or human IgG2 mAbs or isotype control for 18 h. Expression of activation markers CD40, CD86, CD70 on CD1a+ HLADR+ (all BD Biosciences) LC was assessed by flow cytometry.

B Cells:

B cells were purified from spleen (mouse) or peripheral blood mononuclear cells (PBMC, human) using magnetic negative selection kits (Miltenyi Biotech or StemCell Technologies). Human PBMC (Lymphoprep, Axis-Shield) were isolated from blood cones obtained from anonymous healthy donors through the National Blood Service (Southampton General Hospital). Cells were plated into 96-well round-bottom dishes at $1 \times 10^5$ cells/well with various concentrations of mAb as described for individual experiments. In some cases, $1 \times 10^5$ 293F cells transfected with human FcγR Beckman PA800 Plus analyser according to the manufacturer's instructions. To produce skewed forms of h2, mAb were dialyzed into 0.2 M Tris pH 8.0 containing 6 mM cysteine plus 1 mM cystamine with (for h2A) or without (for h2B) 2 M guanidine hydrochloride, for 4 days at 40° C., then dialyzed into PBS before use. Pepsin digestion was used to make (Fab')2 fragments that were then chemically reduced to produce Fab' as described (Glennie et al., 1987). Protein A chromatography was used to remove any residual Fc.

Cell Isolation, Activation and Proliferation

Dendritic cells:

Human primary Langerhans cells were isolated as described previously (Polak et al., 2012). Briefly, skin specimens were acquired from healthy individuals after obtaining informed written consent with approval by the Southampton and South West Hampshire Research Ethics Committee in adherence to Helsinki Guidelines. Epidermal sheets were separated following 20 h enzymatic digestion (Disopase, 2 IU, Gibco, UK). LCs were harvested following 48 h migration from epidermal sheets, and enriched to >70% CD1a+ HLADR+ cells by Optiprep™ density gradient (Axis Shield, Norway). Cells were plated into 96 well U-bottom plates at $5 \times 10^4$ cells/well in RPMI 1640 (Gibco, UK) supplemented with Penicillin/Streptomycin (1%, Sigma, UK) and FBS (10%, Invitrogen, UK) and stimulated with ChiLob 7/4 human IgG1 or human IgG2 mAbs or isotype control for 18 h. Expression of activation markers CD40, CD86, CD70 on CD1a+ HLADR+ (all BD Biosciences) LC was assessed by flow cytometry.

B cells:

B cells were purified from spleen (mouse) or peripheral blood mononuclear cells (PBMC, human) using magnetic negative selection kits (Miltenyi Biotech or StemCell Technologies). Human PBMC (Lymphoprep, Axis-Shield) were isolated from blood cones obtained from anonymous healthy donors through the National Blood Service (Southampton General Hospital). Cells were plated into 96-well round-bottom dishes at $1 \times 10^5$ cells/well with various concentrations of mAb as described for individual experiments. In some cases, $1 \times 10^5$ 293F cells transfected with human FcγR (White et al., 2011) were also added. To assess activation, cells were photographed (Olympus CKX41 microscope with CC12 soft imaging system) after overnight incubation and activation marker expression analyzed by flow cytometry (FACSCalibur, BD Biosciences). Proliferation was assessed by [methyl-$^3$H] thymidine (PerkinElmer, Cambridge, UK)

incorporation after 5 (mouse) or 8 (human) days of culture, as described (White et al., 2011).

T cells:

Human PBMCs were labelled with 2 mM CFSE and then pre-cultured for 2 days at high density in 24-well plates as described (Romer et al., 2011), with 1.5 ml of cells at 1×10$^6$/ml per well. Pre-cultured cells were washed and resuspended at 1×10$^6$/ml for the assay. For some experiments T cells were isolated from pre-cultured PBMCs using a total T-cell isolation kit (Miltenyi Biotec). For the anti-h4-1BB mAbs, wells of 96-well round-bottomed plates were coated with 0.02 mg/ml OKT3 in PBS for 4 h, then washed twice and 10$^5$ PBMCs/well incubated with 5 PBMCs/well incubated with 5 or 4 h, then. Proliferation of CD4$^+$ cells was assessed by flow cytometric analysis of CFSE dilution. For the anti-CD28 mAbs, 10$^5$ isolated T cells were incubated with mAb in uncoated wells and proliferation assessed as above. Results are expressed as the percentage of divided cells.

For activation of EBV-peptide specific CD8$^+$ human T lymphocytes; HLA-A2 restricted T cells specific for the BMLF-1 epitope of EBV (GLCTLVAML; Cambridge Peptides, UK) were expanded from HLA-A2 individuals as described (Polak et al., 2012). Human primary Langerhans cells (LCs) were incubated with an extended long peptide containing BMLF-1 (proGLC: FNNFTVSFWLRVPKVSASHLEGLCTLVAML, 10 μM) for 6 h and stimulated with ChiLob 7/4 h1 or h2 mAb or isotype control, 100 ng/ml for 18 h. Pulsed and washed LCs (1×10$^4$ cells) were co-cultured with BMLF-1-specific T cells (5×10$^4$ cells) for 20 hours in an ELISpot assay for IFN-γ production (Mabtech, Sweden) as per manufacturer's protocol. Spot forming units (sfu) were enumerated with ELISpot 3.5 reader.

Surface Plasmon Resonance

A Biacore T100 (GE Healthcare) was used to compare the relative interactions between soluble Fcγ receptors and ChiLob7/4 mAb isotypes. Antibodies or BSA as a reference were immobilized at 15,000 RU to CM5 sensor chips (Biacore) by standard amine coupling according to the manufacturer's instructions. Use of an isotype control mAb to coat the reference flow cell was ruled out due to the presence of Fc. Soluble FcγR (R and D Systems, Abingdon, UK) were injected through the flow cell at 100 nM in HBS-EP+ running buffer (Biacore) at a flow rate of 30 μL/min at 25° C. Regeneration was performed for 30 seconds with 10 mM glycine, pH 2. The integrity of the mAb coated onto the flow cells was checked by using positive (hCD40-Fc) and negative (hOX40-Fc) control fusion proteins (R and D systems) at 100 nM (FIG. 11C). The background response for the reference flow cell was subtracted automatically; binding to the reference cell was negligible for all FcγR (FIG. 11D and data not shown). The integrity of each of the purified FcγR proteins was confirmed by at least one of the following: expected binding profiles for IgG isotypes (White et al., 2011, White et al., 2011) and this study); increased binding to mAb with mutated Fc known to enhance FcγR interaction (not shown); binding by immobilised anti-Fc interaction (not shown); bin FcγR (not shown and FIG. 11E). Conditions for the comparison of the interaction between the different anti-CD40 mAb and immobilized hCD40 were as follows: for comparison of Fab' binding hCD40-Fc (R and D Systems) was immobilized at pH5 at 1000 RU as above and Fab' fragments passed over at 640, 128, 25.6, 5.12 and 1.024 nM (FIG. 11E); for comparison of IgG binding, hCD40-Fc was immobilized at 8000 RU and IgG passed over at 100, 20, 4, 0.8 and 0.16 nM (FIG. 11F). Regeneration was performed for 30 seconds with 10 mM glycine, pH 1.5. Affinities of ChiLob 7/4 h1 and h2 Fab' fragments for CD40 were determined using Biacore Evaluation Software fitting a 1:1 binding model.

Example 8

This example relates to the experiments in FIG. 8 (a)-(h). These experiments show the effects of different human isotypes on anti-CD40 activity. (A) Activation of human B cells in response to ChiLob 7/4 of the indicated isotypes (1 μg/ml) was assessed after 16 h by homotypic adhesion (top) and 3H thymidine incorporation. Points represent individual samples from 2-5 experiments per isotype. (13) Human Langerhans cells were untreated (black line) or incubated (grey line) with ChiLob 7/4 h1, h2 or isotype control (c) for 18 h and CD70 expression analyzed by flow cytometry; 1 of 2 experiments shown. (C) IFN-γ ELISpot assay of BMLF-1-specific CD8$^+$ T-cell activation by HLA-matched human Langerhans cells activated with ChiLob 7/4 as in (B). Data representative of 2 experiments in triplicate normalized to activation by unpulsed cells. (D) Activation of hCD40 Tg B cells by ChiLob 7/4 h1 and h2 at 200 ng/ml was analyzed as in (A). Points are individual samples from 3 experiments performed in duplicate. (E) hCD40 Tg mice were immunized with 100 μg OVA with or without (Con) 100 μg of the indicated ChiLob 7/4 mAb. Circulating endogenous OVA-specific CD8$^+$ T cells were enumerated day 8, the peak of the response (left) and anti-OVA Ab (right) was determined on day 14. Individual animals from 2 of 4 experiments shown. (F) Mice (n=3) adoptively transferred with OTI cells were immunized with 100 g endotoxin-free OVA without (Con) or with 100 μg of the indicated 3/23 mAb. Circulating OTI cells were enumerated at the peak of the response (day 5; left) and anti-OVA Ab at day 14 (right). Combined data from 2 of >5 experiments. (G) C57Bl/6 mice (n=5) were adoptively transferred with OTI cells, immunized with OVA plus 100 μg of the indicated 3/23 isotypes and 5 days later challenged with EG7 tumor subcutaneously. Survival curves from 1 of 2 experiments shown. (H) BALB/c mice (n=5) were challenged i.v. with BCL1 tumor cells and 14 days later (when the tumor represented 5-10% spleen weight (White, 2014)) given 100 μg i.v. 3/23 h1, h2 or PBS (Con) as indicated. Survival curves from 1 of 2 experiments shown. *p<0.05, p<0.01, *p<0.001.

Example 9

This example relates to the experiments in FIG. 9 (a)-(g) which are control experiments validating the isotype effects on anti-CD40 activity of experiments in FIG. 8. Control experiments for isotype effects on anti-CD40 activity. (A-C) Endotoxin contamination does not explain anti-CD40 activity. (A) FcγRIIB−/− mouse B cells were incubated with increasing concentrations of LPS in the presence or absence of 400 ng/ml 3/23 m2a. Proliferation was assessed by 3H thymidine incorporation (mean+/−SEM triplicates). (B) Human B cell activation assessed by CD23 upregulation (black line compared to control, grey) after 16 h incubation with 1 mg/ml LPS in the presence or absence of 1 mg/ml ChiLob 7/4 h1 and/or FcγRIIB over-expressing cross-linking cells as indicated. (C) Mice were immunized with 100 mg endotoxin free OVA plus the indicated dose of LPS. Circulating anti-OVA Ab titers were determined on day 14. (D) Human ChiLob 7/4 isotypes bind similarly to CD40.

Purified hCD40Tg mouse B cells were incubated with 10 mg/ml ChiLob 7/4 h1-FITC pre-mixed with different concentrations of competing unlabeled ChiLob mAb of different human isotypes. Flow cytometry was used to determine the level of ChiLob 7/4-FITC binding and is expressed as the % maximum MFI (no competing mAb present). A non-targeted human IgG4 isotype mAb (grey triangles) was included as a noncompeting control. (E) ChiLob 7/4 h1 and h2 Fab' fragments have similar affinity for hCD40. hCD40 was immobilized at 1000 RU and ChiLob 7/4 h1 (solid line) or h2 (broken line) Fab' fragments flowed over the chip at 640, 128, 25.6 and 1.024 nM. Affinities were calculated by fitting a 1:1 binding model and were 10.0 and 10.2 nM h1 and h2, respectively. (F) Isotype controls for human and mouse CD40 mAb. Purified WT (mCD40+/+) or hCD40Tg/ mCD40 KO (mCD40−/−, hCD40+/−) mouse B cells were incubated for 16 h with the indicated mAb at 1 mg/ml. B-cell activation was assessed by homotypic adhesion (top) and CD23 upregulation (bottom): filled grey histograms, untreated cells; black line, treated with mAb alone; blue line, incubated with mAb+FcγRIIB over-expressing cross-linking cells. (G) Isotype-specific upregulation of CD70 on mouse splenic DC. Splenic sections from mice administered 100 mg of the indicated 3/23 isotypes stained for CD70 (green, left) and the DC marker MIDC8 (red, middle; merge on right). Bar=100 mm. Results from 1 of 2 experiments are shown.

Example 10

This example relates to the experiments in FIG. 10 (a)-(e) the results of which show the FcγR-independent activity of human IgG2. (A) Activation of human B cells by ChiLob 7/4 h1 or h2+/−a 50-fold excess of blocking anti-FcγRII (AT10) F(ab')$_2$ and/or hFcγRIIB over-expressing 293F cells (+/− FcγRII) as indicated. CD23 expression (black line) is compared to unstimulated cells (grey histogram). (B) Activation (homotypic adhesion and CD23 upregulation, top) and proliferation (bottom) of human B cells by ChiLob 7/4 h1 and h2 whole IgG, F(ab')$_2$ or Fab' for 16 h at 1 mg/ml. Mean and range of duplicate samples from 1 of 4 experiments. (C) Proliferation of hCD40 Tg B cells WT or KO for FcγRIIB with various concentrations of the indicated ChiLob 7/4 isotypes determined by 3H thymidine incorporation (mean and range of duplicates, 1 of 4 experiments). (D) hCD40 Tg mice (n=3-5) that were FcγR WT, FcγRIIB KO or common g chain KO (no activatory FcγR) received OTI cells then OVA plus the indicated ChiLob 7/4 mAb. Circulating OTI cells were enumerated at day 5. Combined results from 2 experiments. (E) hCD40Tg/FcγRIIB KO mice received OTI cells then were immunized with OVA alone (con) or with 200 mg ChiLob 7/4 h1 or h2 Fab'2 i.v. on D0 followed by 100 mg Fab'2 on days 1 and 2. Circulating OTI cells on D5 are shown. Similar results were obtained when mice were given a single 100 mg dose of h2 Fab'$_2$ i. v. (not shown). ***p<0.001, *p<0.05.

Example 11

This example relates to the experiments in FIG. 11 (a)-(f) which validates that ChiLob 7/4 h2 agonistic activity is FcγR independent. (A and B) SPR profiles to show binding of the indicated human (A) and mouse (B) FcγR at 100 nM to ChiLob 7/4 h1 or h2 immobilized at 15,000 RU. All profiles are presented on the same scale (Y axis to 2500 RU) to allow comparison of relative binding. The insets for FcγRIIA show the same data plotted with a Y axis scale of 200 RU to reveal low level binding. (C) To demonstrate integrity of the bound mAb, the binding of 100 nM hCD40 protein (solid line) or hOX40 protein (broken line) to the h1 and h2 mAb immobilized on the flow cells used in A and B was determined. (D) Background binding of hFcγRI and IIB to immobilized BSA. Similar results were obtained for all FcγR. This background was subtracted from the profiles in A and B. (E) To demonstrate integrity of the hFcγRIIB, anti-FcγRIIB specific mAb (KB61) was immobilized and the binding of hFcγRI and IIB compared. (F) Purified hCD40Tg mouse B cells were incubated for 16 hours with 1 mg/ml ChiLob 7/4 h2 IgG alone (left, black bar) or in the presence of a 50-fold excess of the indicated ChiLob 7/4 IgG fragments. CD23 expression was analyzed by flow cytometry after 20 h (top panel; grey histogram untreated cells, black line mAb treated cells) and B cell proliferation by $^3$H thymidine incorporation after 5 days (bottom panel, mean and range of duplicate samples). Results from 1 of 2 experiments are shown.

Example 12

This example relates to the experiments in FIG. 12 (a)-(e) which show the antagonistic effect of human IgG2 against multiple receptor targets. (A) Activation of human B cells with SGN40-Soton h1 or h2 was assessed as in FIG. 8A, 1 of 5 experiments shown (mean and range of duplicate samples). (B) hCD40 Tg B-cell proliferation (WT or FcγRIIB KO) in response to SGN40 h1 and h2 or the parental SC26 m1 (mean and range of duplicates, 1 of 3 experiments). (C) hCD40Tg/FcγRIIB KO mice (n=5) received 071 cells and were then immunized with OVA alone (con) or with 100 mg SGN40-Soton h1 or h2. Circulating OTI cells were enumerated on D5, ***p<0.001, 1 of 2 experiments shown. (D and E) Activation and proliferation of human CD4 T cells in total PBMC (C) or purified T cell (D) cultures in response to chimeric h1, h2 or h4 anti-h4-1BB or hCD28. Points represent individual donors.

Example 13

This example relates to the experiments in FIG. 13 showing that CH1 and hinge regions confer activity to ChiLob7/4 h2. (A) Schematics of ChiLob 7/4 h1 and h2 (left) and mutants (top) where the CH1 ((i) CH1 1/2 and (ii) CH1 2/1) or CH1 and hinge regions ((iii) CH1Hge 1/2 and (iv) CH1Hge 2/1) of h1 and h2 were swapped. Middle: CD23 expression on human B cells in the absence or presence of FcγRIIB expressing cross-linking cells, and bottom: hCD40 Tg FcγRIIB WT or KO B-cell proliferation in response to the chimeric mAb (mean and range of duplicates). (B) OTI responses in hCD40 Tg mice (n=3) treated with the indicated mAb determined as in FIG. 10E. Combined data from 2 experiments ****p<0.0001.

Example 14

This example relates to the control experiments in FIG. 14 validating that ChiLob 7/4 switch mutants bind similarly to CD40. Purified hCD40Tg mouse B cells were incubated with ChiLob 7/4 h1-FITC pre-mixed with different ratios of the indicated unlabeled mutants and analyzed as shown in FIG. 8.

Example 15

This example relates to the experiments in FIG. 15 (a))-(h) showing that mutagenesis generates a range of ChiLob 7/4 h2 agonistic forms. (A) nrCE-SDS profiles (top) and hCD40 Tg B-cell proliferation in response to 'skewed' h2A and h2B ChiLob 7/4 (mean and range of duplicates, 1 of 3 experiments). (B) nrCE-SDS profiles (top) and mouse B cell activation assessed by CD23 upregulation in the presence and absence of FcγRIIB expressing cross-linking cells (bottom) in response to skewed 3/23 h2, 1 of 3 experiments shown. (C) nrCE-SDS profiles of the indicated ChiLob 7/4 mutants. Positions of whole IgG, HCHC complexes (HH), free LC (L) and 10 kDa marker are shown. (D) Proliferation of hCD40 Tg B cells that were WT or KO for FcγRIIB in response to ChiLob 7/4 mutants (mean and range of duplicates from 1 of at least 3 experiments). (E) Western blot of lysates from hCD40 Tg mouse B cells treated with ChiLob 7/4 h2A and h2B at 1 mg/ml for the indicated times and probed with Ab specific for phosph-IKKa/b, phospho IkB-a or IkB-a. Anti-tubulin was used as a loading control. (F) SPR of ChiLob 7/4 h2 mutants (100, 20, 4, 0.8 and 0.16 nM) binding to hCD40 immobilised at 8000 RU. (G) hCD40 Tg B-cell proliferation with ChiLob 7/4 h2, h2A (HC C233S), skewed h2B, or a 1:1 mixture of h2A:h2B. Mean and range of duplicates from 1 of >5 experiments. (H and I) OVA-specific OTI CD8 T-cell responses (H) and day 18 serum Ab responses (I) in hCD40 Tg FcγRIIB KO mice (n=5) immunized with OVA plus 100 mg of ChiLob 7/4 C233S (h2A) or skewed h2B. Results from 1 of 2 experiments. p<0.01, *p<0.001.

Example 16

This example relates to the experiments in FIG. 16 (a)-(g) which further validate the differential activity of ChiLob 7/4 h2A and h2B forms. (A) Activation of purified human B cells assessed by homotypic adhesion (top) and CD23 upregulation (bottom) after incubation with native, 'A' or 'B' skewed forms of ChiLob 7/4 h2 at 200 ng/ml for 16 h. (B) Purified hCD40Tg B cells were incubated with the indicated concentrations of ChiLob 7/4 h2, CH1Hge 2/1 mutant or skewed forms of the mutant and proliferation measured as in FIG. 15A (mean and range of duplicate samples). (C) hCD40Tg mouse B cell proliferation in response to increasing concentrations of h2B skewed ChiLob 7/4 h2 IgG or Fab'2, measured as in B. (B) Western blot of lysates from Ramos cells treated with ChiLob 7/4 h2A and h2B at 1 mg/ml for the indicated times and probed with Ab specific for phosph-IKKa/b, phospho IkB-a or IkB-a. Anti-tubulin was used as a loading control. (E) Purified hCD40Tg mouse B cells were incubated with ChiLob 7/4 h1-FITC pre-mixed with different concentrations of the indicated unlabeled mutants and analyzed as in FIG. 13D. (F) and (G) hCD40Tg FcγRIIB KO mice that had been adoptively transferred with OTI cells were immunized with 100 mg OVA plus 100 mg of the skewed mutant mAb as in FIG. 12. Circulating OTI cells were enumerated over time (mean+/−SD for 5 animals per group) (D) and anti-OVA antibodies in the sera measured on day 18 (E). Results of one of 2 similar experiments are shown. *p<0.05, ***p<0.001.

CONCLUSIONS

Recent clinical data have suggested that immunostimulatory mAb's may be useful as therapeutics, e.g., in treating cancer Hodi et al., (2010); Wolchok et al., (2013); Topalian et al., (2012); Brahmer et al., (2012) and infectious disease. However, the identification of mAbs and fusion proteins which may be used in vivo for treatment requires a clear understanding of precise mechanisms of action. A large body of data now indicates that isotype selection is crucial as it dictates differential FcγR interactions that mediate events after Ag binding Nimmerjahn et al., (2012); White et al., (2013)). Manipulation of the mAb Fc has already been suggested as a way to enhance selected interactions and increase therapeutic potency through crosslinking of Fc by FcγRIIB (white et al., (2013); Li and Ravetch) (2012); Li and Ravetch)(2013)). The data herein instead suggest that isotype-dependent, but FcγR-independent mechanisms, may also be an important determinants of activity.

A role for FcγR engagement has been demonstrated for many anti-cancer mAb. In the case of anti-CD40, binding to FcγRIIB has been shown by us and others to be essential for activity in pre-clinical models, through a requirement for mAb cross-linking White et al., (2011); Li and Ravetch (2011)). This poses a challenge when developing agents for human use as no human IgG isotype binds with sufficiently high affinity to FcγRIIB to mediate this function. The requirement for FcγRIIB engagement is also potentially limiting as this receptor may not always be co-localized with the mAb target antigen. The demonstration in this report that mAb of the h2 isotype possess FcγR-independent agonistic activity is thus significant as it provides the opportunity to develop reagents that are agonistic regardless of target cell location.

The observation that h2 mAb do not require extrinsic cross-linking for agonistic activity is unique and surprising. The human IgG2 isotype is exceptional in its ability to rearrange disulfide bonds within its hinge and $C_H1$ domains after synthesis resulting in isoforms with distinct conformations (Martinez et al., (2008); Dillon et al., (2008); Allen et al., (2009)). IgG2 is believed to be synthesized with a classical, flexible IgG structure (its 'A' form) containing 4 inter-HC hinge disulfide bonds. Over time this is converted thorough a series of intermediates to a more rigid and compact 'B' form in which the LC and HC $C_H1$ are disulfide bonded to HC hinge cysteines 232 and 233(Martinez et al., (2008); Dillon et al., (2008); Allen et al., (2009)). Using a series of genetically engineered mAb, we demonstrated that the agonistic activity of LOB7.4 h2 was dependent upon its ability to shuffle disulfide bonds in the hinge. Moreover, mutation of specific cysteines or combinations of cysteine residues could lock it into antagonistic and agonistic conformations.

Previous investigators reported limited influence of disulfide shuffling on h2 activity, with a tendency for the B isoform to have lower affinity and reduced potency. However, in those cases activity was measured in terms of antigen binding or the ability to block receptor-ligand interactions Dillon et al., (2008). We found no difference in CD40 binding by agonistic and antagonistic forms of LOB7.4 h2. We speculate that more rigid and compact forms of h2, similar to h2B, can form dense, organized complexes with CD40 in the membrane allowing TRAF recruitment and downstream intracellular signalling, rather like cross-linking. The capacity of more flexible forms of h2, like h2A, to inhibit function may reflect an ability to disrupt these complexes, and may explain the characteristic bell-shaped curve observed when native h2 activity or that of mixtures of h2A and h2B forms is measured over a wide concentration range. Potentially the different forms of LOB7.4 h2 will be crystallized to determine their precise conformations and elucidate their mechanism of action. The observation that h2 constant regions also conferred FcγR-independent activity to another anti-hCD40 mAb, SGN40, as well as mAb directed against co-stimulatory molecules expressed on T cells (4-1BB and CD28) suggest that this may be a general property of this isotype.

The finding by us and others that agonistic anti-CD40, at least in murine models, requires binding to FcγRIIB (Li and Ravetch, 2011; White et al., 2011) poses a challenge when developing agents for human use as human IgG bind to FcγRIIB with very low affinity, particularly as monomers (Bruhns et al., 2009). Although Fc engineering can enhance FcγRIIB interaction and improve activity (Li and Ravetch, 2012; Li and Ravetch, 2013; White et al., 2013) this approach is limited by the fact that FcγRIIB may not always be available for cross-linking within the tumour microenvironment and may also result in adverse events when FcγRIIB is engaged on endothelial cells (Xu et al., 2003). The demonstration in this report that mAb of the h2 isotype possess FcγR-independent agonistic activity is thus significant as it provides the opportunity to develop reagents that are agonistic regardless of target cell location. The human IgG2 isotype is unique in its ability to rearrange disulfide bonds within its hinge and $C_{H1}$ domains after synthesis resulting in a range of isoforms with distinct conformations (Allen et al., 2009; Dillon et al., 2008; Martinez et al., 2008; Wypych et al., 2008). It is believed to be synthesized with a classical, flexible IgG structure (its 'A' form) containing 4 inter-HC hinge disulfide bonds. Over time this is converted through a series of intermediates to a more compact 'B' form in which the LC and HC CH1 are disulfide bonded to HC hinge cysteines 232 and 233 (Allen et al., 2009; Dillon et al., 2008; Liu et al., 2008; Martinez et al., 2008; Wypych et al., 2008). Using both a chemical skewing approach and a series of genetically engineered mAb, we have demonstrated that the agonistic activity of ChiLob 7/4 h2 is dependent upon its ability to adopt the h2B form. Moreover, mutation of specific cysteines or combinations thereof could lock it into conformations with different degrees of agonistic activity.

Of note, the selected light chain appears to affect the ability of h2 to adopt different conformations, with disulfide shuffling permitted by kappa but not lambda light chains (Dillon et al., 2008). Consistent with this, all mAb used in our study contained the kappa light chain. Of further interest, the existence of disulfide linked h2 dimers has been described in human blood (Yoo et al., 2003). However, as also reported by others using recombinant mAb (Martinez et al., 2008) we found no evidence of dimers in any of our mAb preparations, as revealed by nrCE-SDS.

Previous attempts to investigate the functional impact of h2A and h2B isoforms have not revealed differences in FcγR or C1q engagement (Lightle et al., 2010), or consistent differences in Ag binding or the ability to block receptor-ligand interactions, where if anything h2B is less active (Dillon et al., 2008; Guo et al., 2008; Martinez et al., 2008). Similarly, we did not observe any difference in the avidity of ChiLob 7/4 h2A and h2B forms for CD40 when measured by SPR or by flow cytometry. Combined with the very similar affinities of ChiLob 7/4 h1 and h2 Fab for CD40, it seems highly unlikely that changes in affinity can explain the very different properties of h2A and h2B. Interestingly, Liu et al (Liu et al., 2008) also showed in patients the natural conversion from the A to B form over a number of days that did not result from a change in half-life. Herein we assessed the agonistic activity of mAb engaging immune coreceptors, where we know that receptor clustering is a mandatory requirement to initiate downstream immune activation (Elgueta et al., 2009). Finding an antibody format that can achieve such crosslinking without FcγR engagement is both unexpected and unexplained, as almost all agonistic mAb described to date, including the anti-CD28 superagonist, TGN1412, which caused catastrophic toxicity in healthy volunteers in 2006 (Suntharalingam et al., 2006), require FcγR crosslinking for activity (Bartholomaeus et al., 2014). We speculate that the agonistic properties of h2B result from its unusual compact conformation where the Fab' arms are rotated down close to the Fc region of the antibody. This may allow close 'packing' of adjacent receptors engaged in the plane of the membrane. The lack of flexibility in h2B may also hold receptors in a more rigid lattice that favors efficient downstream signalling. An extension of this may be that h2B, unlike h2A, can stabilize receptors in pre-existing clusters (Smulski et al., 2013), while the flexible h2A may cause dissociation of these clusters. As h2 is the predominant isotype produced in response to bacterial polysaccharides (Barrett and Ayoub, 1986) the ability to form h2B may be an evolutionary response driven by the need to engage these repetitive, closely packed, epitopes.

The characteristic bell-shaped curves observed in this study when mixtures of anti-CD40 h2A and h2B were used to stimulate B cells whereby decreased activity was seen at higher concentrations (e.g. FIG. 10D) may reflect the ability of the more flexible h2A form to outcompete crosslinking by the more structurally constrained h2B form. This could perhaps be due to the flexible h2A binding more efficiently to target molecules which are continually moving in a fluid plasma membrane. Further studies may determine more precisely the configurations of the different forms of h2 which may shed more light on their precise modes of action. The observation that h2 constant regions also conferred FcγR-independent activity on another anti hCD40 mAb, SGN40, as well as mAbs directed against other receptors (4-1BB and CD28) suggest this may be a general property of this restricted conformation.

In vivo experiments in hCD40Tg mice clearly demonstrated the different mechanisms of action of ChiLob 7/4 when administered as a chimeric m1 versus h2 mAb. In both cases immunostimulation was observed, however the activity of m1 was dependent upon FcγRIIB expression, whereas that of h2 was completely independent of FcγR interaction. This raises the possibility of further enhancing activity by engineering reagents to simultaneously engage both mechanistic pathways; for example a chimeric CH1Hge 2/1 containing the SE/LF mutation to increase FcγRIIB affinity (Chu et al., 2008). This is the subject of ongoing investigation. In addition, although h2 activity in our study was FcγR-independent it will be important to determine whether its activity can be influenced in vivo by the presence of human FcγR that may bind h2 immobilized on the cell surface with sufficient affinity to allow cross-linking, particularly in patients expressing FcγRIIA-$^{131}$H or FcγRIIIA-$^{158}$V (Lux et al., 2013).

Importantly, the most agonistic of the anti-CD40 mAb in clinical trial to date is CP870,893 which is an h2, unlike the less agonistic ChiLob 7/4 and SGN40 which are both h1. The maximum tolerated dose of CP870,893 is at least 10-fold lower than those for ChiLob 7/4 or SGN40 (Vonderheide and Glennie 2013), and promising clinical data are emerging with this agent in both pancreatic cancer and metastatic melanoma patients (Bajor et al., 2014; Beatty et al., 2013). As in the current study, Richman and Vonderheide recently demonstrated that the in vitro agonistic activity of CP870,893 is both Fc and FcγR independent (Richman and Vonderheide, 2014). This is significant as it suggests that FcγR-independent pathways can deliver results in a clinical setting and our current findings might go some way towards explaining the unusual potency of CP870,893.

The data presented have profound implication for the development of agonistic mAb based therapeutics. Equipped with these insights it should be possible to manipulate the disulfide bond configuration of h2 to control the activity and toxicity of mAb directed against a range of immune receptors thereby permitting the fine-tuning of biological function and the subsequent development of novel therapeutics independent of FcγR interaction.

Monoclonal antibodies (mAb) that stimulate anti-cancer immunity provide curative therapy in a subset of patients with traditionally terminal malignancies. Realization of the full potential of these agents, however, will require precise engineering provided by a detailed understanding of their mechanisms of action. Here we demonstrate that human IgG2 (h2) constant regions provide mAb targeting three immunostimulatory co-receptors in clinical development—CD40, 4-1BB and CD28—with agonistic activity independent of Fcγ⍰-1BB and CD28—with agonistic activi required for receptor clustering and downstream intracellular signalling. This exceptional activity is conferred by the unique configuration of disulfide bonds in the h2 hinge and paves the way for engineering improved clinical reagents with defined activity regardless of FcγR expression in the local microenvironment.

In conclusion, we demonstrate herein that immunostimulatory mAbs have FcγR-independent agonistic activity when expressed as h2 that is dependent upon the unique ability of h2 to shuffle disulfide bonds in its hinge region. The use of h2 may thus allow the development of intrinsically active therapeutic agents that do not depend upon FcγR for function, with a long serum half-life, and that are active independent of cell type or anatomical location. The data also indicate that manipulating h2 mAb by the modification of disulfide bonds as described herein results in either agonist or antagonist agents, e.g., IgG2 antibodies or IgG2 fusion proteins, that can be used to stimulate or dampen immune responses, respectively, e.g., those elicited by B7/CD28 or TNF/TNFR family members. These agonists and antagonists will find application in the treatment of many diseases, e.g., cancer, autoimmunity, infectious diseases, allergy, and inflammatory conditions.

Therapeutic Applications

The subject agonistic and antagonistic antibodies may be used in treating any condition wherein agonizing or antagonizing the effect of a specific receptor or ligand will be clinically relevant. For example, these antibodies and fusion proteins may be useful in treating autoimmune disorders such as acquired sphenic atrophy, acute anterior uveitis, Acute Disseminated Encephalomyelitis (ADEM), acute gouty arthritis, acute necrotizing hemorrhagic leukoencephalitis, acute sinusitis, chronic sinusitis, acute purulent meningitis, other central nervous system inflammatory disorders, acute serious inflammation, Addison's disease, adrenalitis, adult onset diabetes mellitus (Type II diabetes), adult-onset idiopathic hypoparathyroidism (AOIH), Agammaglobulinemia, agranulocytosis, vasculitides, including vasculitis, large vessel vasculitis, polymyalgia rheumatic and giant cell (Takayasu's) arthritis, allergic conditions, allergic contact dermatitis, allergic dermatitis, allergic granulomatous angiitis, allergic hypersensitivity disorders, allergic neuritis, allergic reaction, alopecia areata, alopecia totalis, Alport's syndrome, alveolitis (allergic alveolitis, fibrosing alveolitis, Alzheimer's disease, amyloidosis, amylotrophic lateral sclerosis (ALS; Lou Gehrig's disease), an eosinophil-related disorder, eosinophilia, anaphylaxis, ankylosing spondylitis, angiectasis, antibody-mediated nephritis, Anti-GBM/Anti-TBM nephritis, antigen-antibody complex-mediated diseases, antiglomerular basement membrane disease, anti-phospholipid antibody syndrome, antiphospholipid syndrome (APS), aphthae, aphthous stomatitis, aplastic anemia, arrhythmia, arteriosclerosis, arteriosclerotic disorders, arthritis, rheumatoid arthritis, optionally acute arthritis, chronic rheumatoid arthritis, arthritis chronica progrediente, arthritis deformans, ascariasis, aspergilloma, granulomas containing eosinophils, aspergillosis, aspermiogenese, asthma, asthma bronchiale, bronchial asthma, and autoimmune asthma, ataxia telangiectasia, ataxic sclerosis, atherosclerosis, autism, autoimmune angioedema, autoimmune aplastic anemia, autoimmune atrophic gastritis, autoimmune diabetes, autoimmune disease of the testis and ovary including autoimmune orchitis and oophoritis, autoimmune disorders associated with collagen disease, autoimmune dysautonomia, autoimmune ear disease, autoimmune inner ear disease (AGED), autoimmune endocrine diseases including thyroiditis, autoimmune thyroiditis, autoimmune enteropathy syndrome, autoimmune gonadal failure, autoimmune hearing loss, autoimmune hemolysis, autoimmune hepatitis, autoimmune hepatological disorder, autoimmune hyperlipidemia, autoimmune immunodeficiency, autoimmune inner ear disease (AIED), autoimmune myocarditis, autoimmune neutropenia, autoimmune pancreatitis, autoimmune polyendocrinopathies, autoimmune polyglandular syndrome type I, autoimmune retinopathy, autoimmune thrombocytopenic purpura (ATP), autoimmune thyroid disease, autoimmune urticaria, autoimmune-mediated gastrointestinal diseases, axonal and neuronal neuropathies, Balo disease, Behcet's disease, benign familial and ischemia-reperfusion injury, benign lymphocytic angiitis, Berger's disease, IgA nephropathy, bird-fancier's lung, blindness, Boeck's disease, bronchiolitis obliterans, bronchitis, bronchopneumonic aspergillosis, Bruton's syndrome, bullous pemphigoid, Caplan's syndrome, Cardiomyopathy, cardiovascular ischemia, Castleman's syndrome, Celiac disease, celiac sprue (gluten enteropathy), cerebellar degeneration, cerebral ischemic, and disease accompanying vascularization, Chagas disease, channelopathies, epilepsy, channelopathies of the CNS, chorioretinitis, choroiditis, an autoimmune hematological disorder, chronic active hepatitis, autoimmune chronic active hepatitis, chronic contact dermatitis, chronic eosinophilic pneumonia, chronic fatigue syndrome, chronic hepatitis, chronic hypersensitivity pneumonitis, chronic inflammatory arthritis, chronic inflammatory demyelinating polyneuropathy (CIDP), chronic intractable inflammation, chronic mucocutaneous candidiasis, chronic neuropathy, IgM polyneuropathies, IgM-mediated neuropathy, chronic obstructive airway disease, chronic pulmonary inflammatory disease, Chronic recurrent multifocal osteomyelitis (CRMO), chronic thyroiditis (Hashimoto's thyroiditis) subacute thyroiditis, Churg-Strauss syndrome, cicatricial pemphigoid/benign mucosal pemphigoid, CNS inflammatory disorders, CNS vasculitis, Coeliac disease, Cogan's syndrome, cold agglutinin disease, colitis polyposa, colitis, optionally ulcerative colitis, colitis ulcerosa, collagenous colitis, conditions involving infiltration of T cells and chronic inflammatory responses, congenital heart block, congenital rubella infection, Coombs positive anemia, coronary artery disease, Coxsackie myocarditis, CREST syndrome (calcinosis, Raynaud's phenomenon), Crohn's disease, cryoglobulinemia, Cushing's syndrome, cyclitis, chronic cyclitis, heterochronic cyclitis, iridocyclitis, Fuch's cyclitis, cystic fibrosis, cytokine-induced toxicity, deafness, degenerative arthritis, demyelinating diseases, autoimmune demyelinating diseases, demyelinating neuropathies, dengue, dermatitis herpetiformis and atopic dermatitis, dermatitis including contact dermatitis, dermatomyositis, dermatoses with acute inflammatory components, Devic's disease (neuromyelitis optica), diabetic large-artery disorder, diabetic nephropathy, diabetic retinopathy, Diamond Blackfan anemia, diffuse interstitial pulmonary fibrosis, dilated cardiomyopathy, discoid lupus, diseases involving leukocyte diapedesis, Dressler's syndrome, Dupuytren's contracture, echovirus infection, eczema including allergic eczema, atopic eczema, encephalitis, optionally Rasmussen's encephalitis and limbic and/or brainstem encephalitis, encephalomyelitis, allergic encephalomyelitis, encephalomyelitis allergica and experimental allergic encephalomyelitis (EAE), endarterial hyperplasia, endocarditis, endocrine ophthalmopathy, endometriosis. endomyocardial fibrosis, endophthalmia phacoanaphylactica, endophthalmitis, enteritis allergica, eosinophilia-myalgia syndrome, eosinophilic fasciitis, epidemic keratoconjunctivitis, epidermolysis bullosa acquisita (EBA), episclera, episcleritis, Epstein-Barr virus infection, erythema elevatum et diutinum, erythema multiforme, erythema nodosum leprosum, erythema nodosum, erythroblastosis fetalis, esophageal dysmotility, essential mixed cryoglobulinemia, ethmoid, Evan's syndrome, experimental allergic encephalomyelitis (EAE), Factor VIII deficiency, farmer's lung, febris rheumatica, Felty's syndrome, fibromyalgia, fibrosing alveolitis, filariasis, focal segmental glomerulosclerosis (FSGS), food poisoning, frontal, gastric atrophy, giant cell arthritis (temporal arthritis), giant cell hepatitis, giant cell polymyalgia, glomerulonephritides, glomerulonephritis (GN) with and without nephrotic syndrome, chronic glomerulonephritis, acute glomerulonephritis optionally primary GN, Goodpasture's syndrome, gouty arthritis, granulocyte transfusion-associated syndromes, granulomatosis including lymphomatoid granulomatosis, granulomatosis with polyangiitis (GPA), granulomatous uveitis, Grave's disease, Guillain-Barre syndrome, gutatte psoriasis, hemoglobinuria paroxysmatica, Hamman-Rich's disease, Hashimoto's disease, Hashimoto's encephalitis, Hashimoto's thyroiditis, hemochromatosis, hemolytic anemia, immune hemolytic anemia including autoimmune hemolytic anemia (AIHA), hemolytic anemia, hemophilia A, Henoch-Schönlein purpura, Herpes gestationis, human immunodeficiency virus (HIV) infection, hyperalgesia, hypogammaglobulinemia, hypogonadism, hypoparathyroidism, idiopathic diabetes insipidus, idiopathic facial paralysis, idiopathic hypothyroidism, idiopathic IgA nephropathy, idiopathic membranous GN, idiopathic membranous nephropathy, idiopathic nephritic syndrome, idiopathic pulmonary fibrosis, idiopathic sprue, idiopathic thrombocytopenic purpura (ITP), IgA nephropathy, IgE-mediated diseases optionally anaphylaxis and allergic and atopic rhinitis, IgG4-related sclerosing disease, ileitis regionalis, immune complex nephritis, immune responses associated with acute and delayed hypersensitivity mediated by cytokines and T-lymphocytes, immune-mediated GN, immunoregulatory lipoproteins, including adult respiratory distress syndrome, acute respiratory distress syndrome (ARDS), inclusion body myositis, infectious arthritis, infertility due to antispermatozoan antibodies, inflammation of all or part of the uvea, inflammatory bowel disease (IBD) inflammatory hyperproliferative skin diseases, inflammatory myopathy, insulin-dependent diabetes (type 1), insulitis, interstitial cystitis, interstitial lung disease, interstitial lung fibrosis, iritis, ischemic re-perfusion disorder, joint inflammation, Juvenile arthritis, juvenile dermatomyositis, juvenile diabetes, juvenile onset (Type I) diabetes mellitus, including pediatric insulin-dependent diabetes mellitus (IDDM), juvenile-onset rheumatoid arthritis, Kawasaki syndrome, keratoconjunctivitis sicca, kypanosomiasis, Lambert-Eaton syndrome, leishmaniasis, leprosy, leucopenia, leukocyte adhesion deficiency, Leukocytoclastic vasculitis, leukopenia, lichen planus, lichen sclerosus, ligneous conjunctivitis, linear IgA dermatosis, Linear IgA disease (LAD), Loffler's syndrome, lupoid hepatitis, lupus, nephritis, cerebritis, pediatric, non-renal, extra-renal, discoid, alopecia, lupus (SLE), lupus erythematosus disseminatus, Lyme arthritis, Lyme disease, lymphoid interstitial pneumonitis, malaria, male and female autoimmune infertility, maxillary, medium vessel vasculitis, Kawasaki's disease, polyarteritis nodosa, membrano- or membranous proliferative GN (MPGN), including Type I and Type II, and rapidly progressive GN, membranous GN (membranous nephropathy), Meniere's disease, meningitis, microscopic colitis, microscopic polyangiitis, migraine, minimal change nephropathy, mixed connective tissue disease (MCTD), mononucleosis infectiosa, Mooren's ulcer, Mucha-Habermann disease, multifocal motor neuropathy, multiple endocrine failure, multiple organ injury syndrome, those secondary to septicemia, trauma, hemorrhage, multiple organ injury syndrome, multiple sclerosis (MS), spino-optical MS, multiple sclerosis, mumps, muscular disorders, myasthenia gravis, thymoma-associated myasthenia gravis, myasthenia gravis, myocarditis, myositis, narcolepsy, necrotizing enterocolitis, and transmural colitis, and autoimmune inflammatory bowel disease, necrotizing, cutaneous, hypersensitivity vasculitis, neonatal lupus syndrome (NLE), nephrosis, nephrotic syndrome, neurological disease, neuromyelitis optica (Devic's), neuromyelitis optica, neuromyotonia, neutropenia, non-cancerous lymphocytosis, nongranulomatous uveitis, non-malignant thymoma, ocular and orbital inflammatory disorders, ocular cicatricial pemphigoid, oophoritis, ophthalmia symphatica, opsoclonus myoclonus syndrome (OMS), opsoclonus, opsoclonus myoclonus syndrome (OMS), and sensory neuropathy, optic neuritis, orchitis granulomatosa, osteoarthritis, palindromic rheumatism, pancreatitis, pancytopenia, PANDAS (Pediatric Autoimmune Neuropsychiatric Disorders Associated with *Streptococcus*), paraneoplastic cerebellar degeneration, paraneoplastic syndrome, paraneoplastic syndromes, including neurologic paraneoplastic syndromes (e.g., Lambert-Eaton myasthenic syndrome, Eaton-Lambert syndrome, parasitic diseases, Leishmania, paroxysmal nocturnal hemoglobinuria (PNH), Parry Romberg syndrome, pars planitis (peripheral uveitis), Parsonnage-Turner syndrome, parvovirus infection, pemphigoid, pemphigoid bullous and skin pemphigoid, pemphigus, pemphigus vulgaris, pemphigus erythematosus, pemphigus foliaceus, pemphigus mucus-membrane pemphigoid, pemphigus, peptic ulcer, periodic paralysis, peripheral neuropathy, perivenous encephalomyelitis, pernicious anemia (anemia perniciosa), pernicious anemia, phacoantigenic uveitis, pneumonocirrhosis, POEMS syndrome, polyarteritis nodosa, Type I, II, & III, polyarthritis chronica primaria, polychondritis, refractory, relapsed polychondritis, polyendocrine autoimmune disease, polyendocrine failure, polyglandular syndromes, autoimmune polyglandular syndromes (or polyglandular endocrinopathy syndromes), polymyalgia rheumatica, polymyositis, polymyositis/dermatomyositis, polyneuropathies, polyradiculitis acuta, post-cardiotomy syndrome, posterior uveitis, autoimmune uveitis, postmyocardial infarction syndrome, postpericardiotomy syndrome, post-streptococcal nephritis, post-vaccination syndromes, presenile dementia, primary biliary cirrhosis, primary hypothyroidism, primary idiopathic myxedema, primary lymphocytosis, which includes monoclonal B cell lymphocytosis, benign monoclonal gammopathy and monoclonal gammopathy of undetermined significance, MGUS, primary myxedema, primary progressive MS (PPMS), and relapsing remitting MS (RRMS), primary sclerosing cholangitis, progesterone dermatitis, progressive systemic sclerosis, proliferative arthritis, psoriasis, plaque psoriasis, psoriasis, psoriatic arthritis, pulmonary alveolar proteinosis, pulmonary infiltration eosinophilia, pure red cell anemia, aplasia (PRCA), pure red cell aplasia, purulent, nonpurulent sinusitis, pustular psoriasis and psoriasis of the nails, pyelitis, pyoderma gangrenosum, Quervain's thyroiditis, Raynaud's phenomenon, reactive arthritis, recurrent abortion, reduction in blood pressure response, reflex sympathetic dystrophy, refractory sprue, Reiter's disease or syndrome, relapsing polychondritis, reperfusion injury of myocardial or other tissues, reperfusion injury, respiratory distress syndrome, restless legs syndrome, retinal autoimmunity, retroperitoneal fibrosis, Reynaud's syndrome, rheumatic diseases, rheumatic fever, rheumatism, rheumatoid arthritis, rheumatoid spondylitis, rubella virus infection, Sampter's syndrome, sarcoidosis, schistosomiasis, Schmidt syndrome, SCID and Epstein-Barr virus-associated diseases, sclera, scleritis, sclerodactyl, scleroderma, systemic scleroderma, sclerosing cholangitis, sclerosis disseminata, sclerosis, systemic sclerosis, sensoneural hearing loss, seronegative spondyloarthritides, Sheehan's syndrome, Shulman's syndrome, silicosis, Sjögren's syndrome, sperm & testicular autoimmunity, sphenoid sinusitis, Stevens-Johnson syndrome, stiff-man (stiff-person) syndrome, subacute bacterial endocarditis (SBE), subacute cutaneous lupus erythematosus, sudden hearing loss, Susac's syndrome, Sydenham's chorea, sympathetic ophthalmia, systemic lupus erythematosus (SLE), systemic lupus erythematodes, cutaneous SLE, systemic necrotizing vasculitis, and ANCA-associated vasculitis, Churg-Strauss vasculitis, syndrome (CSS), tabes dorsalis, Takayasu's arteritis, telangiectasia, temporal arteritis/Giant cell arteritis, thromboangiitis ubiterans, thrombocytopenia including thrombotic thrombocytopenic purpura (TTP) and autoimmune or immune-mediated thrombocytopenia, idiopathic thrombocytopenic purpura (ITP) including chronic or acute ITP, thrombocytopenic purpura (UP), thyrotoxicosis, tissue injury, Tolosa-Hunt syndrome, toxic epidermal necrolysis, toxic-shock syndrome, transfusion reaction, transient hypogammaglobulinemia of infancy, transverse myelitis, traverse myelitis, tropical pulmonary eosinophilia, tuberculosis, ulcerative colitis, undifferentiated connective tissue disease (UCTD), urticaria, chronic allergic urticaria and chronic idiopathic urticaria, including chronic autoimmune urticaria, uveitis, anterior uveitis, uveoretinitis, valvulitis, vascular dysfunction, vasculitis, vertebral arthritis, vesiculobullous dermatosis, vitiligo, Wegener's granulomatosis (Granulomatosis with Polyangiitis (GPA), Wiskott-Aldrich syndrome, and x-linked hyper IgM syndrome.

In addition, these antibodies and fusion polypeptides may be useful in treating inflammatory disorders such as rheumatic diseases, rheumatoid arthritis, osteoarthritis, psoriatic arthritis spondyloarthropathies, ankylosing spondylitis, reactive arthritis, Reiter's syndrome, crystal arthropathies, gout, pseudogout, calcium pyrophosphate deposition disease, multiple sclerosis, Lyme disease, polymyalgia rheumatica; connective tissue diseases, systemic lupus erythematosus, systemic sclerosis, polymyositis, dermatomyositis, Sjögren's syndrome; vasculitides, polyarteritis nodosa, Wegener's granulomatosis, Churg-Strauss syndrome; inflammatory conditions including consequences of trauma or ischaemia, sarcoidosis; vascular diseases including atherosclerotic vascular disease, atherosclerosis, and vascular occlusive disease, atherosclerosis, ischemic heart disease, myocardial infarction, stroke, peripheral vascular disease, vascular stent restenosis; ocular diseases including uveitis, corneal disease, iritis, iridocyclitis, cataracts, acid reflux/heartburn, acne, acne vulgaris, allergies and sensitivities, Alzheimer's Disease, asthma, atherosclerosis, vascular occlusive disease, atherosclerosis, ischemic heart disease, myocardial infarction, stroke, peripheral vascular disease, vascular stent restenosis, autoimmune diseases, bronchitis, cancer, carditis, cataracts, Celiac Disease, chronic pain, chronic prostatitis, cirrhosis, colitis, connective tissue diseases, systemic lupus erythematosus, systemic sclerosis, polymyositis, dermatomyositis, Sjögren's Syndrome, corneal disease, Crohn's Disease, crystal arthropathies, gout, pseudogout, calcium pyrophosphate deposition disease, dementia, dermatitis, diabetes, dry eyes, eczema, edema, emphysema, fibromyalgia, gastroenteritis, gingivitis, glomerulonephritis, heart disease, hepatitis, high blood pressure, hypersensitivities, inflammatory bowel diseases, inflammatory conditions, consequences of trauma or ischemia, insulin resistance, interstitial cystitis, iridocyclitis, iritis, joint pain/arthritis/rheumatoid arthritis, Lyme disease, metabolic syndrome (Syndrome X), multiple sclerosis, myositis, nephritis, obesity, ocular diseases, uveitis, osteopenia, osteoporosis, Parkinson's Disease, pelvic inflammatory disease, periodontal disease, polyarteritis, polychondritis, polymyalgia rheumatica, psoriasis, reperfusion injury, rheumatic arthritis, rheumatic diseases, rheumatoid arthritis, osteoarthritis, psoriatic arthritis, rheumatoid arthritis, sarcoidosis, scleroderma, sinusitis, Sjögren's Syndrome, spastic colon, spondyloarthropathies, ankylosing spondylitis, reactive arthritis, Reiter's Syndrome, systemic candidiasis, tendonitis, transplant rejection, UTI's, vaginitis, vascular diseases, atherosclerotic vascular disease, vasculitides, polyarteritis nodosa, Wegener's Granulomatosis, Churg-Strauss Syndrome, and vasculitis.

Also, the subject agonists and antagonists may be used to treat allergic diseases such as bronchial asthma, allergic rhinitis, atopic dermatitis, and pollen and insect allergies, eczema, allergic rhinitis, hay fever, urticaria, urticaria (hives) and food allergies, and other atopic conditions.

Further, the subject agonists and antagonists may be used to treat different cancers such as carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; multiple myeloma and post-transplant lymphoproliferative disorder (PTLD).

Also, cancers amenable for treatment using the agonists and antagonists of the present invention include, but not limited to, carcinoma, lymphoma, blastoma, sarcoma, and leukemia or lymphoid malignancies. More particular examples of such cancers include bladder, ovarian, melanoma, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. Preferably, the cancer is selected from the group consisting of breast cancer, colorectal cancer, rectal cancer, non-small cell lung cancer, non-Hodgkin's lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, and multiple myeloma. The cancer may be an early advanced (including metastatic) bladder, ovarian or melanoma. The cancer may be colorectal cancer. The cancerous conditions amenable for treatment of the invention include metastatic cancers wherein VISTA expression by myeloid derived suppressor cells suppress antitumor responses and anti-invasive immune responses. The method of the present invention is particularly suitable for the treatment of vascularized tumors.

Further the subject agonists and antagonists may be used to treat infectious conditions, e.g., viral, bacterial, fungal or parasitic infectious conditions. Examples thereof include e.g., hepatitis B, hepatitis C, Epstein-Barr virus, cytomegalovirus, immunodeficiency virus (HIV) infection, HIV-1, HIV-2, herpes, papillomavirus infection and associated diseases, tuberculosis, malaria, schistosomiasis. echovirus infection, parvovirus infection, rubella virus infection, post-vaccination syndromes, congenital rubella infection, pertussis, influenza, mumps, and Epstein-Barr virus-associated diseases.

CD40 or CD27 agonistic or antagonistic antibodies according to the invention may in particular be used in treating conditions such as cancer, inflammatory, infectious and autoimmune diseases, transplant, GVHD, and for promoting the efficacy of vaccines.

The subject antibodies may be used alone or in association with other therapeutic agents wherein such therapeutic agents may include other biologics or non-biologics such as small molecules, chemotherapeutics, anti-infectives, anti-inflammatory agents, anti-allergenic agents, radionuclides, other receptor agonists or antagonists, hormone modulators, growth factor modulators and the like. Suitable therapeutics for treating cancer, infectious diseases, inflammatory conditions are known in the art. The selection of appropriate other therapeutic agent will depend on the specific condition being treated.

The subject agonists and antagonists of the invention when used for therapy will be incorporated into pharmaceutical compositions suitable for therapeutic administration. Such compositions will typically comprise an effective amount of the agonist or antagonist antibody or fusion protein and a carrier, e.g., a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™. (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the agonist or antagonist in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer. Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery. In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals. The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

REFERENCES

The contents of the all of references cited in this application are incorporated by reference in their entirety herein.
1. Advani, R., Forero-Torres, A., Furman, R. R., Rosenblatt, J. D., Younes, A., Ren, H., Harrop, K., Whiting, N., and Drachman, J. G. (2009). Phase I study of the humanized anti-CD40 monoclonal antibody dacetuzumab in refractory or recurrent non-Hodgkin's lymphoma. *J Clin Oncol* 27, 4371-4377.
2. Ahonen, C., Manning, E., Erickson, L. D., O'Connor, B., Lind, E. F., Pullen, S. S., Kehry, M. R., and Noelle, R. J. (2002). The CD40-TRAF6 axis controls affinity maturation and the generation of long-lived plasma cells. *Nat Immunol* 3, 451-456

3. Allen, M. J., Guo, A., Martinez, T., Han, M., Flynn, G. C., Wypych, J., Liu, Y. D., Shen, W. D., Dillon, T. M., Vezina, C., and Balland, A. (2009). Interchain disulfide bonding in human IgG2 antibodies probed by site-directed mutagenesis. *Biochemistry* 48, 3755-3766
4. Angal, S., King, D. J., Bodmer, M. W., Turner, A., Lawson, A. D., Roberts, G., Pedley, B., and Adair, J. R. (1993). A single amino acid substitution abolishes the heterogeneity of chimeric mouse/human (IgG4) antibody. *Mol Immunol* 30, 105-108.
5. Bajor, D. L., Xu, X., Torigian, D. A., Mick, R., Garcia, L., Richman, L., Desmarais, C., Nathanson, K. L., Schuchter, L. M., Kalos, M., and Vonderheide, R. H. (2014). Immune activation and a 9-year ongoing complete remission following CD40 antibody therapy and metastasectomy in a patient with metastatic melanoma. *Cancer Immunol Res* 2, 19-26.
6. Ball C, et al. (2012) Antibody C region influences TGN1412-like functional activity in vitro. *Journal of Immunology* 189(12):5831-5840.
7. Barrett, D. J., and Ayoub, E. M. (1986). IgG2 subclass restriction of antibody to pneumococcal polysaccharides. *Clin Exp Immunol* 63, 127-134.
8. Bartholomaeus, P., Semmler, L. Y., Bukur, T., Boisguerin, V., Romer, P. S., Tabares, P., Chuvpilo, S., Tyrsin, D. Y., Matskevich, A., Hengel, H., et al. (2014). Cell contact-dependent priming and Fc interaction with CD32+ immune cells contribute to the TGN1412-triggered cytokine response. *J Immunol* 192, 2091-2098.
9. Beatty, G. L., Chiorean, E. G., Fishman, M. P., Saboury, B., Teitelbaum, U. R., Sun, W., Huhn, R. D., Song, W., Li, D., Sharp, L. L., et al. (2011). CD40 agonists alter tumor stroma and show efficacy against pancreatic carcinoma in mice and humans. *Science* 331, 1612-1616.
10. Beatty, G. L., Torigian, D. A., Chiorean, E. G., Saboury, B., Brothers, A., Alavi, A., Troxel, A. B., Sun, W., Teitelbaum, U. R., Vonderheide, R. H., and O'Dwyer, P. J. (2013). A phase I study of an agonist CD40 monoclonal antibody (CP-870,893) in combination with gemcitabine in patients with advanced pancreatic ductal adenocarcinoma. *Clin Cancer Res* 19, 6286-6295.
11. Boross, P., Arandhara, V. L., Martin-Ramirez, J., Santiago-Raber, M. L., Carlucci, F., Flierman, R., van der Kaa, J., Breukel, C., Claassens, J. W., Camps, M., et al. (2011). The inhibiting Fc receptor for IgG, FcγRIIB, is a modifier of autoimmune susceptibility. *J Immunol* 187, 1304-1313.
12. Brahmer, J. R., Tykodi, S. S., Chow, L. Q., Hwu, W. J., Topalian, S. L., Hwu, P., Drake, C. G., Camacho, L. H., Kauh, J., Odunsi, K., et al. (2012). Safety and activity of anti-PD-L1 antibody in patients with advanced cancer. *New Engl J Med* 366, 2455-2465.
13. Bruhns, P., Iannascoli, B., England, P., Mancardi, D. A., Fernandez, N., Jorieux, S., and Daeron, M. (2009). Specificity and affinity of human Fcγ receptors and their polymorphic variants for human IgG subclasses. *Blood* 113, 3716-3725.
14. Bulliard, Y., Jolicoeur, R., Windman, M., Rue, S. M., Ettenberg, S., Knee, D. A., Wilson, N. S., Dranoff, G., and Brogdon, J. L. (2013). Activating Fc γ receptors contribute to the antitumor activities of immunoregulatory receptor-targeting antibodies. *J Exp Med* 210, 1685-1693.
15. Bulliard, Y., Jolicoeur, R., Zhang, J., Dranoff, G., Wilson, N. S., and Brogdon, J. L. (2014). OX40 engagement depletes intratumoral Tregs via activating FcγRs, leading to antitumor efficacy. *Immunol Cell Biol* 92, 475-480.
16. Bourke, E., Bosisio, D., Golay, J., Polentarutti, N., and Mantovani, A. (2003). The toll-like receptor repertoire of human B lymphocytes: inducible and selective expression of TLR9 and TLR10 in normal and transformed cells. *Blood* 102, 956-963.
17. Chowdhury, F., Johnson, P. W., Glennie, M. J., and Williams, A. P. (2014). Ex vivo assays of dendritic cell activation and cytokine profiles as predictors of in vivo effects in an anti-human CD40 monocloncal antibody ChiLob 7/4 phase 1 trial. *Cancer Immunol Res* 2, 229-240.
18. Chu, S. Y., Vostiar, I., Karki, S., Moore, G. L., Lazar, G. A., Pong, E., Joyce, P. F., Szymkowski, D. E., and Desjarlais, J. R. (2008). Inhibition of B cell receptor-mediated activation of primary human B cells by coengagement of CD19 and FcγRIIb with Fc-engineered antibodies. *Mol Immunol* 45, 3926-3933.
19. Clynes, R. A., Towers, T. L., Presta, L. G., and Ravetch, J. V. (2000). Inhibitory Fc receptors modulate in vivo cytotoxicity against tumor targets. *Nat Med* 6, 443-446.
20. Dillon, T. M., Ricci, M. S., Vezina, C., Flynn, G. C., Liu, Y. D., Rehder, D. S., Plant, M., Henkle, B., Li, Y., Deechongkit, S., et al. (2008) Structural and functional characterization of disulfide isoforms of the human IgG2 subclass. *J Biol Chem* 283, 16206-16215.
21. Elgueta, R., Benson, M. J., de Vries, V. C., Wasiuk, A., Guo, Y., and Noelle, R. J. (2009). Molecular mechanism and function of CD40/CD40L engagement in the immune system. *Immunol Rev* 229, 152-172.
22. French, R. R., Chan, H. T., Tutt, A. L., and Glennie, M. J. (1999). CD40 antibody evokes a cytotoxic T-cell response that eradicates lymphoma and bypasses T-cell help. *Nat Med* 5, 548-553.
23. French, R. R., Taraban, V. Y., Crowther, G. R., Rowley, T. F., Gray, J. C., Johnson, P. W., Tutt, A. L., Al-Shamkhani, A., and Glennie, M. J. (2007). Eradication of lymphoma by CD8 T cells following anti-CD40 monoclonal antibody therapy is critically dependent on CD27 costimulation. *Blood* 109, 4810-4815.
24. Glennie, M. J., McBride, H. M., Worth, A. T., and Stevenson, G. T. (1987). Preparation and performance of bispecific F(ab' gamma)2 antibody containing thioether-linked Fab' gamma fragments. *J Immunol* 139, 2367-2375.
25. Greenman, J., Tutt, A. L., George, A. J., Pulford, K. A., Stevenson, G. T., and Glennie, M. J. (1991). Characterization of a new monoclonal anti-Fc gamma RII antibody, AT10, and its incorporation into a bispecific F(ab')2 derivative for recruitment of cytotoxic effectors. *Mol Immunol* 28, 1243-1254.
26. Guo, A., Han, M., Martinez, T., Ketchem, R. R., Novick, S., Jochheim, C., and Balland, A. (2008). Electrophoretic evidence for the presence of structural isoforms specific for the IgG2 isotype. *Electrophoresis* 29, 2550-2556.
27. Hamaguchi, Y., Xiu, Y., Komura, K., Nimmerjahn, F., and Tedder, T. F. (2006). Antibody isotype-specific engagement of Fcγ receptors regulates B lymphocyte depletion during CD20 immunotherapy. *J Exp Med* 203, 743-753.
28. Hanks, B. A., Jiang, J., Singh, R. A., Song, W., Barry, M., Huls, M. H., Slawin, K. M., and Spencer, D. M. (2005). Re-engineered CD40 receptor enables potent pharmacological activation of dendritic-cell cancer vaccines in vivo. *Nat Med* 11, 130-137.
29. Hodi, F. S., O'Day, S. J., McDermott, D. F., Weber, R. W., Sosman, J. A., Haanen, J. B., Gonzalez, R., Robert, C., Schadendorf, D., Hassel, J. C., et al. (2010). Improved survival with ipilimumab in patients with metastatic melanoma. *New Engl J Med* 363, 711-723.

30. Johnson P W, Steve, N. M., Chowdhury, F., Dobbyn, J., Hall, E., Ashton-Key, M., Hodges, E., Ottensmeier, C. H., Williams, A., Glennie, M. J. (2010) A cancer research UK phase I study evaluating safety, tolerability, and biological effects of chimeric anti-CD40 monoclonal antibody (MAb), Chi Lob 7/4. *Journal of Clinical Oncology: official journal of the American Society of Clinical Oncology* 28(Suppl):abstr 2057.

31. Kohrt, H. E., Colevas, A. D., Houot, R., Weiskopf, K., Goldstein, M. J., Lund, P., Mueller, A., Sagiv-Barfi, I., Marabelle, A., Lira, R., et al. (2014). Targeting CD137 enhances the efficacy of cetuximab. *J Clin Invest* 124, 2668-2682.

32. Kohrt, H. E., Houot, R., Goldstein, M. J., Weiskopf, K., Alizadeh, A. A., Brody, J., Muller, A., Pachynski, R., Czerwinski, D., Coutre, S., et al. (2011). CD137 stimulation enhances the antilymphoma activity of anti-CD20 antibodies. *Blood* 117, 2423-2432.

33. Kohrt, H. E., Houot, R., Weiskopf, K., Goldstein, M. J., Scheeren, F., Czerwinski, D., Colevas, A. D., Weng, W. K., Clarke, M. F., Carlson, R. W., et al. (2012). Stimulation of natural killer cells with a CD137-specific antibody enhances trastuzumab efficacy in xenotransplant models of breast cancer. *J Clin Invest* 122, 1066-1075.

34. Kurai, J., Chikumi, H., Hashimoto, K., Yamaguchi, K., Yamasaki, A., Sako, T., Touge, H., Makino, H., Takata, M., Miyata, M., et al. (2007). Antibody-dependent cellular cytotoxicity mediated by cetuximab against lung cancer cell lines. *Clin Cancer Res* 13, 1552-1561.

35. Li, F., and Ravetch, J. V. (2011). Inhibitory Fcγ receptor engagement drives adjuvant and anti-tumor activities of agonistic CD40 antibodies. *Science* 333, 1030-1034.

36. Li, F., and Ravetch, J. V. (2012). Apoptotic and antitumor activity of death receptor antibodies require inhibitory Fcγ receptor engagement. *Proc Natl Acad Sci USA* 109, 10966-10971.

37. Li, F., and Ravetch, J. V. (2013). Antitumor activities of agonistic anti-TNFR antibodies require differential FcγRIIB coengagement in vivo. *Proc Natl Acad Sci USA* 110, 19501-19506

38. Lightle, S., Aykent, S., Lacher, N., Mitaksov, V., Wells, K., Zobel, J., and Oliphant, T. (2010). Mutations within a human IgG2 antibody form distinct and homogeneous disulfide isomers but do not affect Fc gamma receptor or C1q binding. Prot Sci 19, 753-762.

39. Liu, Y. D., Chen, X., Enk, J. Z., Plant, M., Dillon, T. M., and Flynn, G. C. (2008). Human IgG2 antibody disulfide rearrangement in vivo. *J Biol Chem* 283, 29266-29272.

40. Law C L, et al. (2005) Preclinical antilymphoma activity of a humanized anti-CD40 monoclonal antibody, SGN-40. *Cancer Research* 65(18):8331-8338.

41. Lux, A., Yu, X., Scanlan, C. N., and Nimmerjahn, F. (2013) Impact of immune complex size and glycosylation on IgG binding to human FcγRs. *J Immunol* 190, 4315-4323.

42. Martinez, T., Guo, A., Allen, M. J., Han, M., Pace, D., Jones, J., Gillespie, R., Ketcham, R. R., Zhang, Y., and Balland, A. (2008). Disulfide connectivity of human immunoglobulin G2 structural isoforms. *Biochemistry* 47, 7496-7508.

43. Moran, A. E., Kovacsovics-Bankowski, M., and Weinberg, A. D. (2013). The TNFRs OX40, 4-1BB, and CD40 as targets for cancer immunotherapy. *Curr Opin Immunol* 25, 230-237.

44. Nimmerjahn, F., and Ravetch, J. V. (2005). Divergent immunoglobulin g subclass activity through selective Fc receptor binding. *Science* 310, 1510-1512.

45. Nimmerjahn, F., and Ravetch, J. V. (2012). Translating basic mechanisms of IgG effector activity into next generation cancer therapies. *Cancer Immunity* 12, 13-19.

46. Polak M E, et al. (2012) CD70-CD27 interaction augments CD8+ T-cell activation by human epidermal Langerhans cells. *The Journal of Investigative Dermatology* 132(6):1636-1644.

47. Richman, L. P., and Vonderheide, R. H. (2014). Role of crosslinking for agonistic CD40 monoclonal antibodies as immune therapy of cancer. *Cancer Immunol Res* 2, 19-26.

48. Romer P S, et al. (2011) Preculture of PBMCs at high cell density increases sensitivity of T-cell responses, revealing cytokine release by CD28 superagonist TGN1412. *Blood* 118(26):6772-6782.

49. Ryazantsev, S., Tischenko, V., Nguyen, C., Abramov, V., and Zav'yalov, V. (2013). Three dimensional structure of the human myeloma IgG2. *PloS One* 8, e64076.

50. Sanchez, P. J., McWilliams, J. A., Haluszczak, C., Yagita, H., and Kedl, R. M. (2007). Combined TLR/CD40 stimulation mediates potent cellular immunity by regulating dendritic cell expression of CD70 in vivo. *J Immunol* 178, 1564-1572.

51. Simpson, T. R., Li, F., Montalvo-Ortiz, W., Sepulveda, M. A., Bergerhoff, K., Arce, F., Roddie, C., Henry, J. Y., Yagita, H., Wolchok, J. D., et al. (2013) Fc-dependent depletion of tumorinfiltrating regulatory T cells co-defines the efficacy of anti-CTLA-4 therapy against melanoma. *J Exp Med* 210, 1695-1710.

52. Sliwkowski, M. X., and Mellman, I. (2013). Antibody therapeutics in cancer. *Science* 341, 1192-1198.

53. Smulski, C. R., Beyrath, J., Decossas, M., Chekkat, N., Wolff, P., Estieu-Gionnet, K., Guichard, G., Speiser, D., Schneider, P., and Fournel, S. (2013). Cysteine-rich domain 1 of CD40 mediates receptor self-assembly. *J Biol Chem* 288, 10914-10922

54. Suntharalingam, G., Perry, M. R., Ward, S., Brett, S. J., Castello-Cortes, A., Brunner, M. D., and Panoskaltsis, N. (2006) Cytokine storm in a phase 1 trial of the anti-CD28 monoclonal antibody TGN1412. *New Engl J Med* 355, 1018-1028.

55. Topalian, S. L., Hodi, F. S., Brahmer, J. R., Gettinger, S. N., Smith, D. C., McDermott, D. F., Powderly, J. D., Carvajal, R. D., Sosman, J. A., Atkins, M. B., et al. (2012). Safety, activity, and immune correlates of anti-PD-1 antibody in cancer. *New Engl J Med* 366, 2443-2454.

56. Uchida, J., Hamaguchi, Y., Oliver, J. A., Ravetch, J. V., Poe, J. C., Haas, K. M., and Tedder, T. F. (2004). The innate mononuclear phagocyte network depletes B lymphocytes through Fc receptor-dependent mechanisms during anti-CD20 antibody immunotherapy. *J Exp Med* 199, 1659-1669.

57. Vonderheide, R. H., and Glennie, M. J., (2013). Agonistic CD40 antibodies and cancer therapy. *Clin Cancer Res* 19, 1035-1043.

58. Vonderheide R H, et al. (2007) Clinical activity and immune modulation in cancer patients treated with CP-870,893, a novel CD40 agonist monoclonal antibody. *Journal of Clinical Oncology: official journal of the American Society of Clinical Oncology* 25(7):876-883.

59. White, A. L., Chan, H. T., French, R. R., Beers, S. A., Cragg, M. S., Johnson, P. W., and Glennie, M. J. (2013). FcγRIIB controls the potency of agonistic anti-TNFR mAbs. *Cancer Immunol Immunother* 62, 941-948.

60. White, A. L., Chan, H. T., Roghanian, A., French, R. R., Mockridge, C. I., Tutt, A. L., Dixon, S. V., Ajona, D., Verbeek, J. S., Al-Shamkhani, A., et al. (2011). Interaction with FcγRIIB is critical for the agonistic activity of anti-CD40 monoclonal antibody. *J Immunol* 187, 1754-1763.

61. White, A. L., Dou, L., Chan, H. T. C., Field, V. L., Mockridge, C. I., Moss, K., Williams, E., Butts, C., Al-Shamkhani, A., Cragg, M. S., Verbeek, S. J., Johnson, P., Glennie, M. J., Beers, S. A. (2014). FcR dependence of agonistic CD40 antibody is related to anatomical location and can be overcome by antibody multimerization. *Journal of Immunology* 193, 1828-1835.

62. White, A. L., Tutt, A. L., James, S., Wilkinson, K. A., Castro, F. V., Dixon, S. V., Hitchcock, J., Khan, M., Al-Shamkhani, A., Cunningham, A. F., and Glennie, M. J. (2010). Ligation of CD11c during vaccination promotes germinal center induction and robust humoral responses without adjuvant. *Immunology* 131, 141-151.

63. Wilson, N. S., Yang, B., Yang, A., Loeser, S., Marsters, S., Lawrence, D., Li, Y., Pitti, R., Totpal, K., Yee, S., et al. (2011). An Fcγ receptor-dependent mechanism drives antibody mediated target-receptor signaling in cancer cells. *Cancer Cell* 19, 101-113.

64. Wolchok, J. D., Kluger, H., Callahan, M. K., Postow, M. A., Rizvi, N. A., Lesokhin, A. M., Segal, N. H., Ariyan, C. E., Gordon, R. A., Reed, K., et al. (2013). Nivolumab plus ipilimumab in advanced melanoma. *New Engl J Med* 369, 122-133.

65. Wypych, J., Li, M., Guo, A., Zhang, Z., Martinez, T., Allen, M. J., Fodor, S., Kelner, D. N., Flynn, G. C., Liu, Y. D., et al. (2008) Human IgG2 antibodies display disulfide-mediated structural isoforms. *J Biol Chem* 283, 16194-16205.

66. Xu, Y., Szalai, A. J., Zhou, T., Zinn, K. R., Chaudhuri, T. R., Li, X., Koopman, W. J., and Kimberly, R. P. (2003). Fc γRs modulate cytotoxicity of anti-Fas antibodies: implications for agonistic antibody-based therapeutics. *J Immunol* 171, 562-568.

67. Yoo, E. M., Wims, L. A., Chan, L. A., and Morrison, S. L., (2003). Human IgG2 can form covalent dimers. *J Immunol* 170, 3134-3138.

68. Zhang, B., Harder, A. G., Connelly, H. M., Maheu, L. L., and Cockrill, S. L. (2010).

Determination of Fab-hinge disulfide connectivity in structural isoforms of a recombinant human immunoglobulin G2 antibody. *Anal Chem* 82, 1090-1099.

Having described the invention and exemplary embodiments thereof, the invention is further described by the claims which follow.

The invention claimed is:

1. A method for obtaining an agonist antibody which binds to a desired immune receptor which comprises human IgG2 hinge and CH1 domain which are stabilized in the h2B conformation comprising:
   (i) obtaining a human IgG1, IgG3 or IgG4 antibody or antigen-binding fragment thereof which binds to a desired immune receptor; and
   (ii) replacing the hinge and CH1 domains human IgG1, IgG3 or IgG4 with the human IgG2 hinge and CH1 domains and
   (iii) replacing both the kappa light chain cysteine at position 214 (LC C214) and the heavy chain cysteine residue at position 127 (HC-C127) (numbering according to Kabat) with a serine residue; thereby obtaining the agonist antibody which binds to said desired immune receptor, which stabilized in the h2B conformation.

2. The method of claim 1, wherein the immune receptor is a TNFR receptor.

3. The method of claim 2, wherein the TNFR receptor is CD40, LTα, LTβ, CD30, CD27, OX40, 4-1BB, TNF-R, TRANCE-R, or glucocorticoid-induced TNF receptor (GITR).

4. The method of claim 2, wherein the TNFR is selected from the group consisting of 4-1BB, CD40 and CD27.

5. The method of claim 2, wherein the TNFR receptor is CD40.

6. The method of claim 1, wherein the human IgG1 hinge and CH1 domains thereof are replaced with human IgG2 hinge and CH1 domains wherein the kappa light chain cysteine at position 214 (LC C214) and the heavy chain cysteine residue at position 127 (HC C127) (wherein numbering is according to Kabat) are both replaced with a serine residue.

7. The method of claim 1, wherein the human IgG3 hinge and CH1 domains thereof are replaced with human IgG2 hinge and CH1 domains wherein the kappa light chain cysteine at position 214 (LC C214) and the heavy chain cysteine residue at position 127 (HC C127) (wherein numbering is according to Kabat) are both replaced with a serine residue.

8. The method of claim 1, wherein the human IgG4 hinge and CH1 domains thereof are replaced with human IgG2 hinge and CH1 domains wherein the kappa light chain cysteine at position 214 (LC C214) and the heavy chain cysteine residue at position 127 (HC C127) (wherein numbering is according to Kabat) are both replaced with a serine residue amino acid.

* * * * *